United States Patent
Cheng et al.

(10) Patent No.: US 7,132,257 B2
(45) Date of Patent: Nov. 7, 2006

(54) PRODUCTION OR AROMATIC CAROTENOIDS IN GRAM NEGATIVE BACTERIA

(75) Inventors: Qiong Cheng, Wilmington, DE (US); Pierre E. Rouviere, Wilmington, DE (US); Wonchul Suh, Wilmington, DE (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/886,906

(22) Filed: Jul. 8, 2004

(65) Prior Publication Data

US 2005/0019852 A1    Jan. 27, 2005

Related U.S. Application Data

(60) Provisional application No. 60/486,106, filed on Jul. 10, 2003.

(51) Int. Cl.
  C12P 23/00  (2006.01)
  C07H 12/04  (2006.01)
  C12N 9/10   (2006.01)
  C12N 1/21   (2006.01)
  C12N 15/74  (2006.01)

(52) U.S. Cl. .................. 435/67; 435/193; 435/252.3; 435/471; 435/419; 435/468; 536/23.2; 800/282

(58) Field of Classification Search .............. 435/67, 435/252.3, 254.2, 419, 468; 536/23.2; 800/282
See application file for complete search history.

(56) References Cited

OTHER PUBLICATIONS

WO 03/093200 A-2 Cheng Qiong et al. Method for the synthesis of Aryl-carotenoids May 6, 2002.*
Lee et al. Biosynthesis of stucturally Novel Carotenoids in *Escherichia coli*. May 2003. Chemistry and Biology, vol. 10, 453-462.*
Novy et al. Overcoming the codon bias of *E. coli* for enhanced protein expression Jun. 2001. InNovations news letter. vol. 12 article No. 1.*

Krubasik P. et al. Acarotenogenic gene cluster from Brevibacterium linines with novel lycopene cyclase gene involvedin the synthesis of aromatic carotenoids. 2000.Mol. Gen.Genet. 263(3), 423-432.*
G. Armstrong, 1999, Carotenoid Genetics and Biochemistry, In Comprehensive Natural Products Chemistry, Elsevier Press, vol. 2, pp. 321-352.
Krugel et al., Functional analysis of genes from *Streptomyces griseus* involved in the synthesis of isorenieratene, a carotenoid with aromatic end groups, revealed a novel type of carotenoid desaturase, Biochimica et Biophysica Acta, 1439: pp. 57-64, 1999.
Krubasik and Sandmann, A carotenogenic gene cluster from *Brevibacterium linens* with novel lycopene cyclase genes involved in the synthesis of aromatic carotenoids, Mol. Gen. Genet 263: 423-432, 2000.
Viveiros et al.,Structural and functional analysis of the gene cluster encoding carotenoid biosynthesis in *Mycobacterium aurum* A+, FEMS Microbiol Lett, 187: pp. 95-101, 2000.
Liaaen-Jensen et al., The Carotenoids of Photosynthetic Green Bacteria, ACTA Chem. Scand 18: 1703-1718, 1964.
Takaichi et al., New carotenoids from the thermophilic green sulfur bacterium *Chlorobium tepidum*: 1',2'-dihydro-y-carotene, 1'-2'dihydrochlorobactene, and OH-chlorobactene glucoside ester, and the the carotenoid composition of different strains, Arch. Microbiol. 168: 270-276, 1997.
Eisen et al., The complete genome sequence of *Chlorobium tepidum* TLS, a photosynthetic, anaerobic, green-sulfur bacterium, PNAS USA, 99: 9509-9514, 2002.
Schumann et al., Activation and analysis of cryptic crt genes fro carotenoid biosynthesis from *Streptomyces griseus*, Mol. Gen. Genet, vol. 252: pp. 658-666, 1996.
Lee et al., Biosynthesis of Structurally Novel Carotenoids in *Escherichia coli*, Chem Biol 10(5): pp. 453-462, 2003.
Kohl et al., The Pigment of *Brevibacterium Linens*: Aromatic Carotenoids, Phytochemistry, vol. 22: pp. 207-213, 1983.

* cited by examiner

*Primary Examiner*—Rebecca E. Prouty
*Assistant Examiner*—Kagnew Gebreyesus

(57) ABSTRACT

A method for the in vivo bioconversion of cyclic carotenes having a β-ionone ring to the corresponding aryl carotene is provided. Gram negative host cells expressing a heterologous, codon-optimized gene encoding a carotene desaturase are grown in the presence of a suitable cyclic carotene substrate to effect the production of aromatic carotenoids.

4 Claims, 6 Drawing Sheets
(1 of 6 Drawing Sheet(s) Filed in Color)

PRODUCTION OR AROMATIC CAROTENOIDS IN GRAM NEGATIVE BACTERIA

This application claims the benefit of U.S. Provisional Application No. 60/486,106 filed Jul. 10, 2003.

FIELD OF THE INVENTION

This invention is in the field of microbiology. More specifically, this invention pertains to nucleic acid fragments encoding enzymes useful for production of aromatic carotenoid compounds.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish, and birds. Colors range from yellow to red with variations of brown and purple. As precursors of vitamin A, carotenoids are fundamental components in our diet and they play an important role in human health. Industrial uses of carotenoids include pharmaceuticals, food supplements, animal feed additives, and colorants in cosmetics, to mention a few. Because animals are unable to synthesize carotenoids de novo, they must obtain them by dietary means. Thus, manipulation of carotenoid production and composition in bacteria can provide new or improved sources for carotenoids.

Carotenoids come in many different forms and chemical structures. Most naturally occurring carotenoids are hydrophobic tetraterpenoids containing a $C_{40}$ methyl-branched hydrocarbon backbone derived from successive condensation of eight $C_5$ isoprene units (IPP). In addition, novel carotenoids with longer or shorter backbones occur in some species of nonphotosynthetic bacteria. Carotenoids may be acyclic, monocyclic, or bicyclic depending on whether the ends of the hydrocarbon backbones have been cyclized to yield aliphatic or cyclic ring structures (G. Armstrong, (1999) *In Comprehensive Natural Products Chemistry*, Elsevier Press, volume 2, pp 321–352).

Carotenoid biosynthesis starts with the isoprenoid pathway to generate the C5 isoprene unit, isopentenyl pyrophosphate (IPP). IPP is then condensed with its isomer dimethylallyl pyrophosphate (DMAPP) to generate the C10 geranyl pyrophosphate (GPP) which is then elongated to form the C15 farnesyl pyrophosphate (FPP). FPP synthesis is common in both carotenogenic and non-carotenogenic bacteria. Additional enzymes in the carotenoid pathway are able to then generate carotenoid pigments from the FPP precursor, segregating into two categories: (i) carotene backbone synthesis enzymes and (ii) subsequent modification enzymes. The backbone synthesis enzymes include geranyl geranyl pyrophosphate synthase, phytoene synthase, phytoene dehydrogenase and lycopene cyclase, etc. The modification enzymes include ketolases, hydroxylases, dehydratases, glycosylases, etc.

It is known that β-carotene can be converted to isorenieratene, an aromatic carotenoid, by a CrtU carotene desaturase. The crtU gene, encoding the carotene desaturase, has been identified in a few actinomycetes including *Streptomyces, Mycobacterium* and *Brevibacterium* (Krugel et al., *Biochimica et Biophysica Acta*, 1439: 57–64 (1999); Krubasik and Sandmann, *Mol Gen Genet* 263: 423–432 (2000); and Viveiros et al., *FEMS Microbiol Lett*, 187: 95–101 (2000)). Another aryl-carotene, chlorobactene, was reported in photosynthetic green bacteria (Liaaen-Jensen et al., *Acta Chem. Scand* 18: 1703–1718 (1964); Takaichi et al., *Arch Microbiol*, 168: 270–276 (1997)). Recent genomic sequencing of *Chlorobium tepidum* identified a putative carotene desaturase gene (Eisen et al., *PNAS USA*, 99: 9509–9514 (2002), which might be responsible for the synthesis of the native chlorobactene and derivatives. However, function of the putative carotene desaturase gene from *Chlorobium* has not yet been determined. It is likely that the CrtU from actinomycetes might also act on other substrates in addition to β-carotene to produce a variety of aryl-carotenoids, such as converting γ-carotene to chlorobactene.

Schumann et al. (*Mol Gen Genet*, 252: 658–666 (1996)) reported difficulty in attempting to express crtU in heterologous hosts. However, Lee et al. (*Chem Biol* 10(5): 453–462 (2003)) recently reported successful expression of the *Brevibacterium linens* crtU (DSMZ 20426) in *E. coli* using a pUC-derived expression vector. Lee et al. were able to detect the production of isorenieratene (in cells engineered to produce β-carotene) and didehydro-β-θ-carotene (in cells engineered to produce torulene). Lee et al. did not report the levels of aromatic carotenoids produced. It is likely the level was low since a low copy number pACYC-base plasmid was used to produce β-carotene precursor in a non-engineered *E. coli* host. Production of commercially-significant amounts of aryl carotenoids has not been reported in the literature.

Expressing genes from gram positive bacteria (with high G+C content) in *E. coli* is known to be often difficult. Low yields of protein in heterologous expression systems can been attributed to differences in codon usage. Difficulties in expressing heterologous genes in a host strain are generally due to an extremely rare codon used by host strain and correlates with low levels of its corresponding tRNA.

The inability to adequately express CrtU carotene desaturases in a gram-negative host for production of aryl carotenoids at commercially-useful levels presents a significant hurdle to the synthesis of a variety of aryl-carotenoids by genetic engineering. Furthermore, natural aryl-carotenoids are always present as mixtures of the aryl-carotenoid with their precursors or derivatives (Kohl et al., *Phytochemistry*, 22: 207–213 (1983); Takaichi et al., supra). Production of a pure aryl-carotenoid requires the ability to efficiently express the carotene desaturase in an industrially-useful heterologous host, such as *E. coli*.

The problem to be solved is to express a functional carotene desaturase (crtU) gene for the production of aryl-carotenoids in a gram-negative production host at commercially-significant concentrations. Applicants have solved the stated problem by isolating the crtU gene from *Brevibacterium linens* and expressing an optimized version of this gene in an *Escherichia coli* strain engineered to produce high levels of carotenoids.

SUMMARY OF THE INVENTION

The present invention provides methods for the expression of carotene desaturase genes and proteins in gram negative host cells for the conversion of cyclic carotenoids to the corresponding aryl compound. Accordingly the invention provides a method for the production of aryl carotenoid compounds comprising:

(a) providing a gram negative host cell which comprises a cyclic carotenoid having at least one β-ionone ring;

(b) transforming the gram negative host cell of (a) with a foreign gene encoding a carotene desaturase, said gene being codon optimized for expression in the gram negative host cell; and (c) growing the transformed gram negative host cell of (b) under conditions whereby an aryl carotenoid is produced.

In similar fashion the invention provides a method of regulating aryl carotenoid biosynthesis in an *E. coli* host comprising:

(a) introducing into an *E. coli* a carotene desaturase gene having the nucleic acid sequence selected from the group consisting of SEQ ID NO:18 and SEQ ID NO:53; and (b) growing the *E. coli* of (a) under conditions whereby the carotene desaturase gene is expressed and aryl carotenoid biosynthesis is regulated.

In a preferred embodiment the invention provides a method for the production of isorenieratene comprising:

(a) providing a gram negative host cell which comprises β-carotene;

(b) transforming the gram negative host cell of (a) with a gene encoding a carotene desaturase, said gene being codon optimized for expression in said gram negative host; and (c) growing the transformed gram negative host cell of (b) under conditions whereby an aryl carotenoid is produced.

In an alternate embodiment the invention provides a method for the production of chlorobactene comprising:

(a) providing a gram negative host cell which comprises γ-carotene;

(b) transforming the gram negative host cell of (a) with a gene encoding a carotene desaturase, said gene being codon optimized for expression in said gram negative host; and (c) growing the gram negative transformed host cell of (b) under conditions whereby chlorobactene is produced.

In an alternate embodiment the invention provides an *E. coli* codon optimized carotene desaturase gene selected from the group consisting of SEQ ID NO:18 and SEQ ID NO:53.

BRIEF DESCRIPTION OF THE DRAWINGS AND SEQUENCE DESCRIPTIONS

The patent or application file contains at least one drawing executed in color. Copies of this patent or patent application publication with color drawing(s) will be provided by the Office upon request and payment of the necessary fee.

Figure 6:
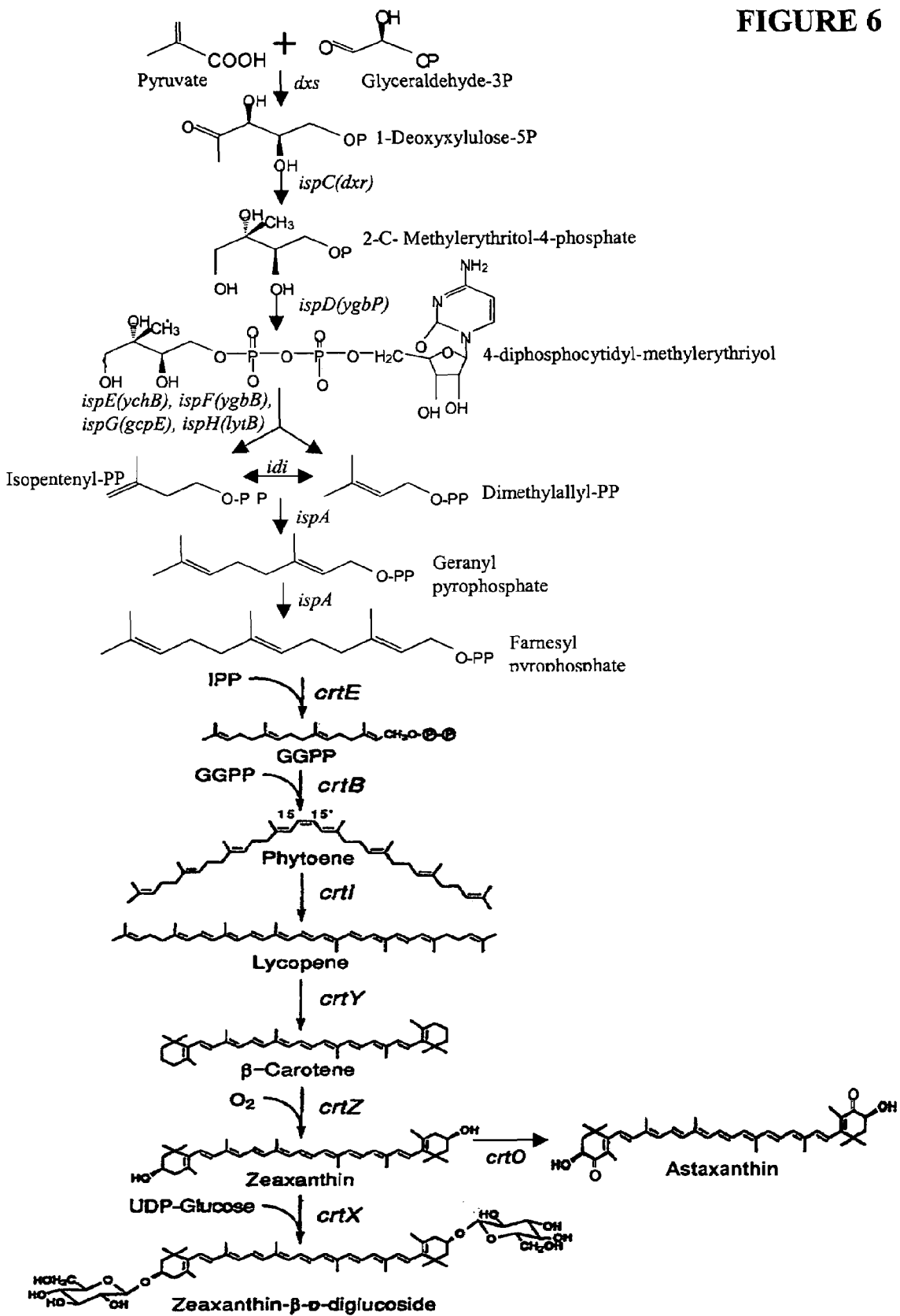

FIG. 6 diagrams the upper and lower carotenoid pathway.

The invention can be more fully understood from the following detailed description, biological deposits, and the accompanying sequence descriptions, which for a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

| Gene/Protein Product | Source | Nucleotide SEQ ID NO | Amino Acid SEQ ID NO |
|---|---|---|---|
| CrtE | *Pantoea stewartii* | 1 | 2 |
| CrtX | *Pantoea stewartii* | 3 | 4 |
| CrtY | *Pantoea stewartii* | 5 | 6 |
| CrtI | *Pantoea stewartii* | 7 | 8 |
| CrtB | *Pantoea stewartii* | 9 | 10 |
| CrtZ | *Pantoea stewartii* | 11 | 12 |

SEQ ID NOs:13–14 are oligonucleotide primers used to amplify the carotenoid biosynthetic gene cluster from *Pantoea stewartii*.

SEQ ID NO:15 is the nucleotide sequence of crtU gene (GenBank® Accession number AF139916) from *Brevibacterium linens* ATCC 9175.

SEQ ID NOs:16–17 are oligonucleotide primers used to amplify the optimized crtU product from *B. linens*.

SEQ ID NO:18 is the predicted nucleotide sequence of the codon optimized crtU gene, created for expression in *E. coli*.

SEQ ID NO:19 is the deduced amino acid sequence of SEQ ID NO:18.

SEQ ID NOs:20–27 are oligonucleotide primers used to create chromosomal integrations of a strong promoter upstream from isoprenoid genes in *E. coli*.

SEQ ID NOs:28–32 are oligonucleotide primers used to confirm integration of the T5 promoter in the *E. coli* chromosome.

SEQ ID NOs:33–36 are oligonucleotide primers used to amplify crtE for chromosomal integration.

SEQ ID NOs:37–38 are oligonucleotide primers used to confirm chromosomal integration of crtE.

SEQ ID NOs:39–41 are oligonucleotide primers used to amplify crtIB for chromosomal integration.

SEQ ID NOs:42–45 are oligonucleotide primers used to confirm chromosomal integration of crtIB.

SEQ ID NOs:46–48 are oligonucleotide primers used to confirm 16s identity of *Rhodococcus* AN12.

SEQ ID NO:49 is the nucleotide sequence for the crtL lycopene cyclase of *Rhodococcus* AN12.

SEQ ID NO:50 is the deduced amino acid sequence of SEQ ID NO:49.

SEQ ID NOs:51–52 are oligonucleotide primers used to amplify crtL of *Rhodococcus* AN12.

SEQ ID NO:53 is the nucleotide sequence for codon optimized crtU gene for expression in *E. coli* as amplified by PCR.

SEQ ID NO:54 is the nucleotide sequence for plasmid pPCB15.

SEQ ID NO:55 is the nucleotide sequence for plasmid pKD46.

SEQ ID NO:56 is the nucleotide sequence for plasmid pSUH5.

SEQ ID NO:57 is the nucleotide sequence for the $P_{T5}$ promoter.

BRIEF DESCRIPTION OF BIOLOGICAL DEPOSITS

Applicants have made the following biological deposits under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| Plasmid pCP20 | ATCC# PTA-4455 | Jun. 13, 2002 |
| E. coli strain DPR676: MG1655 P$_{T5}$-dxs, P$_{T5}$-idi pTrcHis2-TOPO-crtU (ampR), pBHR-crt+ (kanR) | ATCC# PTA-5136 | Apr. 11, 2003 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present invention provides a method for the conversion of cyclic carotenoids having a β-ionone ring to the corresponding aryl carotenoid, via the heterologous expression of a codon optimized carotene desaturase gene (crtU), in gram negative bacteria.

The expression of crtU in a heterologous host is useful for the selective production of aryl carotenoids, as well as for the regulation and production of other carotenoids in the isoprenoid biosynthetic pathway. There is a general practical utility for microbial isoprenoid production since carotenoid compounds are very difficult to make chemically (Nelis and Leenheer, *Appl. Bacteriol.*, 70:181–191 (1991)). Introduction of the aromatic ring(s) by expression of crtU will likely render the carotenoids more stable, which is desired for certain applications such as food colorants. For example, aromatic carotenoids, in particular dihydroxyisorenieratene, are used in dairy applications for coloring various cheeses and yellow carotenoids are particularly useful for the poultry industry, resulting in a deep yellow color to egg yolks and the skins chickens.

In this disclosure, a number of terms and abbreviations are used for the interpretation of the Claims and the specification.

"Open reading frame" is abbreviated ORF.

"Polymerase chain reaction" is abbreviated PCR.

"Isopropyl-beta-D-thiogalactoside" is abbreviated IPTG.

Within the present disclosure, names of genes will be in italics whereas the corresponding encoded protein will be in standard font. For example the genes crtU, crtE, crtY, crtI, crtB, crtZ, dxs, idi, ispD(ygbP), and ispF(ygbB) will encode polypeptides named CrtU, CrtE, CrtY, CrtI, CrtB, CrtZ, Dxs, Idi, IspD(YgbP), and IspF(YgbB), respectively.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "isoprenoid" or "terpenoid" refers to the compounds are any molecule derived from the isoprenoid pathway including 10 carbon terpenoids and their derivatives, such as carotenoids and xanthophylls.

The term "carotenoid" refers to a class of hydrocarbons having a conjugated polyene carbon skeleton formally derived from isoprene. This class of molecules is composed of $C_{30}$ diapocarotenoids and $C_{40}$ carotenoids and their oxygenated derivatives; and, these molecules typically have strong light absorbing properties. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids having at least one β-ionone ring capable of desaturation to form an aryl carotenoid. Suitable carotenoids typically include $C_{30}$ and $C_{40}$ carotenoids; however any carotenoid having a β-ionone ring capable of being desaturated would be suitable in the present invention. "Asymmetric carotenoids" refers to monocyclic carotenoids. Examples of asymmetric carotenoids include γ,ψ-carotene, ε,ψ-carotene, β,ψ-carotene, or φ,ψ-carotene (chlorobactene) as well as retinal, retinol, 14'-apo-β-caroten-14', 12', 10', 8', 6', 4', or 2'-al or -ol. Torulene, torularhodinaldehyde, torularhodin, torularhodinol, and torularhodin methyl ester are also examples. "$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure (hereinafter referred to as "diapophytoene"), having a long central chain of conjugated double bonds, by: (i) hydrogenation (ii) dehydrogenation, (iii) cyclization, (iv) oxidation, (v) esterification/glycosylation, or any combination of these processes.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure. Non-limiting examples of $C_{40}$ carotenoids include: phytoene, lycopene, β-carotene, zeaxanthin, astaxanthin, and canthaxanthin.

The term "carotenoid biosynthetic pathway" refers to those genes comprising members of the upper isoprenoid pathway and/or lower carotenoid biosynthetic pathway.

The terms "upper isoprenoid pathway" and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthasey; the "ispC" gene (encoding 1-deoxyxylulose-5-phosphate reductoisomerase; also known as dxr); the "ispD" gene (encoding a 2C-methyl-D-erythritol cytidyltransferase enzyme; also known as ygbp); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTPsynthase); the "ispG" gene (encoding a enzyme that is involved in conversion of 2C-methyl-D-erythritol-2,4-cyclodiphosphate to 1-hydroxy-2-methyl-2-(E)-butenyl 4-diphosphate; also known as gcpE); the "ispH" gene (encoding a enzyme that is involved in is involved in conversion of 1-hydroxy-2-methyl-2-(E)-butenyl 4-diphosphate to isopentenyl diphosphate (IPP) and dimethylallyl diphosphate (DMAPP); also known as lytB); the "idi" gene (responsible for the intramolecular conversion of IPP to dimethylallyl pyrophosphate); and the "ispA" gene (encoding geranyltransferase or farnesyl diphosphate synthase) in the isoprenoid pathway.

The terms "lower carotenoid biosynthetic pathway" and "lower pathway" will be used interchangeably and refer to those enzymes which convert FPP to a suite of carotenoids. These include those genes and gene products that are involved in the immediate synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$–$C_{40}$ carotenoids are included within the lower carotenoid biosynthetic pathway. These genes and gene products comprise all of the "crf" genes including, but not limited to: crtM, crtN, crtN2, crtE, crtX, crtY, crtI, crtB, crtZ, crtW, crtO, crtA, crtC, crtD, crtF, and crtU. Finally, the term "lower carotenoid biosynthetic enzyme" is an inclusive term referring to any and all of the enzymes in the present lower pathway including, but not limited to: CrtM, CrtN, CrtN2, CrtE, CrtX, CrtY, CrtI, CrtB, CrtZ, CrtW, CrtO, CrtA, CrtC, CrtD, CrtF, and CrtU.

The term "cyclic carotenoid" refers to a carotenoid having at least one β-ionone ring. The terms "β-ionone ring" and "β-ionone group" are defined as the $C_9H_{15}$ shown as the boxed cyclic structure in γ-carotene or β-carotene (FIG. 1).

Figure 1:
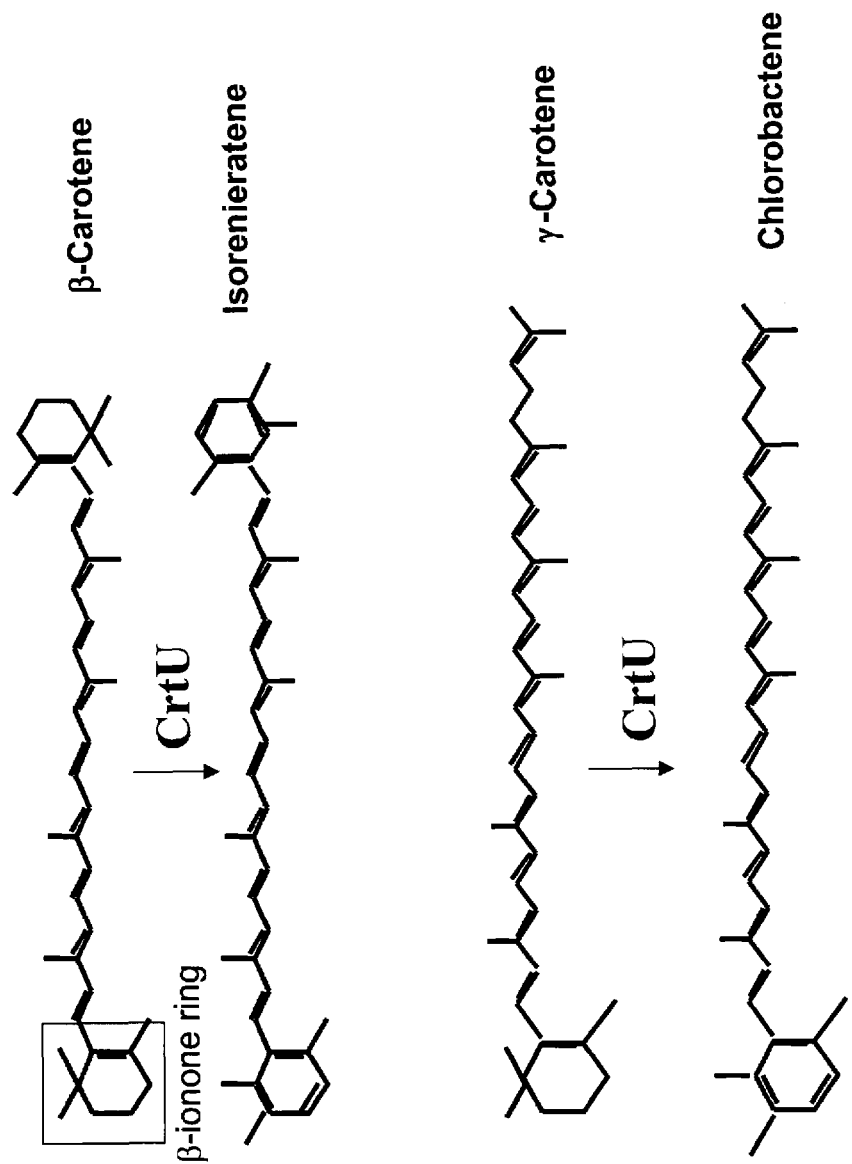
FIG. 1 shows the enzymatic aromatization of carotenoids by CrtU.

The term "aromatic carotenoid" or "aryl carotenoid" refers to $C_{30}$ and $C_{40}$ carotenoids with at least one aromatic end group, including but not limited to, isorenieratene, β-isorenieratene, chlorobactene, and derivatives thereof as shown in FIG. 1.

The term "lycopene cyclase" or "β-cyclase" are used interchangeably and refer to an enzyme that catalyzes the formation of a β-ionone ring cyclic end group from the acyclic ψ-end group. Lycopene cyclases normally form the bicyclic carotenoid (i.e. β-carotene) from substrates having two ψ-end groups (i.e. lycopene). Lycopene cyclases have been reported that selectively convert only one of two ψ-end groups, forming monocyclic carotenoids (U.S. Ser. No. 10/292577) such as γ-carotene.

The term "*Pantoea stewartii*" is abbreviated as "*P. stewartii*" and is used interchangeably with *Erwinia stewartii* (Mergaert et al., *Int. J. Syst. Bacteriol.*, 43:162–173 (1993)), and refers to ATCC strain number 8199.

The term "*Brevibacterium linens*" is abbreviated "*B. linens*" and refers to ATCC strain number 9175.

The terms "*Rhodococcus erythropolis* AN12" or "AN12" will be used interchangeably and refer to the *Rhodococcus erythropolis* AN12 strain.

The term "dxs" refers to the enzyme D-1-deoxyxylulose 5-phosphate encoded by the *E.coli* dxs gene that catalyzes the condensation of pyruvate and D-glyceraldehyde 3-phosphate to D-1-deoxyxylulose 5-phosphate (DOXP).

The term "idi" refers to the enzyme isopentenyl diphosphate isomerase encoded by the *E.coli* idi gene that converts isopentenyl diphosphate to dimethylallyl diphosphate.

The term "YgbP" or "IspD" and refers to the enzyme encoded by the ygbB or ispD gene that catalyzes the CTP-dependent cytidylation of 2–C-methyl-D-erythritol-4-phosphate to 4-diphosphocytidyl-2C-methyl-D-erythritol. The names of the gene, ygbP or ispD, are used interchangeably in this application. The names of gene product, YgbP or IspD are used interchangeably in this application.

The term "YgbB" or "IspF" refers to the enzyme encoded by the ybgB or ispF gene that catalyzes the cyclization with loss of CMP of 4-diphosphocytidyl-2C-methyl-D-erythritol to 4-diphosphocytidyl-2C-methyl-D-erythritol-2-phosphate to 2C-methyl-D-erythritol-2,4-cyclodiphosphate. The names of the gene, ygbB or ispF, are used interchangeably in this application. The names of gene product, YgbB or IspF are used interchangeably in this application.

The term "ygbBP" refers to the two genes ygbB and ygbP. The term "CrtE" refers to geranylgeranyl pyrophosphate synthase enzyme encoded by crtE gene represented in SEQ ID NO:1, which converts trans-trans-farnesyl diphosphate+isopentenyl diphosphate to pyrophosphate+geranylgeranyl diphosphate The term "CrtY" refers to lycopene cyclase enzyme encoded by crtY gene represented in SEQ ID NO:5, which converts lycopene to beta-carotene.

The term "CrtI" refers to phytoene dehydrogenase enzyme encoded by crtI gene represented in SEQ ID NO:7, which converts phytoene into lycopene via the intermediaries of phytofluene, zeta-carotene, and neurosporene by the introduction of 4 double bonds The term "CrtB" refers to phytoene synthase enzyme encoded by crtB gene represented in SEQ ID NO:9, which catalyses reaction from prephytoene diphosphate to phytoene.

The term "carotene desaturase" refers to the group of enzymes that can desaturate and transfer methyl or other groups of the β-ionone ring of mono- or bi-cyclic carotenoids. The term "CrtU" refers to a carotene desaturase which can convert a carotenoid comprised of at least one β-ionone ring to an aryl carotenoid. In the present invention, a codon optimized crtU gene was expressed in a heterologous host, converting β-carotene or γ-carotene to the arylcarotenes isorenieratene and chlorobactene, respectively.

The term "CrtZ" refers to a β-carotene hydroxylase enzyme encoded by crtZ gene represented in SEQ ID NO:11, which catalyses hydroxylation reaction from β-carotene to zeaxanthin. The CrtZ gene product also has the ability to convert canthaxanthin to astaxanthin. The term "pKD46" refers to the plasmid constructed by Datsenko and Wanner (*PNAS*, 97:6640–6645 (2000); SEQ ID NO:55).

Figure 5:
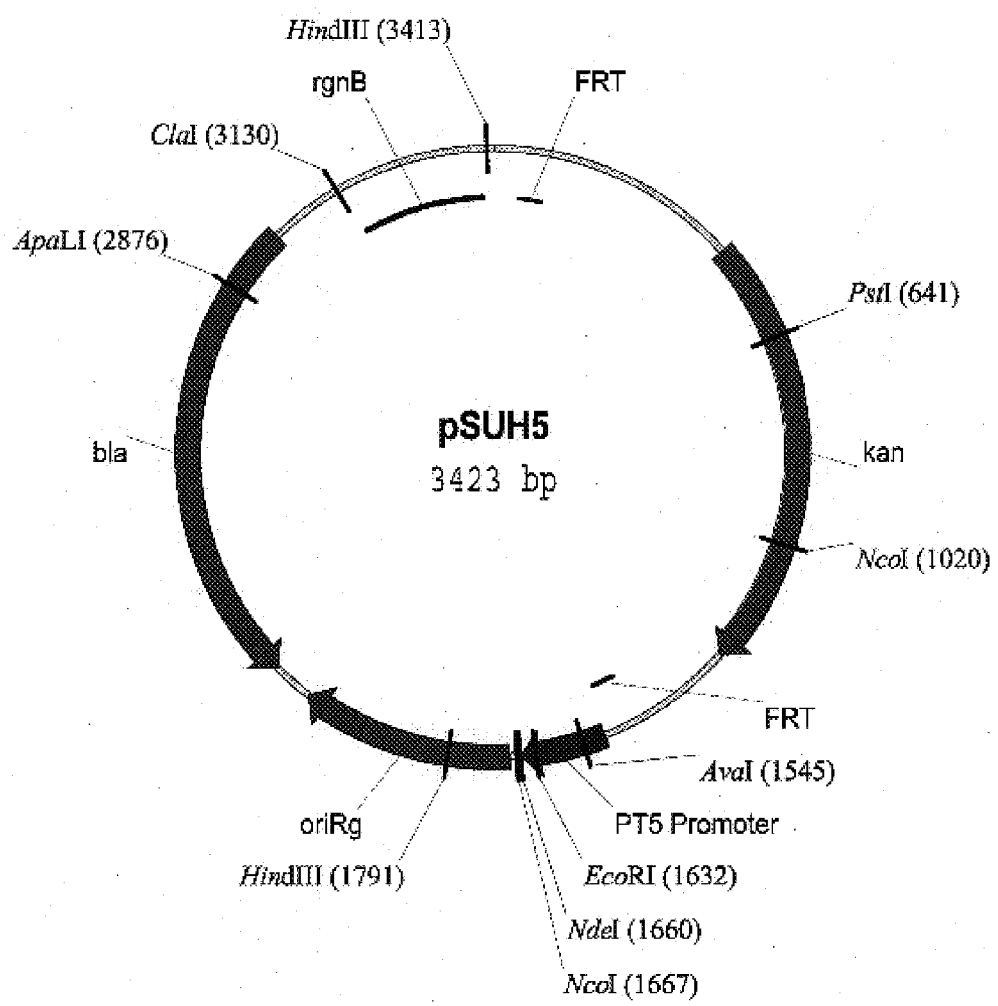
FIG. 5 shows plasmid pSUH5, used for the preparation of the PCR DNA fragment having a fused antibiotic selection marker and phage T5 promoter (kan-$P_{T5}$).

The term "pSUH5" refers to the plasmid that was constructed in this invention by cloning a phage T5 promoter ($P_{T5}$) region into the NdeI restriction endonuclease site of pKD4 (Datsenko and Wanner, supra). pSUH5 was used as a template plasmid for PCR amplification of a fused kanamycin selectable marker/phage T5 promoter linear DNA fragment (FIG. 5; SEQ ID NO:56).

The terms "$P_{T5}$ promoter" and "T5 promoter" refer to the nucleotide sequence that comprises the −10 and −35 consensus sequences, lactose operator (lacO), and ribosomal binding site (rbs) from phage T5 (SEQ ID NO:57).

The term "helper plasmid" refers to either pKD46 encoding λ-Red recombinase or pCP20 (ATCC PTA-4455) encoding FLP site specific recombinase (Datsenko and Wanner, supra).

The terms "λ-Red recombinase system", "λ-Red system", and "λ-Red recombinase" are used interchangeably and refer to three essential genes, exo, bet, and gam, that are contained on a helper plasmid, pKD46 (Datsenko and Wanner, supra).

The term "homology arm" refers to a nucleotide sequence which enables homologous recombination between two nucleic acids having substantially the same nucleotide sequence in a particular region of two different nucleic acids. The preferred size range of the nucleotide sequence of the homology arm is from about 10 to about 50 nucleotides.

The term "triple homologous recombination" in the present invention refers to a genetic recombination between two linear DNA nucleotides and the target chromosome via their homologous sequences resulting in chromosomal integration of two linear nucleotides into the target of chromosome.

The term "site-specific recombinase" is used in the present invention to describe a system comprised of one or more enzymes which recognize specific nucleotide sequences (recombination target sites) and which catalyze recombination between the recombination target sites. Site-specific recombination provides a method to rearrange, delete, or introduce exogenous DNA. Examples of site-specific recombinases and their associated recombination target sites are flippase (FLP/FRT), Cre-lox, R/RS, Gin/gix, Xer/dif, and InVatt. In the present invention the Applicants illustrate the use of a site-specific recombinase to remove selectable markers. Antibiotic resistance markers, flanked on both sides by FRT recombination target sites, are removed by expression of the FLP site-specific recombinase. This method is used so that the number of chromosomal modifications necessary for microbial pathway engineering is not limited to the number of available selection markers (Huang et al., *J. Bacteriol.*, 179(19): 6076–6083 (1997)).

The terms "transduction" and "general transduction" are used interchangeably and refer to a phenomenon in which bacterial DNA is transferred from one bacterial cell (the donor) to another (the recipient) by a phage particle containing bacterial DNA.

The terms "P1 donor cell" and "donor cell" are used interchangeably in the present invention and refer to a bacterial strain susceptible to infection by a bacteriophage or virus, and which serves as a source for the nucleic acid fragments packaged into the transducing particles. Typically, the genetic make up of the donor cell is similar or identical to the "recipient cell" which serves to receive P1 lysate containing transducing phage or virus produced by the donor cell.

The terms "P1 recipient cell" and "recipient cell" are used interchangeably in the present invention and refer to a bacterial strain susceptible to infection by a bacteriophage or virus and which serves to receive lysate containing transducing phage or virus produced by the donor cell.

The terms "stacking", "combinatorial stacking", "chromosomal stacking", and "trait stacking" are used interchangeably and refer to the repeated process of stacking multiple genetic traits into one *E. coli* host using the bacteriophage P1 in combination with the site-specific-recombinase system for removal of selection markers.

The terms "parallel combinatorial fashion" and "combinatorial fashion" are used interchangeably and refer to the P1 transduction with the P1 lysate mixture made from various donor cells, so that multiple genetic traits can move the recipient cell in parallel.

The terms "integration cassette" and "recombination element" refer to a linear nucleic acid construct useful for the transformation of a recombination proficient bacterial host. Recombination elements of the invention may include a variety of genetic elements such as selectable markers, functional DNA fragments, and recombination regions having homology to regions on a bacterial chromosome or other recombination elements. Functional DNA fragments can include promoters, coding sequences, genes, and other regulatory elements specifically engineered into the recombination element to impart a desired phenotypic change upon recombination.

"Operon", in bacterial DNA, is a cluster of contiguous genes transcribed from one promoter that gives rise to a polycistronic mRNA.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data. Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple sequence alignment can be performed using the Clustal method of alignment (Higgins and Sharp, *CABIOS.* 5:151–153 (1989)) with the default parameters (GAP PENALTY=10, GAP LENGTH PENALTY=10). Default parameters for pairwise alignments using the Clustal method are typically KTUPLE 1, GAP PENALTY=3, WINDOW=5, and DIAGONALS SAVED=5.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". "Inducible promoters" are promoters that are not always active the way constitutive promoters are (e.g. viral promoters). Some inducible promoters are activated by physical means, such as the heat shock promoter. Other inducible promoters are activated by chemicals such as isopropyl-β-thiogalactopyranoside (IPTG) or Tetracycline (Tet). It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. In the present invention, the genome of the host organism is comprised the genes found on the chromosome and extrachromosomal elements (i.e. plasmids). Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

In the present invention, the terms "commercially-significant", "commercially-suitable", and "industrially-suitable" are used interchangeably and refer to the in vivo production of at least 3 mg/L aryl carotenoid(s) in a heterologous production host (gram negative bacteria). In another embodiment, the gram negative bacteria is capable of producing at least 4 mg/L aryl carotenoid(s) in vivo.

The terms "codon optimized" or "gene optimized" refer to the modification at least one codon of the nucleotide sequence of a gene that does not modify the amino acid sequence encoded by the gene but results in increased expression levels by using codons corresponding to highly used tRNAs by the expression host.

The term "comprising" means the presence of the stated features, integers, steps, or components as referred to in the claims, but that it does not preclude the presence or addition of one or more other features, integers, steps, components or groups thereof.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984)(hereinafter "Silhavy"); and by Ausubel, F. M. et al., *Current Protocols in Molecular Biology*, published by Greene Publishing Assoc. and Wiley-Interscience (1987)(hereinafter "Ausubel").

The present invention provides a method for the in vivo biotransformation of cyclic carotenoids having at least one β-ionone ring to the corresponding aryl carotenoid. The method proceeds by a) providing a gram negative host cell capable of producing a cyclic carotenoid having at least one β-ionone ring, b) transforming the gram negative host cell with a foreign crtU gene codon optimized for expression in the gram negative host cell, and c) growing the transformed gram negative host cell under conditions where aryl carotenoid is produced.

Carotene Desaturase Activity

Biosynthesis of aromatic carotenoids catalyzed by CrtU proceeds by desaturation and methyltransferation on the β-ionone ring of the cyclic carotenoids (Krugel et al., supra). CrtU, expressed in its native host has been shown to convert β-carotene with two β-ionone rings, to aromatic groups of isorenieratene in *Streptomyces griseus, Brevibacterium linens*, and *Mycobacterium auraum* A+ (Krugel et al., supra; Krubasik and Sandmann, *Mol Gen Genet*, 263:423–432 (2000); Viveiros et al., supra).

A number of carotene desaturases are known and will be suitable in the present invention. For example, carotene desaturase has been identified in *Streptomyces avermitilis* (GenBank® Accession No. AB070934) *Streptomyces griseus*, (GenBank® Accession No. AF272737), *Mycobacterium aurum*, (GenBank® Accession No. AJ133724), *Brevibacterium linens* (GenBank® Accession No. AF139916), and *Streptomyces coelicolor* (GenBank® Accession No. AL158057), where the carotene desaturase isolated from *Brevibacterium linens* as described by the native and optimized sequences of crtU (SEQ ID NOs:15, 18, and 53) are preferred.

One of the objects of the present invention is to increase the level of expression of a carotene desaturase gene in gram negative bacteria to effect commercially-significant levels of conversion of cyclic carotenoids to the corresponding aryl-carotenoid. One potential method for increasing expression levels is to optimize the genes for expression in the specific host. In a further embodiment, the host cell can be engineered to produce elevated levels of suitable carotenoid substrates for desaturation by a carotenoid desaturase (CrtU).

Low-yields of protein in heterologous expression systems have been attributed to differences in codon usage. Difficulties in expressing heterologous genes in host strain are generally due to an extremely rare codon used by host strain and correlates with low levels of its corresponding tRNA (Apeler et al., *European Journal of Biochemistry*, 247: 890–895 (1997); Deng, T. L., *FEBS Letters*, 409: 269–272 (1997)). For example, *E. coli* may lack the translational machinery needed to efficiently produce proteins from the genes of gram positive bacteria that have a high content of G+C nucleotides of 65 to 70% in their DNA. Sanli et al. (US 2002146731) improved expression in *E. coli* by reducing the high G+C content of codons for leucine, proline, alanine, arginine, glutamate, glycine, and valine. Sampson et al. (*Protein Expression and Purification*, 12(3):347–352 (1998)) improved expression of *Brevibacterium sterolicum* cholesterol oxidase in *E. coli* by modifying the first 21 amino acids with high-expression *E. coli* codons. These changes resulted in a 60-fold improvement of expression level.

The present invention relates to *Brevibacterium linens* crtU gene that was codon optimized for expression in a gram negative host cell (i.e. optimized for *E. coli* codon bias), and showed functional expression in *E. coli*. In this invention, PCR-based method was used to replace low-usage codons of crtU gene with high-usage codons in *E. coli*. Codon optimized PCR primers were designed to optimize the 5 low-usage codons of the N-terminal coding region and the 9 low-usage codons of the C-terminal coding region of crtU, and used to amplify native crtU gene from *Brevibacterium linens*.

Production of Desaturase Substrates

The present invention requires a source of substrate for the carotene desaturase. Suitable substrates are cyclic carotenoid compounds comprising a β-ionone ring. In particular, suitable substrates include, but are not limited to, β-carotene; γ-carotene; α-carotene; zeaxanthin; β-isorenieratene (φ,β-carotene); torulene; 1',2'-dihydro-γ-carotene; 7,8-dihydro-γ-carotene; 7',8'-dihydro-β-carotene; 7',8',7,8-tetrahydro-β-carotene; β-zeacarotene; echinenone; 3-OH-β-carotene; 1',2'-dihydro-1'-OH-torulene; 16'-OH-torulene; 16'-oxo-torulene; and 16'-carboxy-torulene.

Typical aryl carotenoids that will be produced by the aromatization of the β-ionone ring on the cyclic carotenoid will include, but are not limited to, isorenieratene (φ,φ-carotene); chlorobactene (φ,ψ-carotene); β-isorenieratene (φ,β-carotene); didehydro-φ, β-carotene, φ,ε-carotene; 1,2-didehydrochlorobactene; 1',2'-dihydrochlorobactene; 7,8-dihydro-chlorobactene; 7' 8'-dihydro-isorenieratene; 7',8',7,8-tetrahydro-isorenieratene; 7' 8'-dihydro-chlorobactene; β,φ-carotene-4-one; β,φ carotene-3-ol; 3-OH-isorenieratene; 3,3'-dihydroxy-isorenieratene; 7',8'-didehydrorenieratene; OH-chlorobactene; 1',2'-dihydro-1'-OH-didehydrochlorobactene; 16'-OH-didehydrochlorobactene; 16'-oxo-didehydrochlorobactene; and 16'-carboxy-didehydrochlorobactene.

Desaturase substrates may be provided exogenously to the cells or may be produced endogenously by the cells. In the case of the latter it may be necessary to introduce additional genes for the production of various cyclic carotenoid substrates which will be drawn from the genes of the upper and/or lower carotenoid pathway.

Genes Involved in Carotenoid Production.

The enzyme pathway involved in the biosynthesis of carotenoids can be conveniently viewed in two parts, the upper isoprenoid pathway providing for the conversion of pyruvate and glyceraldehyde-3-phosphate to isopentenyl pyrophosphate and the lower carotenoid biosynthetic pathway, which provides for the synthesis of phytoene and all subsequently produced carotenoids. The upper and lower pathways are diagramed in FIG. 6. The upper pathway is ubiquitous in most gram negative bacteria and in these cases it will only be necessary to introduce genes that comprise the lower pathway for the biosynthesis of the desired carotenoid. The key division between the two pathways concerns the synthesis of farnesyl pyrophosphate (FPP). Where FPP is naturally present only elements of the lower carotenoid pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Each of these pathways will be discussed below in detail.

The Upper Isoprenoid Pathway

IPP biosynthesis occurs through either of two pathways. First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.* 111:135–140 (1993); Rohmer et al, *Biochem.* 295: 517–524 (1993); Schwender et al., *Biochem.* 316: 73–80 (1996); Eisenreich et al., *Proc. Natl. Acad. Sci. USA* 93: 6431–6436 (1996)). Many steps in both isoprenoid pathways are known (FIG. 1). For example, the initial steps of the alternate pathway leading to the production of IPP have been studied in *Mycobacterium tuberculosis* by Cole et al. (*Nature* 393:537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP (Cole et al., supra). Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). Finally, the product of ygbB gene converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663). It is known that 2C-methyl-D-erythritol 2,4-cyclodiphosphate can be further converted into IPP to ultimately produce carotenoids in the carotenoid biosynthesis pathway. However, the reactions leading to the production of isopentenyl monophosphate from 2C-methyl-D-erythritol 2,4-cyclodiphosphate are not yet well-characterized. Several additional genes (and perhaps others) including "pyrG" (encoding a CTP synthase), "lytB" is (involved in the formation of dimethylallyl diphosphate), and "gcpE" (involved in the synthesis of 2-C-methyl-D-erythritol 4-phosphate) are thought to participate in the reactions leading to formation of isopentenyl pyrophosphate (IPP) and dimethylallyl pyrophosphate (DMAPP).

IPP may be isomerized to DMAPP via IPP isomerase, encoded by the idi gene, however this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate. This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

Genes encoding elements of the upper pathway are known from a variety of plant, animal, and bacterial sources, as shown in Table 1.

TABLE 1

Sources of Genes Encoding the Upper Isoprenoid Pathway

| Gene | GenBank Accession Number and Source Organism |
|---|---|
| dxs (D-1-deoxyxylulose 5-phosphate synthase) | AF035440, *Escherichia coli* |
| | Y18874, *Synechococcus* PCC6301 |
| | AB026631, *Streptomyces* sp. CL190 |
| | AB042821, *Streptomyces griseolosporeus* |
| | AF111814, *Plasmodium falciparum* |
| | AF143812, *Lycopersicon esculentum* |
| | AJ279019, *Narcissus pseudonarcissus* |
| | AJ291721, *Nicotiana tabacum* |

TABLE 1-continued

Sources of Genes Encoding the Upper Isoprenoid Pathway

| Gene | GenBank Accession Number and Source Organism |
|---|---|
| ispC(dxr) (1-deoxy-D-xylulose 5-phosphate reductoisomerase) | AB013300, *Escherichia coli*<br>AB049187, *Streptomyces griseolosporeus*<br>AF111813, *Plasmodium falciparum*<br>AF116825, *Mentha x piperita*<br>AF148852, *Arabidopsis thaliana*<br>AF182287, *Artemisia annua*<br>AF250235, *Catharanthus roseus*<br>AF282879, *Pseudomonas aeruginosa*<br>AJ242588, *Arabidopsis thaliana*<br>AJ250714, *Zymomonas mobilis* strain ZM4<br>AJ292312, *Klebsiella pneumoniae*,<br>AJ297566, *Zea mays* |
| ispD(ygbP) (2-C-methyl-D-erythritol 4-phosphate cytidylyltransferase) | AB037876, *Arabidopsis thaliana*<br>AF109075, *Clostridium difficile*<br>AF230736, *Escherichia coli*<br>AF230737, *Arabidopsis thaliana* |
| ispE(ychB) (4-diphosphocytidyl-2-C-methyl-D-erythritol kinase) | AF216300, *Escherichia coli*<br>AF263101, *Lycopersicon esculentum*<br>AF288615, *Arabidopsis thaliana* |
| ispF(ygbB) (2-C-methyl-D-erythritol 2,4-cyclodiphosphate synthase) | AB038256, *Escherichia coli* mecs gene<br>AF230738, *Escherichia coli*<br>AF250236, *Catharanthus roseus* (MECS)<br>AF279661, *Plasmodium falciparum*<br>AF321531, *Arabidopsis thaliana* |
| ispG(gcpE) (1-hydroxy-2-methyl-2-(E)-butenyl 4-diphosphate synthase) | O67496, *Aquifex aeolicus*<br>P54482, *Bacillus subtilis*<br>Q9pky3, *Chlamydia muridarum*<br>Q9Z8H0, *Chlamydophila pneumoniae*<br>O84060, *Chlamydia trachomatis*<br>P27433, *Escherichia coli*<br>P44667, *Haemophilus influenzae*<br>Q9ZLL0, *Helicobacter pylori* J99<br>O33350, *Mycobacterium tuberculosis*<br>S77159, *Synechocystis* sp.<br>Q9WZZ3, *Thermotoga maritima*<br>O83460, *Treponema pallidum*<br>Q9JZ40, *Neisseria meningitidis*<br>Q9PPM1, *Campylobacter jejuni*<br>Q9RXC9, *Deinococcus radiodurans*<br>AAG07190, *Pseudomonas aeruginosa*<br>Q9KTX1, *Vibrio cholerae* |
| pyrG (CTP synthase) | AB017705, *Aspergillus oryzae*<br>AB064659, *Aspergillus kawachii*<br>AF061753, *Nitrosomonas europaea*<br>AF206163, *Solorina crocea*<br>L22971, *Spiroplasma citri*<br>M12843, *E. coli*<br>M19132, *Emericella nidulans*<br>M69112, *Mucor circinelloides*<br>U15192, *Chlamydia trachomatis*<br>U59237, *Synechococcus* PCC7942<br>U88301, *Mycobacterium bovis*<br>X06626, *Aspergillus niger*<br>X08037, *Penicillium chrysogenum*<br>X53601, *P. blakesleeanus*<br>X67216, *A. brasilense*<br>Y11303, *A. fumigatus*<br>Y13811, *Aspergillus oryzae*<br>NM_001905,<br>*Homo sapiens* CTP synthase (CTPS), mRNA<br>NM_016748, *Mus musculus* cytidine 5'-triphosphate synthase (Ctps), mRNA<br>NM_019857<br>*Homo sapiens* CTP synthase II (CTPS2),<br>X68196<br>mRNA *S. cerevisiae* ura8 gene for CTP synthetase<br>XM_013134<br>BC009408, *Homo sapiens*, CTP synthase, clone MGC10396 IMAGE 3355881<br>*Homo sapiens* CTP synthase II (CTPS2), mRNA<br>XM_046801<br>*Homo sapiens* CTP synthase II (CTPS2), mRNA<br>XM_046802<br>*Homo sapiens* CTP synthase II (CTPS2), mRNA |

TABLE 1-continued

Sources of Genes Encoding the Upper Isoprenoid Pathway

| Gene | GenBank Accession Number and Source Organism |
| --- | --- |
| | XM_046803<br>*Homo sapiens* CTP synthase II (CTPS2), mRNA<br>XM_046804<br>*Homo sapiens* CTP synthase II (CTPS2), mRNA<br>Z47198, *A. parasiticus* pksA gene for polyketide synthase |
| ispH(lytB) | AF027189, *Acinetobacter* sp. BD413<br>AF098521, *Burkholderia pseudomallei*<br>AF291696, *Streptococcus pneumoniae*<br>AF323927, *Plasmodium falciparum* gene<br>M87645, *Bacillus subtillis*<br>U38915, *Synechocystis* sp.<br>X89371, *C. jejuni* sp O67496 |
| IspA (FPP synthase) | AB003187, *Micrococcus luteus*<br>AB016094, *Synechococcus elongatus*<br>AB021747, *Oryza sativa* FPPS1 gene for farnesyl diphosphate synthase<br>AB028044, *Rhodobacter sphaeroides*<br>AB028046, *Rhodobacter capsulatus*<br>AB028047, *Rhodovulum sulfidophilum*<br>AF112881 and AF136602, *Artemisia annua*<br>AF384040, *Mentha x piperita*<br>D00694, *Escherichia coli*<br>D13293, *B. stearothermophilus*<br>D85317, *Oryza sativa*<br>X75789, *A. thaliana*<br>Y12072, *G. arboreum*<br>Z49786, *H. brasiliensis*<br>U80605, *Arabidopsis thaliana* farnesyl diphosphate synthase precursor (FPS1) mRNA, complete cds<br>X76026, *K. lactis* FPS gene for farnesyl diphosphate synthetase, QCR8 gene for bc1 complex, subunit VIII<br>X82542, *P. argentatum* mRNA for farnesyl diphosphate synthase (FPS1)<br>X82543, *P. argentatum* mRNA for farnesyl diphosphate synthase (FPS2)<br>BC010004, *Homo sapiens*, farnesyl diphosphate synthase (farnesyl pyrophosphate synthetase, dimethylallyltranstransferase, geranyltranstransferase), clone MGC 15352 IMAGE, 4132071, mRNA, complete cds<br>AF234168, *Dictyostelium discoideum* farnesyl diphosphate synthase (Dfps)<br>L46349, *Arabidopsis thaliana* farnesyl diphosphate synthase (FPS2) mRNA, complete cds<br>L46350, *Arabidopsis thaliana* farnesyl diphosphate synthase (FPS2) gene, complete cds<br>L46367, *Arabidopsis thaliana* farnesyl diphosphate synthase (FPS1) gene, alternative products, complete cds<br>M89945, Rat farnesyl diphosphate synthase gene, exons 1–8<br>NM_002004, *Homo sapiens* farnesyl diphosphate synthase (farnesyl pyrophosphate synthetase, dimethylallyltranstransferase, geranyltranstransferase) (FDPS), mRNA<br>U36376, *Artemisia annua* farnesyl diphosphate synthase (fps1) mRNA, complete cds<br>XM_001352, *Homo sapiens* farnesyl diphosphate synthase (farnesyl pyrophosphate synthetase, dimethylallyltranstransferase, geranyltranstransferase) (FDPS), mRNA<br>XM_034497, *Homo sapiens* farnesyl diphosphate synthase (farnesyl pyrophosphate synthetase, dimethylallyltranstransferase, geranyltranstransferase) (FDPS), mRNA<br>XM_034498, *Homo sapiens* farnesyl diphosphate synthase (farnesyl pyrophosphate synthetase, dimethylallyltranstransferase, geranyltranstransferase) (FDPS), mRNA<br>XM_034499, *Homo sapiens* farnesyl diphosphate synthase (farnesyl pyrophosphate synthetase, dimethylallyltranstransferase, geranyltranstransferase) (FDPS), mRNA<br>XM_0345002, *Homo sapiens* farnesyl diphosphate synthase (farnesyl pyrophosphate synthetase, dimethylallyltranstransferase, geranyltranstransferase) (FDPS), mRNA |

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the first step in the lower carotenoid biosynthetic pathway is considered to begin with the prenyltransferase reaction converting farnesyl pyrophosphate (FPP) to geranylgeranyl pyrophosphate (GGPP). The gene ciE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase. In addition to $C_{40}$ carotenoid biosynthesis, some microorganisms are able to make $C_{30}$ carotenoids (U.S. Pat. No. 6,660,507, U.S. Ser. No. 09/941947; hereby incorporated by reference). Several genes, including crtN1, crN2, crN3, and ald encode enzymes involved in the conversion of farnesyl pyrophosphate (FPP) to $C_{30}$ carotenoids.

Lycopene, which imparts a "red"-colored spectra, is produced from phytoene through four sequential dehydrogenation reactions by the removal of eight atoms of hydrogen, catalyzed by the gene crtI (encoding phytoene desaturase). Intermediaries in this reaction are phytofluene, zeta-carotene, and neurosporene. Lycopene cyclase (crtY) converts lycopene to β-carotene.

β-carotene is converted to zeaxanthin via a hydroxylation reaction resulting from the activity of β-carotene hydroxylase (encoded by the crtZ gene). β-cryptoxanthin is an intermediate in this reaction.

β-carotene can be converted to canthaxanthin by a carotene ketolase encoded by one of the crtW, bkt, or crO genes. Echinenone in an intermediate in this reaction. Canthaxanthin can then be converted to astaxanthin by β-carotene hydroxylase encoded by the crtZ gene. Adonbirubrin is an intermediate in this reaction. Zeaxanthin can be converted to astaxanthin by a carotene ketolase encoded by one of the crtW, bkt, or crO genes. Adonixanthin is an intermediate in this reaction.

Zeaxanthin can be converted to zeaxanthin-β-diglucoside. This reaction is catalyzed by zeaxanthin glucosyl transferase (crtX). Spheroidene can be converted to spheroidenone by spheroidene monooxygenase encoded by crtA.

Neurosporene can be converted spheroidene and lycopene can be converted to spirilloxanthin by the sequential actions of hydroxyneurosporene synthase, methoxyneurosporene desaturase and hydroxyneurosporene-O-methyltransferase encoded by the crtC, crtD and crtF genes, respectively.

Examples of genes encoding elements of the lower carotenoid biosynthetic pathway are known from a variety of plant, animal, and bacterial sources, as shown in Table 2.

TABLE 2

Sources of Genes Encoding the Lower Carotenoid Biosynthetic Pathway

| Gene | GenBank Accession Number and Source Organism |
|---|---|
| crtE (GGPP Synthase) | AB000835, *Arabidopsis thaliana* |
| | AB016043 and AB019036, *Homo sapiens* |
| | AB016044, *Mus musculus* |
| | AB027705 and AB027706, *Daucus carota* |
| | AB034249, *Croton sublyratus* |
| | AB034250, *Scoparia dulcis* |
| | AF020041, *Helianthus annuus* |
| | AF049658, *Drosophila melanogaster* signal recognition particle 19 kDa protein (srp19) gene, partial sequence; and geranylgeranyl pyrophosphate synthase (quemao) gene, complete cds |
| | AF049659, *Drosophila melanogaster* geranylgeranyl pyrophosphate synthase mRNA, complete cds |
| | AF139916, *Brevibacterium linens* |
| | AF279807, *Penicillium paxilli* geranylgeranyl pyrophosphate synthase (ggs1) gene, complete |
| | AF279808, *Penicillium paxilli* dimethylallyl tryptophan synthase (paxD) gene, partial cds; and cytochrome P450 monooxygenase (paxQ), cytochrome P450 monooxygenase (paxP), PaxC (paxC), monooxygenase (paxM), geranylgeranyl pyrophosphate synthase (paxG), PaxU (paxU), and metabolite transporter (pax T) genes, complete cds |
| | AJ010302, *Rhodobacter sphaeroides* |
| | AJ133724, *Mycobacterium aurum* |
| | AJ276129, *Mucor circinelloides* f. *lusitanicus* carG gene for geranylgeranyl pyrophosphate synthase, exons 1–6 |
| | D85029, *Arabidopsis thaliana* mRNA for geranylgeranyl pyrophosphate synthase, partial cds |
| | L25813, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | U15778, *Lupinus albus* geranylgeranyl pyrophosphate synthase (ggps1) mRNA, complete cds |
| | U44876, *Arabidopsis thaliana* pregeranylgeranyl pyrophosphate synthase (GGPS2) mRNA, complete cds |
| | X92893, *C. roseus* |
| | X95596, *S. griseus* |

TABLE 2-continued

Sources of Genes Encoding the Lower Carotenoid Biosynthetic Pathway

| Gene | GenBank Accession Number and Source Organism |
|---|---|
| crtX (Zeaxanthin glucosylase) | X98795, *S. alba*<br>Y15112, *Paracoccus marcusii*<br>D90087, *E. uredovora*<br>M87280 and M90698, *Pantoea agglomerans* |
| crtY (Lycopene-β-cyclase) | AF139916, *Brevibacterium linens*<br>AF152246, *Citrus x paradisi*<br>AF218415, *Bradyrhizobium* sp. ORS278<br>AF272737, *Streptomyces griseus* strain IFO13350 AJ133724, *Mycobacterium aurum*<br>AJ250827, *Rhizomucor circinelloides* f. *lusitanicus* carRP gene for lycopene cyclase/phytoene synthase, exons 1–2<br>AJ276965, *Phycomyces blakesleeanus* carRA gene for phytoene synthase/lycopene cyclase, exons 1–2<br>D58420, *Agrobacterium aurantiacum*<br>D83513, *Erythrobacter longus*<br>L40176, *Arabidopsis thaliana* lycopene cyclase (LYC) mRNA, complete cds<br>M87280, *Pantoea agglomerans*<br>U50738, *Arabodopsis thaliana* lycopene epsilon cyclase mRNA, complete cds<br>U50739, *Arabidosis thaliana* lycopene β cyclase mRNA, complete cds<br>U62808, *Flavobacterium* ATCC21588<br>X74599, *Synechococcus* sp. lcy gene for lycopene cyclase<br>X81787, *N. tabacum* CrtL-1 gene encoding lycopene cyclase<br>X86221, *C. annuum*<br>X86452, *L. esculentum* mRNA for lycopene β-cyclase<br>X95596, *S. griseus*<br>X98796, *N. pseudonarcissus* |
| crtL (lycopene β-cyclase) | AAF10377.1, *Deinococcus radiodurans* R1 |
| crtI (Phytoene desaturase) | AB046992, *Citrus unshiu* CitPDS1 mRNA for phytoene desaturase, complete cds<br>AF039585, *Zea mays* phytoene desaturase (pds1) gene promoter region and exon 1<br>AF049356, *Oryza sativa* phytoene desaturase precursor (Pds) mRNA, complete cds<br>AF139916, *Brevibacterium linens*<br>AF218415, *Bradyrhizobium* sp. ORS278<br>AF251014, *Tagetes erecta*<br>AF364515, *Citrus x paradisi*<br>D58420, *Agrobacterium aurantiacum*<br>D83514, *Erythrobacter longus*<br>L16237, *Arabidopsis thaliana*<br>L37405, *Streptomyces griseus* geranylgeranyl pyrophosphate synthase (crtB), phytoene desaturase (crtE) and phytoene synthase (crtI) genes, complete cds<br>L39266, *Zea mays* phytoene desaturase (Pds) mRNA, complete cds<br>M64704, Soybean phytoene desaturase<br>M88683, *Lycopersicon esculentum* phytoene desaturase (pds) mRNA, complete cds<br>S71770, carotenoid gene cluster<br>U37285, *Zea mays*<br>U46919, *Solanum lycopersicum* phytoene desaturase (Pds) gene, partial cds<br>U62808, *Flavobacterium* ATCC21588<br>X55289, *Synechococcus* pds gene for phytoene desaturase<br>X59948, *L esculentum*<br>X62574, *Synechocystis* sp. pds gene for phytoene desaturase<br>X68058, *C. annuum* pds1 mRNA for phytoene desaturase<br>X71023, *Lycopersicon esculentum* pds gene for phytoene desaturase<br>X78271, *L. esculentum* (Ailsa Craig) PDS gene<br>X78434, *P. blakesleeanus* (NRRL1555) carB gene<br>X78815, *N. pseudonarcissus*<br>X86783, *H. pluvialis*<br>Y14807, *Dunaliella bardawil*<br>Y15007, *Xanthophyllomyces dendrorhous*<br>Y15112, *Paracoccus marcusii*<br>Y15114, *Anabaena* PCC7210 crtP gene<br>Z11165, *R. capsulatus* |

TABLE 2-continued

Sources of Genes Encoding the Lower Carotenoid Biosynthetic Pathway

| Gene | GenBank Accession Number and Source Organism |
|---|---|
| crtB (Phytoene synthase) | AB001284, *Spirulina platensis*<br>AB032797, *Daucus carota* PSY mRNA for phytoene synthase, complete cds<br>AB034704, *Rubrivivax gelatinosus*<br>AB037975, *Citrus unshiu*<br>AF009954, *Arabidopsis thaliana* phytoene synthase (PSY) gene, complete cds<br>AF139916, *Brevibacterium linens*<br>AF152892, *Citrus x paradisi*<br>AF218415, *Bradyrhizobium* sp. ORS278<br>AF220218, *Citrus unshiu* phytoene synthase (Psy1) mRNA, complete cds<br>AJ010302, *Rhodobacter*<br>AJ133724, *Mycobacterium aurum*<br>AJ278287, *Phycomyces blakesleeanus* carRA gene for lycopene cyclase/phytoene synthase,<br>AJ304825, *Helianthus annuus* mRNA for phytoene synthase (psy gene)<br>AJ308385, *Helianthus annuus* mRNA for phytoene synthase (psy gene)<br>D58420, *Agrobacterium aurantiacum*<br>L23424, *Lycopersicon esculentum* phytoene synthase (PSY2) mRNA, complete cds<br>L25812, *Arabidopsis thaliana*<br>L37405, *Streptomyces griseus* geranylgeranyl pyrophosphate synthase (crtB), phytoene desaturase (crtE) and phytoene synthase (crtI) genes, complete cds<br>M38424, *Pantoea agglomerans* phytoene synthase (crtE) gene, complete cds<br>M87280, *Pantoea agglomerans*<br>S71770, Carotenoid gene cluster<br>U32636, *Zea mays* phytoene synthase (Y1) gene, complete cds<br>U62808, *Flavobacterium* ATCC21588<br>U87626, *Rubrivivax gelatinosus*<br>U91900, *Dunaliella bardawil*<br>X52291, *Rhodobacter capsulatus*<br>X60441, *L. esculentum* Gtom5 gene for phytoene synthase<br>X63873, *Synechococcus* PCC7942 pys gene for phytoene synthase<br>X68017, *C. annuum* psyl mRNA for phytoene synthase<br>X69172, *Synechocystis* sp. pys gene for phytoene synthase<br>X78814, *N. pseudonarcissus* |
| crtZ (β-carotene hydroxylase) | D58420, *Agrobacterium aurantiacum*<br>D58422, *Alcaligenes* sp.<br>D90087, *E. uredovora*<br>M87280, *Pantoea agglomerans*<br>U62808, *Flavobacterium* ATCC21588<br>Y15112, *Paracoccus marcusii* |
| crtW (β-carotene ketolase) | AF218415, *Bradyrhizobium* sp. ORS278<br>D45881, *Haematococcus pluvialis*<br>D58420, *Agrobacterium aurantiacum*<br>D58422, *Alcaligenes* sp.<br>X86782, *H. pluvialis*<br>Y15112, *Paracoccus marcusii* |
| crtO (carotenoid ketolase) | X86782, *H. pluvialis*<br>Y15112, *Paracoccus marcusii* |
| crtU (carotenoid desaturase) | AF047490, *Zea mays*<br>AF121947, *Arabidopsis thaliana*<br>AF139916, *Brevibacterium linens*<br>AF195507, *Lycopersicon esculentum*<br>AF272737, *Streptomyces griseus* strain IF013350<br>AF372617, *Citrus x paradisi*<br>AJ133724, *Mycobacterium aurum*<br>AJ224683, *Narcissus pseudonarcissus*<br>D26095 and U38550, *Anabaena* sp.<br>X89897, *C. annuum*<br>Y15115, *Anabaena* PCC7210 |
| crtA (spheroidene monooxygenase) | AJ010302, *Rhodobacter sphaeroides*<br>Z11165 and X52291, *Rhodobacter capsulatus* |
| crtC | AB034704, *Rubrivivax gelatinosus*<br>AF195122 and AJ010302, *Rhodobacter sphaeroides*<br>AF287480, *Chlorobium tepidum* |

TABLE 2-continued

Sources of Genes Encoding the Lower Carotenoid Biosynthetic Pathway

| Gene | GenBank Accession Number and Source Organism |
|---|---|
| | U73944, *Rubrivivax gelatinosus* |
| | X52291 and Z11165, *Rhodobacter capsulatus* |
| | Z21955, *M. xanthus* |
| crtD (carotenoid 3,4-desaturase | AJ010302 and X63204, *Rhodobacter sphaeroides* |
| | U73944, *Rubrivivax gelatinosus* |
| | X52291 and Z11165, *Rhodobacter capsulatus* |
| crtF (1-OH-carotenoid methylase) | AB034704, *Rubrivivax gelatinosus* |
| | AF288602, *Chloroflexus aurantiacus* |
| | AJ010302, *Rhodobacter sphaeroides* |
| | X52291 and Z11165, *Rhodobacter capsulatus* |
| crtN | X73889, *S. aureus* |

By using various combinations of the genes presented in Tables 1 and 2 and the preferred genes of the present invention, innumerable different carotenoid substrates may be made using the methods of the present invention, provided sufficient sources of FPP are available in the host organism. For example, the gene cluster crtEXYIB enables the production of β-carotene. Addition of the crtZ to crtEXYIB enables the production of zeaxanthin, while the crtEXYIBZO cluster leads to production of astaxanthin and canthaxanthin.

Recombinant Bacterial Expression

A codon-optimized gene encoding a carotene desaturase has been recombinantly expressed in a heterologous gram negative bacterial host. Expression of crtU in recombinant bacterial hosts will be useful for 1) the production of various isoprenoid pathway intermediates, 2) the modulation of any preexisting pathway in the host cell, and 3) the synthesis of new products heretofore not possible using the host cell.

Preferred heterologous host cells for expression of the instant genes and nucleic acid fragments are bacterial hosts that can be found broadly within the families Bacteroidaceae, Enterobacteriaceae, Vibrionaceae, Pasteurellae, Pseudomonadaceae and Neisseriaceae. Bacterial hosts preferred for use in the present invention will belong to genera including, but not limited to *Bacteroides, Fusobacterium, Escherichia, Klebsiella, Proteus, Enterobacter, Serratia, Salmonella, Shigella, Citrobacter, Morganella, Yersinia, Erwinia, Vibrio, Aeromonas, Pasteurella, Haemophilus, Actinobacillus, Pseudomonas, Brucella, Flavobacterium, Alcaligenes, Acetobacter, Achromobacter, Acinetobacter,* and *Moraxella*. Most preferred hosts are those of the genus *Escherichia*, where *E. coli* is particularly suitable.

It will be appreciated by the skilled artisan that the expression of the present crtU genes may be regulated by controlling a number of well-known factors. For example, large-scale bacterial growth and functional gene expression may utilize a wide range of simple or complex carbohydrates, organic acids and alcohols, and saturated hydrocarbons. However, the functional genes such as crtU may be regulated, repressed or depressed by specific growth conditions, which may include the form and amount of nitrogen, phosphorous, sulfur, oxygen, carbon or any trace micronutrient, including small inorganic ions. In addition, the regulation of crtU genes may be achieved by the presence or absence of specific regulatory molecules that are added to the culture and are not typically considered nutrient or energy sources. Growth rate may also be an important regulatory factor in gene expression.

Bacterial expression systems and expression vectors containing regulatory sequences that direct high-level expression of foreign proteins are well known to those skilled in the art. Any of these could be used to construct chimeric genes for expression of present carotene desaturases. These chimeric genes could then be introduced into appropriate microorganisms via transformation to provide high-level expression of the enzymes.

Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' to the coding sequence which harbors transcriptional initiation controls and a region 3' to the coding sequence which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant coding sequences in the desired host cell, are numerous and familiar to those skilled in the art. Virtually any promoter capable of driving these genes is suitable for the present invention including, but not limited to, lac, ara, tet, trp, $IP_L$, $IP_R$, T7, tac, and trc. Termination control regions may also be derived from various genes native to the preferred hosts. Optionally, a termination site may be unnecessary, however, it is most preferred if included.

Pathway Regulation

Knowledge of the sequence of the present gene will be useful in manipulating the upper or lower carotenoid biosynthetic pathways in any organism having such a pathway. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced, specific genes may be upregulated to increase the output of the pathway. For example, additional copies of the targeted genes may be introduced into the host cell on multicopy plasmids such as pBR322. Alternatively, the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be affected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.*, 171:4617–4622 (1989), Balbas et al., *Gene*, 136:211–213 (1993), Gueldener et al., *Nucleic Acids Res.*, 24:2519–2524 (1996), and Smith et al., *Methods Mol. Cell. Biol.*, 5:270–277 (1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227 (1992) (hereinafter "Deshpande").

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element).

Within the context of the present invention, where there is a pre-existing carotenoid pathway in the selected host cell, it will be useful, for example to disrupt the gene encoding the ketolase encoded by crtO. This embodiment also applies to other carotenoid ketolase known in the art (i.e bkt and crtW ketolases). The gene product of crtO/crtW/bkt competes with CrtU for the same substrate, and disruption of the ketolase will be expected to enhance the enzymatic product of crtU.

Industrial Production of Aryl Carotenoids

Where commercial production of aryl-carotenoid compounds is desired using the present crtU gene, a variety of culture methodologies may be applied. For example, large-scale production of a specific gene product, overexpressed from a recombinant bacterial host, may be produced by either batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch culturing methods are common and well known in the art and examples may be found in Brock (supra) and Deshpande (supra).

Commercial production of aryl-carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady-state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock (supra). Fermentation media in the present invention must contain suitable carbon substrates. Suitable substrates may include, but are not limited to, monosaccharides such as glucose and fructose, oligosaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Hence, it is contemplated that the source of carbon utilized in the present invention may encompass a wide variety of carbon containing substrates and will only be limited by the choice of organism. λ-Red Recombinase System Various genetic systems were used herein to express portions of the lower carotenoid biosynthetic pathway. In particular the λ-red recombinase system in combination with a bacteriophage P1 transduction system and various integration cassettes were used to engineer the appropriate gram negative host for substrate production.

The λ-Red recombinase system used in the present invention is contained on a helper plasmid (pKD46; SEQ ID NO:55)) and is comprised of three essential genes, exo, bet, and gam (Datsenko and Wanner, supra). The exo gene encodes an λ-exonuclease, which processively degrades the 5' end strand of double-stranded (ds) DNA and creates 3' single-stranded overhangs. Bet encodes for a protein which complexes with the λ-exonuclease and binds to the single stranded DNA and promotes renaturation of complementary strands and is capable of mediating exchange reactions. Gam encodes for a protein that binds to the E.coli's RecBCD complex and blocks the complex's endonuclease activity.

The λ-Red system is used in the present invention because homologous recombination in E.coli occurs at a very low frequency and usually requires extensive regions of homology. The λ-Red system facilitates the ability to use short regions of homology (10–50 bp) flanking linear double-stranded (ds) DNA fragments for homologous recombination. Additionally, the RecBCD complex normally expressed in E.coli prevents the use of linear dsDNA for transformation as the complex's exonuclease activity efficiently degrades linear dsDNA. Inhibition of the RecBCD complex's endonuclease activity by gam is essential for efficient homologous recombination using linear dsDNA fragments.

Integration Cassettes

Figure 3:
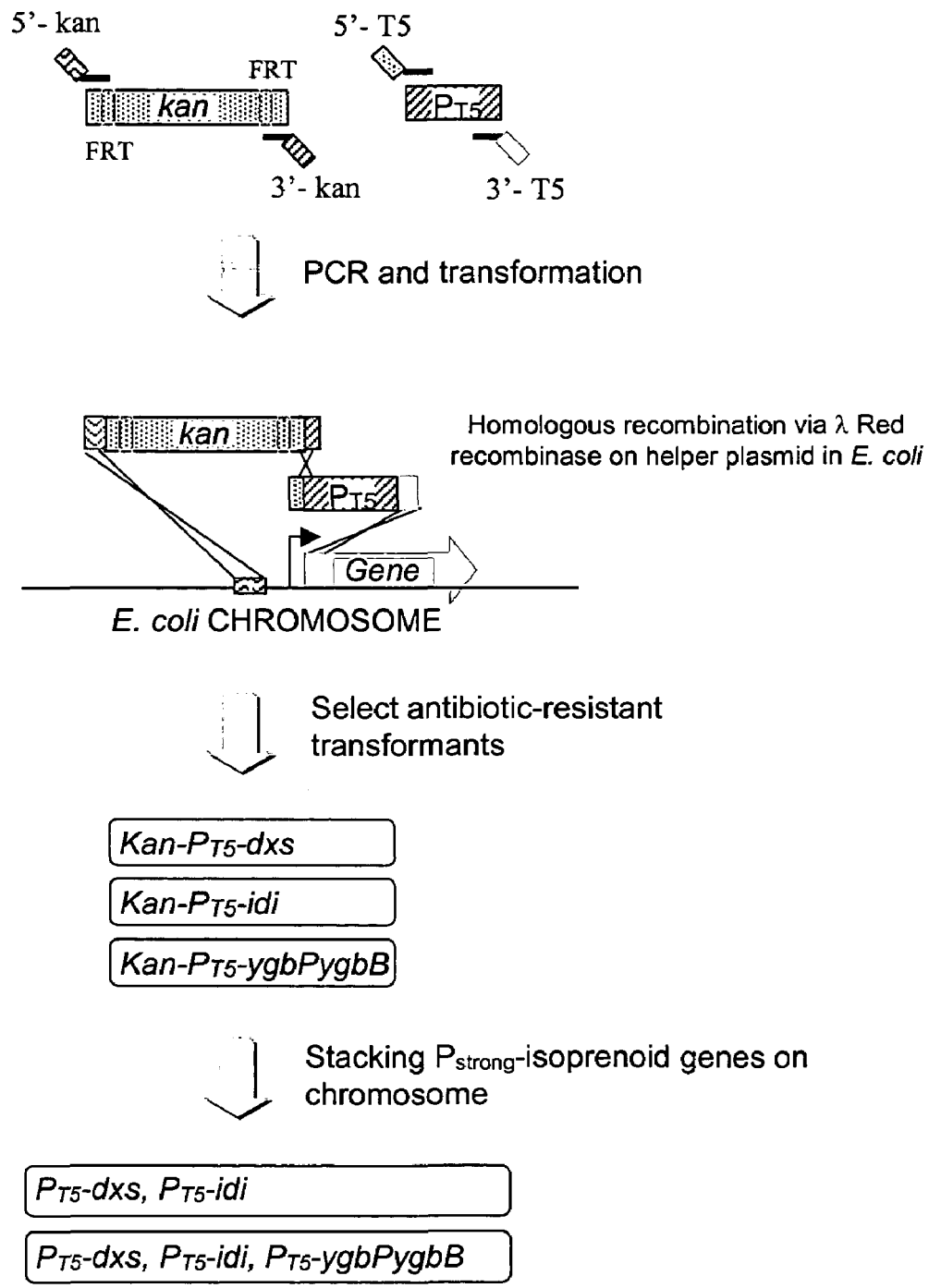
FIG. 3 shows the strategy for chromosomal promoter replacement of isoprenoid genes using two PCR fragments integration method in *E. coli*.
Figure 4:
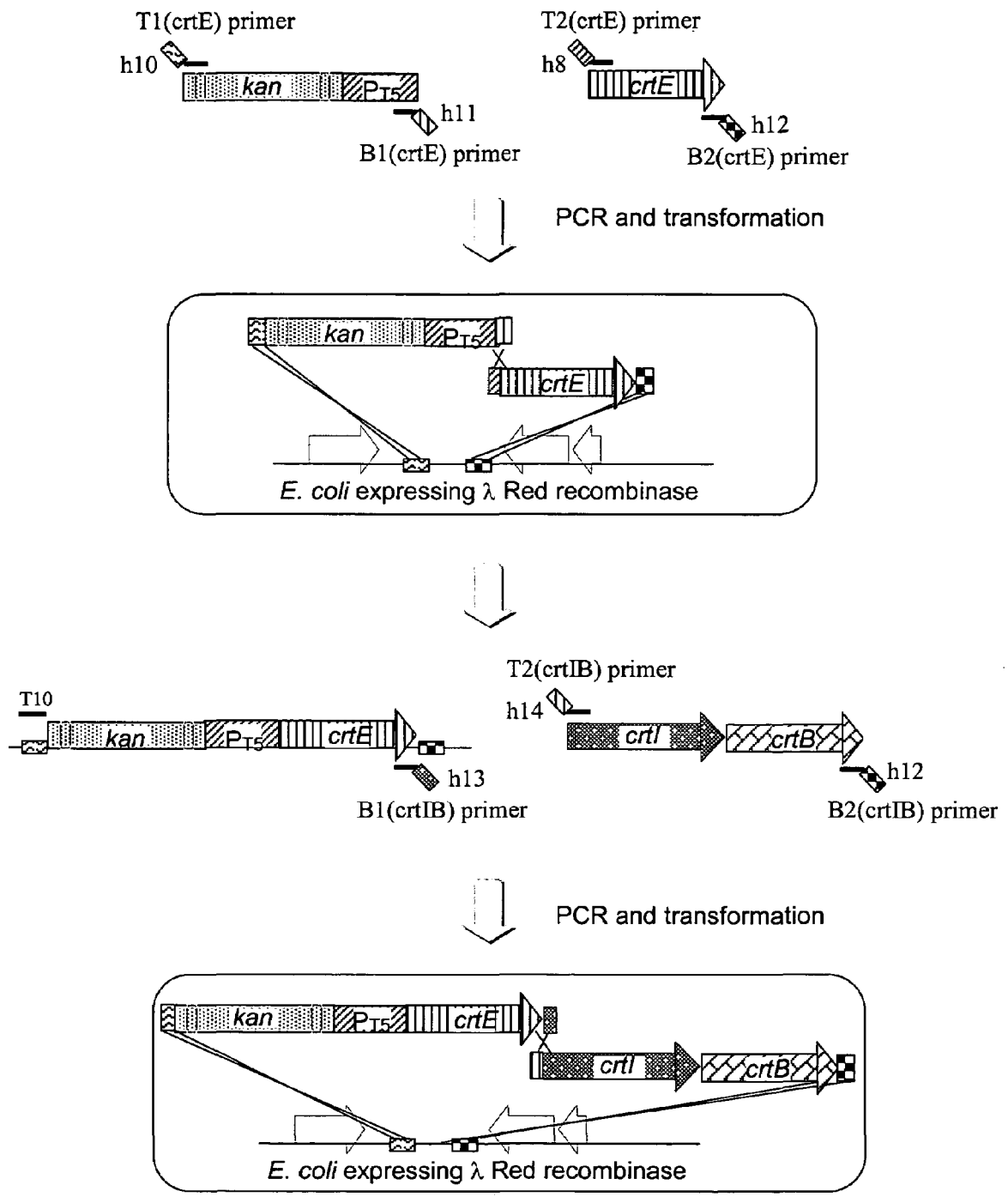
FIG. 4 shows the strategy used for construction of the kan-$P_{T5}$-crtEIB construct.

As used in the present invention, "integration cassettes" are the linear double-stranded DNA fragments chromosomally integrated by triple homologous recombination via two PCR-generated linear fragments as seen in FIGS. 3 and 4. The integration cassette comprises a nucleic acid integration fragment that is a promoter and/or gene, a selectable marker bounded by specific recombinase sites responsive to a recombinase, and homology arms having homology to different portions of a donor cell chromosome. The homology arms, generally about 10 to 50 base pairs in length, are chosen so have homology with either a specific sequence on the bacterial chromosome or a specific sequence on another recombination element. In the present invention, the native promoter of the isoprenoid genes is replaced with the phage T5 strong promoter in combination with a selection marker by using one or two linear dsDNA PCR-generated fragments (FIG. 3).

Integration cassettes may contain one or more genes or coding sequences. These genes may be natural or foreign to the host cell and may include those which have undergone previous modification, such as transposon disruption. In the present method, genes useful in optimization of isoprenoid/carotenoid production are used. The genes of the isoprenoid biosynthetic pathway are selected from the group consisting of dxs, dxr, ygbP, ychB, ygbB, idi, ispA, lytB, gcpE, pyrG, ispB, crtE, crtY, crtL, crtI, crtB, crtX, crtZ, crtW, crtO, crtA, crtC, crtD, crtF, crtN1, crtN2, crtN3, ald, crtU, and homologs thereof from other microorganisms.

Integration cassettes can include selectable markers, preferably flanked by site-specific recombination sequences, allowing for easy removal of the markers after selection. The selectable marker is selected from the group consisting of antibiotic resistance markers, enzymatic markers wherein the expressed marker catalyzes a chemical reaction creating a measurable difference in phenotypic appearance, and amino acid biosynthesis enzymes which enable a normally auxotrophic bacteria to grow without the exogenously supplied amino acid; the amino acid synthesized by the amino acid biosynthesis enzyme.

Bacteriophage P1 Transduction System

Transduction is a phenomenon in which bacterial DNA is transferred from one bacterial cell (the donor) to another (the recipient) by a phage particle containing bacterial DNA. When a population of donor bacteria is infected with a phage, the events of the phage lytic cycle may be initiated. During lytic infection, the enzymes responsible for packaging viral DNA into the bacteriophage sometimes accidentally package host DNA. The resulting particle is called a transducing particle. Upon lysis of the cell these particles, called P1 lysate, are released along with normal virions, and so the lysate contains a mixture of normal virions and transducing particles. When this lysate is used to infect a population of recipient cells, most of the cells become infected with normal virus. However, a small proportion of the population receives transducing particles that inject the DNA they received from the previous host bacterium. This DNA can now undergo genetic recombination with the DNA of another host. Conventional P1 transduction can move only one genetic trait (i.e. gene) at a time from one to another host. The Applicants used a system for stacking multiple genetic traits into one *E. coli* host in a parallel fashion using the bacteriophage P1 mixtures in combination with the site-specific recombinase system for removal of selection markers (U.S. Ser. No. 10/734778).

DESCRIPTION OF THE PREFERRED EMBODIMENTS

The present codon-optimized crtU genes, encoding carotene desaturase, are useful for the creation of recombinant organisms capable of producing aryl-carotenoid compounds. Nucleic acid fragments encoding CrtU have been isolated from a strain of *Brevibacterium linens*, codon-optimized for expression in a gram negative host, and subsequently expressed in *Escherichia coli*.

Applicants have isolated the crtu gene (SEQ ID NO:15) and amplified it by PCR from *Brevibacterium linens* ATCC 9175 (Example 4). In one embodiment, the crtU gene from *B. linens* was codon-optimized for recombinant expression in a gram negative heterologous host. In a more preferred embodiment, the optimized crtU gene (SEQ ID NOs:18 or 53) contained 5 codon substitutions at the 5' end of the gene and 9 codon substitutions at the 3' end creating a codon-optimized gene encoding a polypeptide having the amino acid sequence setfor in SEQ ID NO:19. In another preferred embodiment, the codon-optimized gene was expressed in *E. coli* (Examples 5–7).

The heterologous host cells were genetically modified to express carotenoid biosynthesis genes for the production of carotenoids having at least one β-ionone ring. In another embodiment, the codon optimized crtU gene was expressed in a heterologous host cell capable of producing a carotenoid substrate having at least one β-ionone ring for the production of aryl carotenoids (Example 5; FIG. 1). The carotenoid substrate, comprising at least one β-ionone ring, was converted by the expressed carotene desaturase (codon-optimized crtU) into an aryl carotenoid product. In a preferred embodiment, the heterologous host was a strain of *Escherichia coli*. In another preferred embodiment, the carotenoid biosynthesis genes were from the *Pantoea stewartii* crt gene cluster (Examples 1–3). In another embodiment, the carotene desaturase gene and one or more of the carotenoid biosynthesis genes were extrachromosomally expressed. In another embodiment, one or more of the genes of the present invention were chromosomally expressed.

In another embodiment, the lycopene cyclase expressed in the heterologous host cell selectively produced only monocyclic (single β-ionone ring) carotenoids (FIG. 1). In a preferred embodiment, the lycopene cyclase gene (crtL) from *Rhodococcus erythropolis* strain AN12, encoding a polypeptide having the amino acid sequence as described in SEQ ID NO:50, was used (Examples 15–17). The lycopene cyclase encoded by this gene has been reported to selectively produce monocyclic carotenoids (U.S. Ser. No. 10/292577). In a preferred embodiment, the monocyclic carotenoid produced was γ-carotene. In a more preferred embodiment, the codon-optimized carotene desaturase converted γ-carotene into chlorobactene (FIG. 1).

In another embodiment, the lycopene cyclase expressed in the heterologous host cell produces bicyclic carotenoids (two β-ionone rings) (FIG. 1). In a preferred embodiment, the lycopene cyclase used (SEQ ID NO:6) was from *Pantoea stewartii* (ATCC 8199). The bicyclic carotenoid produced using the lycopene cyclase (crtY) from *Pantoea stewartii* (ATCC 8199) was β-carotene. The codon-optimized carotene desaturase converted the β-carotene substrate produced by CrtY into β-isorenieratene and/or isorenieratene (Examples 5 and 10).

Figure 2:
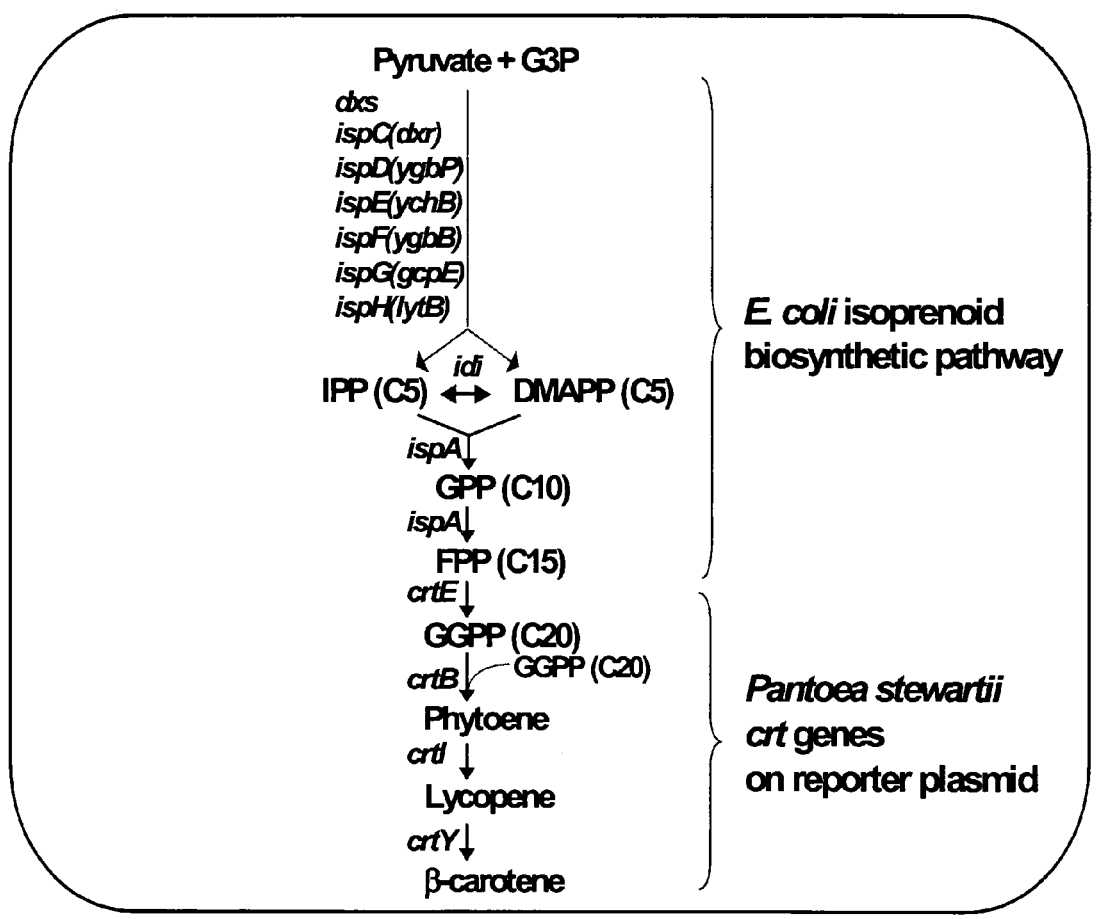
FIG. 2 shows the isoprenoid pathway in *E. coli*.

The Applicants show how to chromosomally-modify the heterologous host cell for increased expression of isoprenoid and/or carotenoid biosynthesis genes (Examples 7–9, and 11–14; FIG. 2). In a preferred embodiment, the promoters of the isoprenoid and/or carotenoid biosynthesis gene were replaced with a stronger promoter (FIG. 3). In a more preferred embodiment, the promoter was the phage T5 promoter ($P_{T5}$) (SEQ ID NO:57). In another preferred embodiment, the promoters for the dxs, idi, and ygbBygbP genes were replaced with $P_{T5}$ for increased carotenoid production (FIG. 3).

The carotenoid biosynthesis genes were chromosomally integrated into the heterologous host cell (Examples 12–14; FIG. 4). In a preferred embodiment, the chromosomally integrated carotenoid biosynthesis genes were genetically-engineered, replacing their natural promoters with a stronger promoter. In a more preferred embodiment, the carotenoid biosynthesis genes were expressed using the $P_{T5}$ promoter.

In another embodiment, the various genetically engineered genes were incorporated into a single heterologous host using trait stacking (Examples 8–9, 11, and 14; FIG. 3). In a preferred embodiment, the trait stacking was accomplished by P1 transduction.

In another embodiment, the codon optimized crtU gene is expressed in a gram negative host cell engineered for increased production of suitable carotenoid substrates. In another embodiment, one or more genes of the isoprenoid or carotenoid biosynthesis pathway are overexpressed. In another embodiment, one or more genes competing with the CrtU from the pool of suitable carotenoid substrates is down-regulated or knocked-out (i.e. carotenoid ketolases). In yet another embodiment, the gram negative host cell is *E. coli* strain DPR676 (ATCC# PTA-5136). In a further embodiment, the gram negative host cell produces aryl carotenoids at industrially-suitable levels. In yet a further embodiment, the gram negative host cell is capable of producing at least 3 mg/L aryl carotenoid during fermentation.

In another embodiment, carotene desaturase can be used as a catalyst for production of aryl carotenoids. The carotene desaturase catalyst can be used in the form of whole cells, partially purified components of a whole cell, and partially-purified or purified components enzymes. The catalyst can be immobilized in a soluble or insoluble support. In a preferred embodiment, the purified catalyst is contacted with a β-ionone ring containing carotenoid substrate for the production of aryl carotenoids.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Maniatis (supra), Silhavy (supra), and Ausubel (supra).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or Brock (supra). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" used the gap creation default value of 12 and the gap extension default value of 4. The CGC "Gap" or "Bestfit" programs used the default gap creation penalty of 50 and the default gap extension penalty of 3. Multiple alignments were created using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "mL" means milliliters, "L" means liters, "µL" means microliters, "µg" mean micrograms, and "rpm" means revolutions per minute.

Example 1

Cloning of Genes for β-carotene Synthesis from *Pantoea Stewartii*

Primers were designed using the sequence from *Erwinia uredovora* to amplify a fragment by PCR containing the crt genes. These sequences included 5'–3':

```
ATGACGGTCTGCGCAAAAAAACACG      SEQ ID NO:13

GAGAAATTATGTTGTGGATTTGGAATGC   SEQ ID NO:14
```

Chromosomal DNA was purified from *Pantoea stewartii* (ATCC no. 8199) and Pfu Turbo polymerase (Stratagene, La Jolla, Calif.) was used in a PCR amplification reaction under the following conditions: 94° C., 5 min; 94° C. (1 min)-60° C. (1 min)-72° C. (10 min) for 25 cycles, and 72° C. for 10 min. A single product of approximately 6.5 kb was observed following gel electrophoresis. Taq polymerase (Perkin Elmer) was used in a ten minute 72° C. reaction to add additional 3' adenosine nucleotides to the fragment for TOPO cloning into pCR4-TOPO (Invitrogen, Carlsbad, Calif.) to create pPCB13. Following transformation to *E. coli* DH5α (Life Technologies, Rockville, Md.) by electroporation, several colonies appeared to be bright yellow in color indicating that they were producing a carotenoid compound. Following plasmid isolation as instructed by the manufacturer using the Qiagen (Valencia, Calif.) miniprep kit, the plasmid containing the 6.5 kb amplified fragment was transposed with pGPS1.1 using the GPS-1 Genome Priming System kit (New England Biolabs, Inc., Beverly, Mass.). A number of these transposed plasmids were sequenced from each end of the transposon. Sequence was generated on an ABI Automatic sequencer using dye terminator technology (U.S. Pat. No. 5,366,860; EP 272007) using transposon specific primers. Sequence assembly was performed with the Sequencher program (Gene Codes Corp., Ann Arbor, Mich.).

Example 2

Identification and Characterization of Bacterial Genes

Genes encoding crtE, X, Y, I, B, and Z were identified by conducting BLAST (Basic Local Alignment Search Tool; Altschul et al., *J. Mol. Biol.* 215:403–410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J., *Nature Genetics*, 3:266–272 (1993)) provided by the NCBI.

All comparisons were done using either the BLASTNnr or BLASTXnr algorithm. The results of the BLAST comparisons are given in Table 3, listing the sequences to which they have the most similarity. Table 3 displays data based on the BLASTXnr algorithm with values reported in expect values. The Expect value estimates the statistical significance of the match, specifying the number of matches, with a given score, that are expected in a search of a database of this size absolutely by chance.

TABLE 3

| ORF | Gene Name | Similarity Identified | SEQ ID base | SEQ ID Peptide | % Identity[a] | % Similarity[b] | E-value[c] | Citation |
|---|---|---|---|---|---|---|---|---|
| 1 | crtE | Geranylgeranyl pryophosphate synthetase EC 2.5.1.29 gi|117509|sp|P21684|CRTE_PANAN GERANYLGERANYL PYROPHOSPHATE SYNTHETASE (GGPP SYNTHETASE) (FARNESYL TRANSTRANSFERASE) | 1 | 2 | 83 | 88 | e−137 | Misawa et al., J. Bacteriol. 172 (12), 6704–6712 (1990) |
| 2 | crtX | Zeaxanthin glucosyl transferase EC 2.4.1.- gi|1073294|pir||S52583 crtX protein - *Erwinia herbicola* | 3 | 4 | 75 | 79 | 0.0 | Lin et al., Mol. Gen. Genet. 245 (4), 417–423 (1994) |
| 3 | crtY | Lycopene cyclase gi|1073295|pir||S52585 lycopene cyclase - *Erwinia herbicola* | 5 | 6 | 83 | 91 | 0.0 | Lin et al., Mol. Gen. Genet. 245 (4), 417–423 (1994) |
| 4 | crtI | Phytoene desaturase EC 1.3.-.- gi|1073299|pir||S52586 phytoene dehydrogenase (EC 1.3.-.-) - *Erwinia herbicola* | 7 | 8 | 89 | 91 | 0.0 | Lin et al., Mol. Gen. Genet. 245 (4), 417–423 (1994) |
| 5 | crtB | Phytoene synthase EC 2.5.1.- gi|1073300|pir||S52587 prephytoene pyrophosphate synthase - *Erwinia herbicola* | 9 | 10 | 88 | 92 | e−150 | Lin et al., Mol. Gen. Genet. 245 (4), 417–423 (1994) |
| 6 | crtZ | Beta-carotene hydroxylase gi|117526|sp|P21688|CRTZ_PANAN BETA-CAROTENE HYDROXYLASE | 11 | 12 | 88 | 91 | 3e−88 | Misawa et al., J. Bacteriol. 172 (12), 6704–6712 (1990) |

[a] % Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance.

Example 3

Analysis of crt Gene Function by Transposon Mutagenesis

Several plasmids carrying transposons that were inserted into each coding region including crtE, crtX, crtY, crtI, crtB, and crtZ were chosen using sequence data generated in Example 1. These plasmid variants were transformed to *E. coli* MG1655 and grown in 100 mL Luria-Bertani broth in the presence of 100 µg/mL ampicillin. Cultures were grown for 18 h at 26° C., and the cells were harvested by centrifugation. Carotenoids were extracted from the cell pellets using 10 mL of acetone. The acetone was dried under nitrogen and the carotenoids were resuspended in 1 mL of methanol for HPLC analysis. A Beckman System Gold® HPLC with Beckman Gold Nouveau Software (Columbia, Md.) was used for the study. The crude extraction (0.1 mL) was loaded onto a 125×4 mm RP8 (5 µm particles) column with corresponding guard column (Hewlett-Packard, San Fernando, Calif.). The flow rate was 1 mL/min, while the solvent program used was: 0–11.5 min 40% water/60% methanol; 11.5–20 min 100% methanol; 20–30 min 40% water/60% methanol. The spectrum data were collected by a Beckman photodiode array detector (model 168).

In the wild-type clone with wild-type crtEXYIBZ, the carotenoid was found to have a retention time of 15.8 min and an absorption spectra of 450 nm, 475 nm. This was the same as the β-carotene standard. This suggested that the crtZ gene, oriented in the opposite direction, was not expressed in this construct. The transposon insertion in crtZ had no effect as expected (data not shown).

HPLC spectral analysis also revealed that a clone with a transposon insertion in crtx also produced β-carotene. This is consistent with the proposed function of crtX encoding a zeaxanthin glucosyl transferase enzyme at a later step of the carotenoid pathway following synthesis of β-carotene.

The transposon insertion in crtY did not produce β-carotene. The carotenoid's elution time (15.2 min) and absorption spectra (443 nm, 469 nm, 500 nm) agree with those of the lycopene standard. Accumulation of lycopene in the crtY mutant confirmed the role crtY as a lycopene cyclase encoding gene.

The crtI extraction, when monitored at 286 nm, had a peak with retention time of 16.3 min and with absorption spectra of 276 nm, 286 nm, 297 nm, which agrees with the reported spectrum for phytoene. Detection of phytoene in the crtI mutant confirmed the function of the crtI gene as one encoding a phytoene dehydrogenase enzyme.

The extraction of crtE mutant, crtB mutant or crtI mutant was clear. Loss of pigmented carotenoids in these mutants indicated that both the crtE gene and crtB gene are essential for carotenoid synthesis. No carotenoid was observed in either mutant, which is consistent with the proposed function of crtB encoding a prephytoene pyrophosphate synthase and crtE encoding a geranylgeranyl pyrophosphate synthetase. Both enzymes are required for β-carotene synthesis.

Results of the transposon mutagenesis experiments are shown below in Table 4. The site of transposon insertion into the gene cluster crtEXYIB is recorded, along with the color of the *E. coli* colonies observed on LB plates, the identity of the carotenoid compound (as determined by HPLC spectral analysis), and the experimentally assigned function of each gene.

TABLE 4

| Transposon insertion site | Colony color | Carotenoid observed by HPLC | Assigned gene function |
|---|---|---|---|
| Wild Type (with no transposon insertion) | Yellow | β-carotene | |
| crtE | White | None | Geranylgeranyl pyrophosphate synthetase |
| crtB | White | None | Prephytoene pyrophosphate synthase |
| crtI | White | Phytoene | Phytoene dehydrogenase |
| crtY | Pink | Lycopene | Lycopene cyclase |
| crtZ | Yellow | β-carotene | β-carotene hydroxylase |
| crtX | Yellow | β-carotene | Zeaxanthin glucosyl transferase |

Example 4

Synthesis of a crtU Gene Optimized for Expression in *E. coli*

A linear DNA fragment encoding a crtU gene was synthesized by PCR using the *Brevibacterium linens* (ATCC 9175) crtU genomic DNA (SEQ ID NO:15) as template with primer pairs: 1) crtU-F (SEQ ID NO:16), ATGACCCAGCGTCGCCGCCCGCGCGATCGCTTCGC CGAGAGAATCC AGGGCCCGCAG which contains a region modified from the original *B. linens* sequence (underlined, 24 bp) and a priming sequence (33 bp) matching the *B. linens* sequence; and 2) crtU-R (SEQ ID NO:17), TCAGCGACGGCGGCGGATCAGGCCCAGCACGCCA CGGCGCAGCAG GCCTCGGGTCGGTGGCGAC which contains a region modified from the *B. linens* sequence (underlined, 42 bp) and a priming sequence (22 bp) matching the *B. linens* sequence. A 1554 bp product was generated and was predicted to contain 5 codon substitutions at the 5' end of the *B. linens* crtU gene and 9 codon substitutions at the 3' end (SEQ ID NO:18). All of these substitutions are silent. The PCR reaction was performed using the Perkin Elmer PCR 9700 thermocycler (Perkin Elmer Corporation, Foster City, Calif.), the High Fidelity PCR Supermix (Invitrogen, Carlsbad, Calif.), 45 µL, and 1 µL of each primer and the *B. linens* crtU gene (SEQ ID NO:15) as template as described by the manufacturer. The temperature parameters were as follows: 98° C. (10 min), 31 cycles 98° C. (1 min)-60° C. (1 min)-72° C. (2 min), followed by 72° C. (10 min). The 1554 bp PCR product was purified by QIAquick PCR purification kit (Qiagen, Valencia, Calif.). Then the 1.5 kb band from the PCR product was purified by gel extraction using Zymoclean gel DNA recovery kit (Zymo Research, Orange, Calif.). Sequencing of the 1554 bp product revealed an additional silent mutation generated by PCR at position 825 (SEQ ID NO:53). A thymine (T) residue was substituted for the wild-type cytosine (C). The predicted amino acid sequence was not affected by this silent mutation.

Example 5

Cloning of the Optimized crtU Gene and Expression in a β-carotene Producing *E. coli* for Production of Isorenieratene The modified crtU PCR fragment (SEQ ID NO:53) was cloned into pTrcHis2-TOPO vector by using pTrcHis2-TOPO TA Expression kit (Invitrogen, Carlsbad, Calif.). A 4 µL aliquot of the modified crtU PCR product recovered from gel extraction in Example 4 was mixed with 1 µL pTrcHis2-TOPO vector and incubated 5 min at room temp. A 2 µL aliquot of this PCR product-vector mixture was transformed into One Shot *E. coli* competent cells (Invitrogen) by heat-shock. Transformants were selected on 100 µg/mL of ampicillin LB plate at 37° C. Plasmids were isolated from resulting colonies and analyzed by restriction enzyme digestion to verify plasmid construct. The DNA sequence of the insert was verified by sequencing. The final construct was named pTrcHis2-TOPO-crtU.

The pTrcHis2-TOPO-crtU plasmid was transformed into *E.coli* strain MG1655 harboring the pBHR-crt+ plasmid. pBHR-crt + carries a carotenoid biosynthetic gene cluster from *Pantoea stewartii*, as described in Examples 1 and 2, cloned into the EcoRI site of pBHR1 (MoBiTec, Goettingen, Germany) such that expression of the crtEBIY genes was driven by the promoter of the chloramphenicol resistance gene. Transformants were selected on 100 µg/mL of ampicillin and 50 µg/mL of kanamycin LB plate at 37° C. Colonies that appeared yellow were inoculated into 100 mL LB with 100 µg/mL of ampicillin, 50 µg/mL of kanamycin and 1 mM IPTG. After incubation 12 to 18 hours at 37° C. with shaking at 250 rpm, the cultures were centrifuged at 8000 rpm for 10 min at 4° C. A 2 mL aliquot of acetone was added to the pellet and the mixture was vortexed 2 min to extract the carotenoid pigments. The mixture was centrifuged in a microcentrifuge to separate the cell debris. After filtration with an Acrodisc CR25 mm syringe filter (Pall Corporation, Ann Arbor, Mich.), the acetone fraction was analyzed by HPLC (Beckman System Gold, Fullerton, Calif.) using column of SUPELCO discovery C18 (5 µm, 4.6×250 mm). Liquid chromatography was performed with flow rate of 2.0 mL/min. The elution was initiated at 0% acetone and ends in 20 minutes with 50% acetone in linear gradient change. HPLC analysis indicated that *E. coli* strain MG1655 with plasmid pBHR-crt+ and plasmid pTrcHis2-TOPO-crtU produced the isorenieratene (49.4% total extractable pigment) and β-isorenieratene (21.1% of total extractable pigment) and β-carotene (29.5% of total extractable pigment).

The resulting solution with pigments was analyzed by an Agilent Series 1100 LC/MSD (Agilent, Foster City, Calif.). Liquid chromatography was performed using a SB-C18 (5 µm, 4.6×250 mm) column (Agilent) with flow rate of 1.5 mL/min. The elution was initiated with a 52 mL linear solvent gradient from acetonitrile to 60% acetone and 40% acetonitrile. MS analysis confirmed the presence of isorenieratene (molecular weight of 529), β-isorenieratene (molecular weight of 533), and β-carotene (molecular weight of 537).

Example 6

Protein Gel Electrophoresis of the Optimized crtU Gene Product in *E. coli*

*E. coli* MG1655 with plasmid pBHR-crt+ and plasmid pTrcHis2-TOPO-crtU was inoculated into 100 mL LB with 100 µg/mL of ampicillin, 50 µg/mL of kanamycin and 1 mM IPTG. A 5 mL culture aliquot was centrifuged to pellet cells. All pellets were resuspended in 150 μL B-Per II solution (Pierce, Rockford, Ill.) and vortexed to mix well. After 5 min in a microcentrifuge, the supernatant was isolated and mixed with 4× sample buffer (Invitrogen) to final 1× concentration and incubated at 95° C. for 5 min. A 10 μL aliquot from each sample was loaded onto a pre-cast 4–12% Bis-Tris gel (Invitrogen). Following electrophoresis, the gel was stained using SimplyBlue Safestain (Invitrogen) and de-stained with water. All samples proven to produce isorenieratene by HPLC contained a unique band at 57 kDa. The 57 kDa band was not observed in extracts from the E. coli strain carrying plasmid pBHR-crt+ alone or from an E. coli strain with pBHR1-crt+ and pTrcHis2-TOPO with the optimized crtU cloned in the opposite orientation of the promoter.

Example 7

Construction of E. coli Strains with the Phage T5 Strong Promoter Chromosomally Integrated Upstream of the Isoprenoid Genes The native promoters of the E. coli isoprenoid genes dxs, idi, and ygbBygbP (FIG. 2) were replaced with the phage T5 ($P_{T5}$) strong promoter (SEQ ID NO:57) using a PCR-fragment chromosomal integration method as described in FIG. 3. The method for replacement is based on homologous recombination via the λ-Red recombinase encoded on a helper plasmid. Recombination occurs between the E. coli chromosome and two PCR fragments that contain 20–50 bp homology patches at both ends of PCR fragments (FIG. 3). A two PCR fragment method was used for chromosomal integration of the kanamycin selectable marker and phage T5 promoter in the front of the E. coli isoprenoid genes dxs, idi, and ygbBygbP (U.S. Ser. No. 10/735442, hereby incorporated by reference). For the two PCR fragment method, the two fragments included a linear DNA fragment (1489 bp) containing a kanamycin selectable marker flanked by site-specific recombinase target sequences (FRT) and a linear DNA fragment (154 bp) containing a phage T5 promoter ($P_{T5}$) comprising the −10 and −35 consensus promoter sequences, lac operator (lacO), and a ribosomal binding site (RBS).

By using the two PCR fragment method, the kanamycin selectable marker and phage T5 promoter (kan-$P_{T5}$) were integrated upstream of the dxs, idi, and ygbBygbP coding sequences, yielding E. coli kan-$P_{T5}$-dxs, E. coli kan-$P_{T5}$-idi, and E. coli kan-$P_{T5}$-ygbBygbP. The linear DNA fragment (1489 bp), which contained a kanamycin selectable marker, was synthesized by PCR from plasmid pKD4 (Datsenko and Wanner, supra) with primer pairs as follows in Table 5.

TABLE 5

Primers for Amplification of the Kanamycin Selectable Marker

| Primer Name | Primer Sequence | SEQ ID NO: |
|---|---|---|
| 5'-kan(dxs) | TGGAAGCGCTAGCGGACTACATCATCCAGCGTAAT AAATAACGTCTTGAGCGATTGTGTAG[1] | 20 |
| 5'-kan(idi) | TCTGATGCGCAAGCTGAAGAAAAATGAGCATGGAG AATAATATGACGTCTTGAGCGATTGTGTAG[1] | 21 |
| 5'-kan(ygbBP) | GACGCGTCGAAGCGCGCACAGTCTGCGGGGCAAA ACAATCGATAACGTCTTGAGCGATTGTGTAG[1] | 22 |
| 3'-kan | GAAGACGAAAGGGCCTCGTGATACGCCTATTTTTAT AGGTTATATGAATATCCTCCTTAGTTCC[2] | 23 |

[1]The underlined sequences illustrate each respective homology arm chosen to match sequences in the upstream region of the chromosomal integration site, while the remainder is the priming sequence
[2]The underlined sequences illustrate homology arm chosen to match sequences in the 5'-end region of the T5 promoter DNA fragment The second linear DNA fragment (154 bp) containing a phage T5 promoter was synthesized by PCR from pQE30 (QIAGEN, Inc. Valencia, Calif.) with primer pairs as follows in Table 6.

TABLE 6

Primers for Amplification of the T5 Promoter

| Primer Name | Primer Sequence | SEQ ID NO: |
|---|---|---|
| 5'-T5 | CTAAGGAGGATATTCATATAACCTATAAAAATAG GCGTATCACGAGGCCC[3] | 24 |
| 3'-T5(dxs) | GGAGTCGACCAGTGCCAGGGTCGGGTATTTGGC AATATCAAAACTCATAGTTAATTTCTCCTCTTTAAT G[4] | 25 |

TABLE 6-continued

Primers for Amplification of the T5 Promoter

| Primer Name | Primer Sequence | SEQ ID NO: |
|---|---|---|
| 3'-T5(idi) | TGGGAACTCCCTGTGCATTCAATAAAATGACGTG TTCCGTTTGCATAGTTAATTTCTCCTCTTTAATG[4] | 26 |
| 3'-T5(ygbBP) | CGGCCGCCGGAACCACGGCGCAAACATCCAAAT GAGTGGTTGCCATAGTTAATTTCTCCTCTTTAATG[4] | 27 |

[3]The underlined sequences illustrate homology arm chosen to match sequences in the 3'-end region of the kanamycin DNA fragment
[4]The underlined sequences illustrate each respective homology arm chosen to match sequences in the downstream region of the chromosomal integration site Standard PCR conditions were used to amplify the linear DNA fragments with AmpliTaq Gold® polymerase (Applied Biosystems, Foster City, Calif.) as follows:

| PCR reaction: | PCR reaction mixture: |
|---|---|
| Step1 94° C. 3 min | 0.5 µL plasmid DNA |
| Step2 93° C. 30 sec | 5 µL 10× PCR buffer |
| Step3 55° C. 1 min | 1 µL dNTP mixture (10 mM) |
| Step4 72° C. 3 min | 1 µL 5'-primer (20 µM) |
| Step5 Go To Step2, 30 cycles | 1 µL 3'-primer (20 µM) |
| Step6 72° C. 5 min | 0.5 µL AmpliTaq Gold ® polymerase |
| | 41 µL sterilized dH$_2$O |

After completing the PCR reactions, 50 µL of each PCR reaction mixture was run on a 1% agarose gel and the PCR products were purified using the QIAquick Gel Extraction Kit™ as per the manufacturer's instructions (Cat. # 28704, QIAGEN Inc., Valencia, Calif.). The PCR products were eluted with 10 µL of distilled water. The DNA Clean & Concentrator™ kit (Zymo Research, Orange, Calif.) was used to further purify the PCR product fragments as per the manufacturer's instructions. The PCR products were eluted with 6–8 µL of distilled water to a concentration of 0.5–1.0 µg/µL.

E. coli strain MC1061, carrying the λ-Red recombinase expression plasmid pKD46 (amp$^R$) (Datsenko and Wanner, supra; SEQ ID NO:55), was used as a host strain for the chromosomal integration of the PCR fragments. The strain was constructed by transformation of E. coli strain MC1061 with the λ-Red recombinase expression plasmid, pKD46 (amp$^R$). The λ-Red recombinase in pKD46 is comprised of three genes exo, bet, and gam expressed under the control of an arabinose-inducible promoter. Transformants were selected on 100 µg/mL of ampicillin LB plates at 30° C.

For transformation, electroporation was performed using 5–10 µg of the purified PCR products carrying the kanamycin marker and phage T5 promoter. Approximately one-half of the cells transformed were spread on LB plates containing 25 µg/mL of kanamycin in order to select antibiotic-resistant transformants. After incubating the plate at 37° C. overnight, antibiotic-resistant transformants were selected as follows: 10 colonies of kan-P$_{T5}$-dxs, 12 colonies of kan-P$_{T5}$-idi, and 10 colonies of kan-P$_{T5}$-ygbBygbP.

PCR analysis was used to screen the selected kan-P$_{T5}$ kanamycin-resistant transformants for integration of both the kanamycin selectable marker and the phage T5 promoter (P$_{T5}$) in the correct location on the E. coli chromosome. For PCR, a colony was resuspended in 50 µL of PCR reaction mixture containing 200 µM dNTPs, 2.5 U AmpliTaq™ (Applied Biosytems), and 0.4 µM of specific primer pairs. Test primers were chosen to match sequences of the regions located in the kanamycin (5'-primer) and the early coding-region of each isoprenoid gene (3'-primer). The PCR reaction was performed as described above. Chromosomal integration of kan-P$_{T5}$ upstream of each isoprenoid gene was confirmed by PCR analysis. The resultant E. coli strains carrying each kan-P$_{T5}$-isoprenoid gene fusion on the chromosome were used for stacking multiple kan-P$_{T5}$-isoprenoid gene fusions in parallel on the chromosome in a combinatorial approach as described in Examples 8–10.

Example 8

Preparation of P1 Lysate Made from E. coli Kan-P$_{T5}$-dxs, E. coli Kan-P$_{T5}$-idi and E. coli Kan-P$_{T5}$-ygbBygbP P1 lysates of the E. coli kan-P$_{T5}$-dxs, E. coli kan-P$_{T5}$-idi and E. coli kan-P$_{T5}$-ygbBygbP strains were prepared by infecting a growing culture of bacteria with the P1 phage and allowing the cells to lyse (U.S. Ser. No. 10/735442). For P1 infection, each strain was inoculated in 4 mL LB medium with 25 µg/mL of kanamycin, grown at 37° C. overnight, and then sub-cultured with 1:100 dilution of an overnight culture in 10 mL LB medium containing 5 mM CaCl$_2$. After 20–30 min of growth at 37° C., 10$^7$ P1$_{vir}$ phages were added. The cell-phage mixture was aerated for 2–3 hr at 37° C. until lysed, several drops of chloroform were added and the mixture vortexed for 30 sec and incubated for an additional 30 min at room temp. The mixture was then centrifuged for 10 min at 4500 rpm, and the supernatant transferred into a new tube to which several drops of chloroform were added. The lysates were stored at 4° C.

Example 9

Construction of E. coli P$_{T5}$-dXS P$_{T5}$-idi Strain for Increased β-carotene Production In order to create a bacterial strain capable of increased carotenoid production, P$_{T5}$-dXs and P$_{T5}$-idi genes were chromosomally stacked into E. coli MG1655, capable of producing β-carotene, by P1 transduction in combination with the FLP site-specific recombinase.

P1 lysate made from the E. coli kan-P$_{T5}$-dxs strain was transduced into the recipient strain, E. coli MG1655 containing a β-carotene biosynthesis expression plasmid pPCB15 (cam$^R$)(SEQ ID NO:54). The plasmid pPCB15 (cam$^R$) contains the carotenoid biosynthesis gene cluster (crtEXYIB) from *Pantoea Stewartii* (ATCC no. 8199). The pPCB15 plasmid was constructed from ligation of SmaI digested pSU18 (Bartolome et al., Gene, 102:75–78 (1991)) vector with a blunt-ended PmeI/NotI fragment carrying crtEXYIB from pPCB13 (Example 1). The *E. coli* MG1655 pPCB15 recipient cells were grown to mid-log phase (1–2× 10$^8$ cells/mL) in 4 mL LB medium with 25 μg/mL of chloramphenicol at 37° C. Cells were spun down for 10 min at 4500 rpm and resuspended in 2 mL of 10 mM MgSO$_4$ and 5 mM CaCl$_2$. Recipient cells (100 μL) were mixed with 1 μL, 2 μL, 5 μL, or 10 μL of P1 lysate stock (10$^7$ pfu/μL) made from the *E. coli* kan-P$_{T5}$-dxs strain and incubated at 30° C. for 30 min. The recipient cell-lysate mixture was spun down at 6500 rpm for 30 sec, resuspended in 100 μL of LB medium with 10 mM of sodium citrate, and incubated at 37° C. for 1 h. Cells were plated on LB plates containing both 25 μg/mL of kanamycin and 25 μg/mL of chloramphenicol in order to select for antibiotic-resistant transductants, and incubated at 37° C. for 1 or 2 days. Sixteen transductants were selected.

To eliminate kanamycin selectable marker from the chromosome, a FLP recombinase expression plasmid pCP20 (amp$^R$) (ATCC PTA-4455; Cherepanov and Wackernagel, *Gene*, 158:9–14 (1995)), which has a temperature-sensitive replication of origin, was transiently transformed into one of the kanamycin-resistant transductants by electroporation. Cells were spread onto LB agar containing 100 μg/mL of ampicillin and 25 μg/mL of chloramphenicol LB plates, and grown at 30° C. for 1 day. Colonies were picked and streaked on 25 μg/mL of chloramphenicol LB plates without ampicillin antibiotics and incubated at 43° C. overnight. Plasmid pCP20 has a temperature sensitive origin of replication and was cured from the host cells by culturing cells at 43° C. The colonies were tested for ampicillin and kanamycin sensitivity to test loss of pCP20 and kanamycin selectable marker by streaking colonies on 100 μg/mL of ampicillin LB plate or 25 μg/mL of kanamycin LB plate. Elimination of the kanamycin selectable marker from the *E. coli* chromosome was confirmed by PCR analysis (Example 7). The selected colonies were resuspended in 50 μL of PCR reaction mixture containing 200 μM dNTPs, 2.5 U AmpliTaq™ (Applied Biosytems), and 0.4 μM of different combination of specific primer pairs, T-kan (5'-ACCGGATAT-CACCACTTAT CTGCTC-3'; SEQ ID NO:28) and B-dxs (5'-TGGCMCAGTCGTAGCTCCTGGG TGG-3'; SEQ ID NO:29), T-T5 (5'-TMCCTATAAAAATAGGCGTATCAC-GAGG CCC-3'; SEQ ID NO:30) and B-dxs. Test primers were chosen to amplify regions located either in the kanamycin or the phage T5 promoter and the 5' region of dxs gene. The PCR indicated the elimination of the kanamycin selectable marker from the *E. coli* chromosome. The presence of the phage T5 promoter fragment upstream of the dxs gene was confirmed based on the production of a PCR product of the expected size (229 bp). In this manner the *E. coli* P$_{T5}$-dxs strain was constructed.

In order to further stack kan-P$_{T5}$-idi on the chromosome of *E. coli* P$_{T5}$-dxs, P1 lysate made on *E. coli* kan-P$_{T5}$-idi strain was transduced into the recipient strain, *E. coli* P$_{T5}$-dxS, as described above. Approximately 450 kanamycin-resistance transductants were selected. After transduction, the kanamycin selectable marker was eliminated from the chromosome as described above, yielding *E. coli* P$_{T5}$-dXs P$_{T5}$-idi strain (WS100).

For the *E. coli* P$_{T5}$-dxs P$_{T5}$-idi strain the correct integration of the is phage T5 promoter upstream of dxs and idi genes on the *E. coli* chromosome, and elimination of the kanamycin selectable marker were confirmed by PCR analysis. A colony of the *E. coli* P$_{T5}$-dxs P$_{T5}$-idi strain was tested by PCR with different combination of specific primer pairs, T-kan and B-dxs, T-T5 and B-dxs, T-kan and B-idi (CAGC-CAACTGGAGAACGCGAGATGT; SEQ ID NO:31), and T-T5 and B-idi. Test primers were chosen to amplify regions located either in the kanamycin or the phage T5 promoter and the downstream region of the chromosomal integration site. The PCR reaction was performed as described above. The PCR results indicated the elimination of the kanamycin selectable marker from the *E. coli* chromosome. The chromosomal integration of the phage T5 promoter fragment upstream of the dxs and idi gene was confirmed based on the expected sizes of PCR products, 229 bp and 274 bp, respectively.

Example 10

Production of Isorenieratene by *E.coli* Fermentation

The plasmids pBHR-crt+ (kan$^R$) and pTrcHis2-TOPO-crtU (amp$^R$) were transformed into electrocompetent *E. coli* MG1655 P$_{T5}$-dxs, P$_{T5}$-idi cells (WS100), resulting in the *E. coli* strain DPR676 (ATCC # PTA-5136). The pBHR-crt+ plasmid was constructed as described in Example 5.

DPR676 was pre-cultured for seeding a fermentor in 500 mL of 2× YT medium (10 g/L yeast extract, 16 g/L tryptone, 20 g/L glucose and 10 g/L NaCl) in a 2-L Erlenmeyer flask, containing 100 mg/mL ampicillin and 50 mg/mL kanamycin. The seed culture was started from a single colony on LB agar+100 mg/mL ampicillin and 50 mg/mL kanamycin. The seed culture was grown at 35° C. in a shaker at 300 rpm until OD$X_{\lambda=550}$ reached 3.62. This initial culture was used to seed the fermentor.

The following components were sterilized together in the fermentor vessel: 10 mL/L Modified Balch's Trace element solution, 5 g/L yeast extract, 0.2 g/L CaCl$_2$.2H$_2$O, 0.3 g/L ferric ammonium citrate, 2 g/L MgSO$_4$.7H$_2$O, 2 g/L citric acid, 7.5 g/L KH$_2$PO$_4$, 1.2 g/L sulfuric acid and 0.8 mL/L Mazu DF204 as an antifoam. After sterilization, the pH was raised to 6.8 with 40% NH$_4$OH. The concentration of ampicillin was brought to 100 g/L and the concentration of kanamycin was brought to 50 mg/mL. Two hundred forty six grams of a 65% glucose solution was added post vessel sterilization to give a 20 g/L initial concentration in the fermentor. Modified Balch's Trace elements contained 4 g/L citric acid.H$_2$O, 3 g/L MnSO$_4$.H$_2$O, 1 g/L NaCl, 0.1 g/L FeSO$_4$.7H$_2$O, 0.1 g/L ZnSO$_4$.7H$_2$O, 0.001 g/L CuSO$_4$.5H$_2$O, 0.001 g/L H$_3$BO$_3$, and 0.001 g/L NaMoO$_4$.2H$_2$O. After inoculation, the volume was 8 L and the glucose concentration was 20 g/L.

A 10 L stirred tank fermentor was prepared with the medium described above. Eight hours into the fermentation run, when the glucose concentration fell below 1 g/L, a 10% fructose bolus was added at a rate of 20 mL/min until 1 L was added. The temperature was controlled at 37° C. and the pH was maintained at 6.8 with NH$_4$OH and H$_3$PO$_4$. Backpressure was manually controlled at 0.5 bar (7.5 psig; approximately 51.7 kPa)). The dissolved oxygen set point was 10%. Nine liters of cell culture was harvested and concentrated to 375 mL of cell slurry.

A 1 mL volume of the cell slurry was used for HPLC analysis as described in Example 5. The results indicated that total extracted pigment contained 63% of isorenieratene, 16% of β-isorenieratene and 21% of β-carotene. A total of 31.4 mg of isorenieratene and 8 mg of β-isorenieratene were estimated to have been produced from the 9 liters of cell culture obtained in the fermentation.

Example 11

Construction of E. coli $P_{T5}$-dxs $P_{T5}$-idi $P_{T5}$-ygbBygbP Strain for Increased β-carotene Production In order to create a bacterial strain capable of increased carotenoid production, the $P_{T5}$-ygbBygbP construct was further stacked into the E. coli $P_{T5}$-dxs $P_{T5}$-idi strain by P1 transduction in combination with the FLP recombination system (Examples 7–9). P1 lysate made using the E. coli kan-$P_{T5}$-ygbBygbP strain was transduced into the recipient strain, E. coli kan-$P_{T5}$-dxs kan-$P_{T5}$-idi containing a β-carotene biosynthesis expression plasmid pPCB15 (cam$^R$), as described in Example 9. Twenty-one kanamycin-resistance transductants were selected. The kanamycin selectable marker was eliminated from the chromosome of the transductants using a FLP recombinase expression system, yielding E. coli strain $P_{T5}$-dxs $P_{T5}$-idi $P_{T5}$-ygbBygbP.

The correct chromosomal integration of the phage T5 promoter upstream of dxs, idi and ygbBP genes in E. coli $P_{T5}$-dxs $P_{T5}$-idi $P_{T5}$-ygbBygbP and the elimination of the kanamycin selectable marker were confirmed by PCR analysis. A colony of the E. coli $P_{T5}$-dxs $P_{T5}$-idi $P_{T5}$-ygbBygbP strain was tested by PCR with different combination of specific primer pairs, T-kan and B-dxs, T-T5 and B-dxs, T-kan and B-idi, T-T5 and B-idi, T-kan and B-ygb (5'-CCAGCAGCGCATGCACCGAGTGTTC-3')(SEQ ID NO:32), and T-T5 and B-ygb. Test primers were chosen to amplify regions located either in the kanamycin or the phage T5 promoter and the downstream region of the chromosomal integration site. The PCR reaction was performed as described in Example 9. The PCR results indicated the elimination of the kanamycin selectable marker from the E. coli chromosome. The chromosomal integration of the phage T5 promoter fragment upstream of the dxs, idi, and ygbBygbP genes was confirmed based on the expected sizes of the PCR products, 229 bp, 274 bp, and 296 bp, respectively.

Example 12

Chromosomal Integration of the P. stewartii crtE Gene in E.coli

This example describes the chromosomal integration of P. stewartli crtE and crtIB genes into the region located at 81.2 min of E. coli chromosome by integration of P. stewartli crtE (SEQ ID NO:1) and P. stewartii crtIB (SEQ ID NOs:7 and 9). The crtE, crtI, and crtB genes encode geranylgeranyl pyrophosphate synthase, phytoene dehydrogenase, and phytoene synthase, respectively. These genes are involved in the carotenoid biosynthetic pathway (FIG. 2).

The linear DNA fragment containing fused kanamycin selectable marker-phage T5 promoter is synthesized by PCR from pSUH5 (FIG. 5; SEQ ID NO:56) with primer pairs, T1 (crtE) (5'-AGCCGTCGCAGGAGGAACAACTCATATCATCATTG CGATCTCGACCG TCTTGAGCGATTGTGTAG-3'; SEQ ID NO:33) which contains an h10 homology arm (underlined, 45 bp) chosen to match a sequence in the inter-operon region located at 81.2 min of E. coli chromosome and a priming sequence (20 bp) and B1(crtE) (5'-TGAACGTGTTTTTTTGCGCAGACCGTCATAGTTAA TTTCTCCTCTTTAA TG-3'; SEQ ID NO:34) which contains an h11 homology arm (underlined, 29 bp) chosen to match a sequence in the downstream region of the crtE start codon and a priming sequence (22 bp)(FIG. 4). The linear DNA fragment containing P. stewartii crtE gene was synthesized by PCR from pPCB15 with primer pairs, T2(crtE) (5'-ACAGAATTCATTAAAGAGGAGAAATTAACTATGAC GGTCTGCGCAAAA AAACACG-3'; SEQ ID NO:35) which contains an h8 homology arm (underlined, 30 bp) chosen to match a sequence in the 3'-end region of the fused kanamycin selectable marker-phage T5 promoter and a priming sequence (25 bp) and B2(crtE) (5'-AGAATGACCAGCTGGATGCATTATCTTTATTTGGAT CATTGAGGGTTA ACTGACGGCAGCGAGTT-3';SEQ ID NO:36) which contains an h12 homology arm (underlined, 45 bp) chosen to match a sequence in the inter-operon region located at 81.2 min of the E. coli chromosome and a priming sequence (20 bp). The underlined sequences illustrate each respective homology arm, while the remainder is the priming sequences for hybridization to complementary nucleotide sequences on the template DNA for the PCR reaction. The two resultant PCR fragments were the fused kanamycin selectable marker-phage T5 promoter containing the homology arms (h10 and h11) and the P. stewartii crtE gene containing the homology arms (h8 and h12) as illustrated in FIG. 4.

The PCR amplification, purification, and electro-transformation were performed as described in Example 6 except that the transformation of the reporter plasmid pPCB15 into the E coli. strain was omitted. Both fused kanamycin marker-phage T5 promoter PCR products (5–10 μg) and the P. stewartii crtE PCR products (5–10 μg) were co-transformed into an E. coli host strain (MC1061) expressing the λ-Red recombinase system. Transformants were selected on 25 μg/mL of kanamycin LB plates at 37° C. After incubating the plate at 37 ° C. overnight, two kan$^R$-resistant transformants were selected.

Two kan$^R$ resistant transformants were PCR analyzed with T10 (5'-CCATGACCCTACATTGTGATCTATAG-3'; SEQ ID NO:37) and T13 (5'-GGAACCATTGAACTG-GACCCTAACG-3'; SEQ ID NO:38) primer pair. PCR analysis was performed under same PCR reaction condition as described in Example 9. PCR testing with T10/T13 on two transformants exhibited the expected size of 2883 bp based on a 1% agarose gel, indicating the correct integration of the fused kanamycin selectable marker-phage T5 promoter DNA fragment along with P. stewartji crtE gene into the inter-operon region located at 81.2 min of E. coli chromosome, yielding E. coli kan-$P_{T5}$-crtE (FIG. 4).

Example 13

Chromosomal Integration of the P. stewartii crtI and crtB Genes in E.coli $P_{T5}$-crtE for Construction of E. coli $P_{T5}$-crtEIB The linear DNA fragment containing the fused kanamycin selectable marker-phage T5 promoter-P. stewartii crtE gene was synthesized by PCR from the genomic DNA of E. coli $P_{T5}$-crtE with primer pairs, T10 (SEQ ID NO:37) which contains a priming sequence (26 bp) corresponding to the 162 bases in the upstream region of the integration site of the fused kanamycin selectable marker-phage T5 promoter-crtE gene in E. coli and B1 (crtIB) (5'-

TCCTCCAGCATTAAGCCTGCCGTCGCCTTTTAACTG ACGGCAGCG AGTTTTTTGTC-3'; SEQ ID NO:39) which contains an h13 homology arm (underlined, 29 bp) chosen to match sequences in the downstream region of the crtI start codon and a priming sequence (27 bp). The linear DNA fragment containing *P. stewartii* crtIB gene was synthesized by PCR from pPCB15 with primer pairs, T2(crtIB) (5'-TTTGACAAAAAACTCGCTGCCGTCAGTTAAAAGGC GACGGCAGGCTT AATGCTG-3'; SEQ ID NO:40) which contains a h14 homology arm (FIG. 4) (underlined, 30 bp) chosen to match a sequence in the 3'-end region of the fused kanamycin selectable marker-phage T5 promoter-crtE gene and a priming sequence (24 bp) and B2(crtIB) (5'-AGAATGACCAGCTGGATGCATTATCTTTATTTGGAT CATTGAGGGCTA GATCGGGCGCTGCCAGA-3'; SEQ ID NO:41) which contains a h12 homology arm (underlined, 45 bp) (FIG. 4) chosen to match a sequence in the inter-operon region located at 81.2 min of the *E. coli* chromosome and a priming sequence (20 bp). The underlined sequences illustrate each respective homology arm, while the remainder is the priming sequences for hybridization to complementary nucleotide sequences on the template DNA for the PCR reaction. The two resultant PCR fragments were the fused kanamycin selectable marker-phage T5 promoter-*P. stewartli* crtE gene containing the homology region (162 bp) at the 5'-end and homology, arm (h13), and the *P. stewartii* crtIB genes containing the homology arms (h14 and h12) as illustrated in FIG. 4.

The PCR amplification, purification, and electro-transformation were performed as described above except for the omission of transforming the host cell with the reporter plasmid, pPCB15. Both the fused kanamycin selectable marker-phage T5 promoter-*P. stewartii* crtE gene PCR products (5–10 μg) and the *P. stewartii* crtIB PCR products (5–10 μg) were co-transformed into an *E. coli* host cell expressing the λ-Red recombinase system by electroporation as previously described. Transformants were selected on 25 μg/mL of kanamycin LB plates at 37° C. After incubating the plate at 37° C. overnight, one kan$^R$ resistant transformant was selected. The selected kan$^R$ resistant transformant was PCR analyzed with different combinations of specific primer pairs, T10 and T2 (5'-CAGTCATAGCCGAATAGCCT-3'; SEQ ID NO:42), T2(T5) (5'-CGGTGCCCTGAAT-GAACTGC-3'; SEQ ID NO:43) and T12 (5'-CTA-GATCGGGCGCTGCCAGAGATGA-3'; SEQ ID NO:44), T11(5'-ACACGTTCACCTTACTGGCATTTCG-3'; SEQ ID NO:45) and T13, and T10 and T13. Test primers were chosen to amplify sequences located either in the vicinity of the integration region of the kanamycin selectable marker-phage T5 promoter-crtE fragment or the crtIB genes. PCR analysis was performed under same PCR reaction condition as described in Example 9. PCR test with T10 and T2, T2(T5) and T12, T11 and T13, and T10 and T13 exhibited the expected sizes, 676 bp, 3472 bp, 3478 bp and 5288 bp on 1% agarose gel, respectively. The elimination of the kanamycin selectable marker was confirmed by PCR fragment analysis. PCR fragment analysis with primer pair T10 and T2 exhibited no product formation as expected. PCR analysis with primer pairs T2(T5) and T12, T11 and T13, and T10 and T13 exhibited the expected PCR product sizes of 3472 bp, 3478 bp, and 3895 bp on 1% agarose gel, respectively. The results indicated the correct integration of the fused kanamycin selectable marker-phage T5 promoter-*P. stewartii* crtE gene DNA fragment and *P. stewartii* crtIB genes into the inter-operon region located at 81.2 min of *E. coli* chromosome, yielding *E. coli* kan-P$_{T5}$-crtEIB.

The functional expression of the constructed *E. coli* kan-PT$_5$-crtEIB was tested by the synthesis of lycopene based on the production of pink pigment. After extracting lycopene with acetone, the lycopene production by *E. coli* P$_{T5}$-crtEIB strain also was confirmed by measuring the spectra of lycopene with its characteristic λ$_{max}$ peaks at 444, 470, and 502 nm.

Example 14

Construction of *E. coli* P$_{T5}$-dxs P$_{T5}$-idi P$_{T5}$-vbB gbP P$_{T5}$-CrtEIB Strain The kan-P$_{T5}$-*P. stewartii* crtEIB was chromosomally stacked into *E. coli* P$_{T5}$-dxs P$_{T5}$-idi P$_{T5}$-ygbBygbP strain. The kan P$_{T5}$-*P. stewartii* crtEIB was chromosomally integrated into *E. coli* P$_{T5}$-dxs P$_{T5}$-idi P$_{T5}$-ygbBygbP strain by P1 transduction in combination. P1 lysate made on *E. coli* kan P$_{T5}$-P. stewartii crtEIB strain was transduced into the recipient strain, *E. coli* P$_{T5}$-dxs P$_{T5}$-idi P$_{T5}$-ygbBygbP as described in Example 9. Sixteen kanamycin-resistance transductants were selected. The kanamycin selectable marker was eliminated from the chromosome of the transductants using a FLP recombinase expression system, yielding *E. coli* P$_{T5}$-dxs P$_{T5}$-idi P$_{T5}$-ygbBygbP P$_{T5}$-*P. stewartii* crtEIB (WS156). The elimination of the kanamycin selectable marker was confirmed by PCR fragment analysis. PCR fragment analysis with primer pair T10 and T2 exhibited no product formation as expected.

Example 15

Isolation and Characterization of *Rhodococcus erythropolis* Strain AN12

U.S. Ser. No. 10/292577 (corresponding to WO 03/044205) describes the isolation of strain AN12 of *Rhodococcus erythropolis* on the basis of being able to grow on aniline as the sole source of carbon and energy. Analysis of a 16S rRNA gene sequence indicated that strain AN12 was related to high G+C gram positive bacteria belonging to the genus *Rhodococcus*.

Briefly, bacteria that grew on aniline were isolated from an enrichment culture. The enrichment culture was established by inoculating 1 mL of activated sludge into 10 mL of S12 medium (10 mM ammonium sulfate, 50 mM potassium phosphate buffer (pH 7.0), 2 mM MgCl$_2$, 0.7 mM CaCl$_2$, 50 μM MnCl$_2$, 1 μM FeCl$_3$, 1 μM ZnCl$_3$, 1.72 μM CuSO$_4$, 2.53 μM CoCl$_2$, 2.42 μM Na$_2$MoO$_2$, and 0.0001% FeSO$_4$) in a 125 mL screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 mL of the culture with the same volume of S12 medium. Bacteria that utilized aniline as a sole source of carbon and energy were isolated by spreading samples of the enrichment culture onto S12 agar. Aniline (5 μL) was placed on the interior of each petri dish lid. The petri dishes were sealed with parafilm and incubated upside down at room temperature (approximately 25° C.). Representative bacterial colonies were then tested for the ability to use aniline as a sole source of carbon and energy. Colonies were transferred from the original S12 agar plates used for initial isolation to new S12 agar plates and supplied with aniline on the interior of each petri dish lid. The petri dishes were sealed with parafilm and incubated upside down at room temperature (approximately 25° C.).

The 16S rRNA genes of each isolate were amplified by PCR and analyzed as follows. Each isolate was grown on R2A agar (Difco Laboratories, Bedford, Mass.). Several colonies from a culture plate were suspended in 100 μl of water. The mixture was frozen and then thawed once. The 16S rRNA gene sequences were amplified by PCR using a commercial kit according to the manufacturer's instructions (Perkin Elmer) with primers HK12 (5'-GAGTTTGATC-CTGGCTCAG-3') (SEQ ID NO:46) and HK13 (5'-TACCT-TGTTACGACTT-3') (SEQ ID NO:47). PCR was performed in a Perkin Elmer GeneAmp 9600 (Norwalk, Conn.). The samples were incubated for 5 min at 94° C. and then cycled 35 times at 94° C. for 30 sec, 55° C. for 1 min, and 72° C. for 1 min. The amplified 16S rRNA genes were purified using a commercial kit according to the manufacturer's instructions (QIAquick PCR Purification Kit, Qiagen, Valencia, Calif.) and sequenced on an automated ABI sequencer. The sequencing reactions were initiated with primers HK12, HK13, and HK14 (5'-GTGCCAG-CAGYMGCGGT-3') (SEQ ID NO:48, where Y=C or T, M=A or C). The 16S rRNA gene sequence of each isolate was used as the query sequence for a BLAST search (Altschul et al., *Nucleic Acids Res.*, 25:3389–3402(1997)) of GenBank® for similar sequences.

A 16S rRNA gene of strain AN12 was sequenced and compared to other 16S rRNA sequences in the GenBank® sequence database. The 16S rRNA gene sequence from strain AN12 was at least 98% similar to the 16S rRNA gene sequences of high G+C gram positive bacteria belonging to the genus *Rhodococcus*.

Example 16

Identification of Lycoiene Cyclases from *Rhodococcus* and *Deinococcus*

The ORF for crtL was identified by conducting BLAST (Basic Local Alignment Search Tool; Altschul, S. F., et al., *J. Mol. Biol.*, 215:403–410 (1993)) searches for similarity to sequences contained in the BLAST "nr" database (comprising all non-redundant (nr) GenBank® CDS translations, sequences derived from the 3-dimensional structure Brookhaven Protein Data Bank, the SWISS-PROT protein sequence database, EMBL, and DDBJ databases). The genomic sequence of *Rhodococcus erythropolis* AN12 was analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Altschul et al., *Nucleic Acid Res.*, 25:3389–3402 (1997)) provided by the NCBI.

Results from the BLAST analysis indicated that the lycopene β-cyclase from *Rhodococcus erythropolis* strain AN12 (SEQ ID NOs:49 and 50) shared homology to a putative carotenoid lycopene β-cyclase DR0801 (Gen-Bank® ID MF10377.1) from *Deinococcus radiodurans* strain R1 (percent identity=31%, percent similarity=45%, E-value 2e-37) and other CrtL-type of lycopene β-cyclases from plants (U.S. Ser. No. 10/292577).

Example 17

Production of Chlorobactene in *E. coli* using the Optimized CrtU

To demonstrate that the optimized crtU could be used in *E. coli* to synthesize other aryl-carotenoids in addition to isorenieratene, Applicants chose to synthesize chlorobactene by expressing the optimized crtU in *E. coli* producing γ-carotene. *E. coli* strains had been constructed that contained a single copy of the carotenoid pathway gene(s) expressed under phage T5 promoter on the chromosome. *E. coli* PT5-dxs, PT5-idi, PT5-ygbBygbP, PT5-crtEIB (WS156) showed darker pink color and produced lycopene. The γ-carotene producing strain was constructed by expressing an asymmetric lycopene cyclase, crtL (SEQ ID NOs:49 and 50) in WS156 strain. The crtL gene was PCR amplified from genomic DNA of *Rhodococcus erythropolis* AN12, using forward primer crtL(an12)_F (5'-gaattcaggaggaataaaccatgagcacactcgactcctcc-3';SEQ ID NO:51) and reverse primer crtL(an12)_R (5'-caattgtcaccggaaaaacggcgc-3'; SEQ ID NO:52). Underlined part in the primers is EcoRI or Mfe I site and the bolded sequence indicates an artificial ribosome binding site. The 1157 bp PCR product was cloned in the pTrcHis2-TOPO cloning vector, resulted pDCQ185. The ~1.2 kb EcoR I fragment from pDCQ185 containing the crtL gene was ligated into the EcoR I site in pBHR1 vector (MoBiTec, Göttingen, Germany) to create pDCQ186, in which the crtL is expressed under the control of the chloramphenicol resistant gene promoter on the vector. WS156Kan$^S$ cells were transformed with pDCQ186. Transformants were grown in LB (Luria Broth) or TB (Terrific Broth) medium with 50 μg/mL kanamycin at 37° C. for 1 day and cells were harvested by centrifugation. Carotenoids were extracted from the cell pellets three times, each with 10 mL of acetone for 15 min at room temperature. The extracted pigments were dried under nitrogen and dissolved in 1 mL acetone. Each sample of 0.1 mL was used for HPLC analysis as described previously. The major pigment comprising 96% of the total carotenoids eluted at 13.6 min with absorption spectrum of (439), 463, 492 nm, which is characteristic of γ-carotene.

The crtU expressing plasmid pTrcHis2-TOPO-crtU was transformed into they-carotene producing strain WS156Kan$^s$ (pDCQ186). The transformants were grown at 37° C. for 1 day in 25 mL TB with 50 μg/mL kanamycin and 100 μg/mL ampicillin. Cells were harvested by centrifugation and carotenoids were extracted and analyzed by HPLC. A new pigment peak eluted at 10.7 min was observed which has the absorption spectrum of 437, 461, and 490 nm. This is identical to the characteristics of chlorobactene previously produced from *Rhodococcus*. The chlorobactene pigment comprised 10% of the total carotenoids from this strain.

What is claimed is:

1. A method for the production of aryl carotenoid compounds comprising:

(a) providing an *E. coli* host cell which comprises a cyclic carotenoid having at least one β-ionone ring selected from the group consisting of β-carotene and γ-carotene;

(b) transforming the *E. coli* host cell of (a) with a nucleic acid molecule that is a crtU gene selected from group consisting of SEQ ID NO: 18 and SEQ ID NO: 53 and encoding a carotene desaturase; said nucleic acid molecule being codon optimized for expression in the *E. coli* host cell; and (c) growing the transformed *E. coli* host cell of (b) under conditions whereby an aryl carotenoid, selected from the group consisting of isorenieratene, chlorobactene and β-isorenieratene is produced.

2. A method according to claim 1 wherein the cyclic carotenoid having a β-ionone ring is produced endogenously by the host cell.

3. A method according to claim 1 wherein the cyclic carotenoid having a β-ionone ring is provided exogenously to the host cell.

4. An *E. coli* codon optimized carotene desaturase gene selected from the group consisting of SEQ ID NO:18 and SEQ ID NO:53.

* * * * *

SEQUENCE LISTING

<160> NUMBER OF SEQ ID NOS: 57

<210> SEQ ID NO 1
<211> LENGTH: 912
<212> TYPE: DNA
<213> ORGANISM: Pantoea stewartii
<220> FEATURE:
<221> NAME/KEY: misc_feature
<222> LOCATION: (1)..(3)
<223> OTHER INFORMATION: Alternative start codon used. TTG encodes for methionine.

<400> SEQUENCE: 1

```
ttgacggtct gcgcaaaaaa acacgttcac cttactggca tttcggctga gcagttgctg      60
gctgatatcg atagccgcct tgatcagtta ctgccggttc agggtgagcg ggattgtgtg     120
ggtgccgcga tgcgtgaagg cacgctggca ccgggcaaac gtattcgtcc gatgctgctg     180
ttattaacag cgcgcgatct tggctgtgcg atcagtcacg ggggattact ggatttagcc     240
tgcgcggttg aaatggtgca tgctgcctcg ctgattctgg atgatatgcc ctgcatggac     300
gatgcgcaga tgcgtcgggg gcgtcccacc attcacacgc agtacggtga acatgtggcg     360
attctggcgg cggtcgcttt actcagcaaa gcgtttgggg tgattgccga ggctgaaggt     420
ctgacgccga tagccaaaac tcgcgcggtg tcggagctgt ccactgcgat ggcatgcag      480
ggtctggttc agggccagtt taaggacctc tcggaaggcg ataaaccccg cagcgccgat     540
gccatactgc taaccaatca gtttaaaacc agcacgctgt tttgcgcgtc aacgcaaatg     600
gcgtccattg cggccaacgc gtcctgcgaa gcgcgtgaga acctgcatcg tttctcgctc     660
gatctcggcc aggcctttca gttgcttgac gatcttaccg atggcatgac cgataccggc     720
aaagacatca atcaggatgc aggtaaatca acgctggtca atttattagg ctcaggcgcg     780
gtcgaagaac gcctgcgaca gcatttgcgc ctggccagtg aacacctttc cgcggcatgc     840
caaaacggcc attccaccac ccaactttt  attcaggcct ggtttgacaa aaaactcgct     900
gccgtcagtt aa                                                         912
```

<210> SEQ ID NO 2
<211> LENGTH: 303
<212> TYPE: PRT
<213> ORGANISM: Pantoea stewartii

<400> SEQUENCE: 2

```
Met Thr Val Cys Ala Lys Lys His Val His Leu Thr Gly Ile Ser Ala
1               5                   10                  15

Glu Gln Leu Leu Ala Asp Ile Asp Ser Arg Leu Asp Gln Leu Leu Pro
            20                  25                  30

Val Gln Gly Glu Arg Asp Cys Val Gly Ala Ala Met Arg Glu Gly Thr
        35                  40                  45

Leu Ala Pro Gly Lys Arg Ile Arg Pro Met Leu Leu Leu Thr Ala
    50                  55                  60

Arg Asp Leu Gly Cys Ala Ile Ser His Gly Leu Leu Asp Leu Ala
65                  70                  75                  80

Cys Ala Val Glu Met Val His Ala Ala Ser Leu Ile Leu Asp Asp Met
                85                  90                  95

Pro Cys Met Asp Asp Ala Gln Met Arg Arg Gly Arg Pro Thr Ile His
            100                 105                 110

Thr Gln Tyr Gly Glu His Val Ala Ile Leu Ala Ala Val Ala Leu Leu
```

```
                115                  120                 125
Ser Lys Ala Phe Gly Val Ile Ala Glu Ala Glu Gly Leu Thr Pro Ile
        130                 135                 140
Ala Lys Thr Arg Ala Val Ser Glu Leu Ser Thr Ala Ile Gly Met Gln
145                 150                 155                 160
Gly Leu Val Gln Gly Gln Phe Lys Asp Leu Ser Glu Gly Asp Lys Pro
                165                 170                 175
Arg Ser Ala Asp Ala Ile Leu Leu Thr Asn Gln Phe Lys Thr Ser Thr
                180                 185                 190
Leu Phe Cys Ala Ser Thr Gln Met Ala Ser Ile Ala Ala Asn Ala Ser
            195                 200                 205
Cys Glu Ala Arg Glu Asn Leu His Arg Phe Ser Leu Asp Leu Gly Gln
210                 215                 220
Ala Phe Gln Leu Leu Asp Asp Leu Thr Asp Gly Met Thr Asp Thr Gly
225                 230                 235                 240
Lys Asp Ile Asn Gln Asp Ala Gly Lys Ser Thr Leu Val Asn Leu Leu
                245                 250                 255
Gly Ser Gly Ala Val Glu Glu Arg Leu Arg Gln His Leu Arg Leu Ala
            260                 265                 270
Ser Glu His Leu Ser Ala Ala Cys Gln Asn Gly His Ser Thr Thr Gln
            275                 280                 285
Leu Phe Ile Gln Ala Trp Phe Asp Lys Lys Leu Ala Ala Val Ser
        290                 295                 300

<210> SEQ ID NO 3
<211> LENGTH: 1296
<212> TYPE: DNA
<213> ORGANISM: Pantoea stewartii
<220> FEATURE:
<221> NAME/KEY: CDS
<222> LOCATION: (1)..(1296)

<400> SEQUENCE: 3 atg agc cat ttt gcg gtg atc gca ccg ccc ttt ttc agc cat gtt cgc      48
Met Ser His Phe Ala Val Ile Ala Pro Pro Phe Phe Ser His Val Arg
1               5                   10                  15 gct ctg caa aac ctt gct cag gaa tta gtg gcc cgc ggt cat cgt gtt      96
Ala Leu Gln Asn Leu Ala Gln Glu Leu Val Ala Arg Gly His Arg Val
                20                  25                  30 acg ttt ttt cag caa cat gac tgc aaa gcg ctg gta acg ggc agc gat     144
Thr Phe Phe Gln Gln His Asp Cys Lys Ala Leu Val Thr Gly Ser Asp
            35                  40                  45 atc gga ttc cag acc gtc gga ctg caa acg cat cct ccc ggt tcc tta     192
Ile Gly Phe Gln Thr Val Gly Leu Gln Thr His Pro Pro Gly Ser Leu
        50                  55                  60 tcg cac ctg ctg cac ctg gcc gcg cac cca ctc gga ccc tcg atg tta     240
Ser His Leu Leu His Leu Ala Ala His Pro Leu Gly Pro Ser Met Leu
65                  70                  75                  80 cga ctg atc aat gaa atg gca cgt acc agc gat atg ctt tgc cgg gaa     288
Arg Leu Ile Asn Glu Met Ala Arg Thr Ser Asp Met Leu Cys Arg Glu
                85                  90                  95 ctg ccc gcc gct ttt cat gcg ttg cag ata gag ggc gtg atc gtt gat     336
Leu Pro Ala Ala Phe His Ala Leu Gln Ile Glu Gly Val Ile Val Asp
                100                 105                 110 caa atg gag ccg gca ggt gca gta gtc gca gaa gcg tca ggt ctg ccg     384
Gln Met Glu Pro Ala Gly Ala Val Val Ala Glu Ala Ser Gly Leu Pro
            115                 120                 125 ttt gtt tcg gtg gcc tgc gcg ctg ccg ctc aac cgc gaa ccg ggt ttg     432
```

```
                Phe Val Ser Val Ala Cys Ala Leu Pro Leu Asn Arg Glu Pro Gly Leu
                    130                 135                 140 cct ctg gcg gtg atg cct ttc gag tac ggc acc agc gat gcg gct cgg              480
Pro Leu Ala Val Met Pro Phe Glu Tyr Gly Thr Ser Asp Ala Ala Arg
145                 150                 155                 160 gaa cgc tat acc acc agc gaa aaa att tat gac tgg ctg atg cga cgt              528
Glu Arg Tyr Thr Thr Ser Glu Lys Ile Tyr Asp Trp Leu Met Arg Arg
                165                 170                 175 cac gat cgt gtg atc gcg cat cat gca tgc aga atg ggt tta gcc ccg              576
His Asp Arg Val Ile Ala His His Ala Cys Arg Met Gly Leu Ala Pro
            180                 185                 190 cgt gaa aaa ctg cat cat tgt ttt tct cca ctg gca caa atc agc cag              624
Arg Glu Lys Leu His His Cys Phe Ser Pro Leu Ala Gln Ile Ser Gln
        195                 200                 205 ttg atc ccc gaa ctg gat ttt ccc cgc aaa gcg ctg cca gac tgc ttt              672
Leu Ile Pro Glu Leu Asp Phe Pro Arg Lys Ala Leu Pro Asp Cys Phe
    210                 215                 220 cat gcg gtt gga ccg tta cgg caa ccc cag ggg acg ccg ggg tca tca              720
His Ala Val Gly Pro Leu Arg Gln Pro Gln Gly Thr Pro Gly Ser Ser
225                 230                 235                 240 act tct tat ttt ccg tcc ccg gac aaa ccc cgt att ttt gcc tcg ctg              768
Thr Ser Tyr Phe Pro Ser Pro Asp Lys Pro Arg Ile Phe Ala Ser Leu
                245                 250                 255 ggc acc ctg cag gga cat cgt tat ggc ctg ttc agg acc atc gcc aaa              816
Gly Thr Leu Gln Gly His Arg Tyr Gly Leu Phe Arg Thr Ile Ala Lys
            260                 265                 270 gcc tgc gaa gag gtg gat gcg cag tta ctg ttg gca cac tgt ggc ggc              864
Ala Cys Glu Glu Val Asp Ala Gln Leu Leu Leu Ala His Cys Gly Gly
        275                 280                 285 ctc tca gcc acg cag gca ggt gaa ctg gcc cgg ggc ggg gac att cag              912
Leu Ser Ala Thr Gln Ala Gly Glu Leu Ala Arg Gly Gly Asp Ile Gln
    290                 295                 300 gtt gtg gat ttt gcc gat caa tcc gca gca ctt tca cag gca cag ttg              960
Val Val Asp Phe Ala Asp Gln Ser Ala Ala Leu Ser Gln Ala Gln Leu
305                 310                 315                 320 aca atc aca cat ggt ggg atg aat acg gta ctg gac gct att gct tcc             1008
Thr Ile Thr His Gly Gly Met Asn Thr Val Leu Asp Ala Ile Ala Ser
                325                 330                 335 cgc aca ccg cta ctg gcg ctg ccg ctg gca ttt gat caa cct ggc gtg             1056
Arg Thr Pro Leu Leu Ala Leu Pro Leu Ala Phe Asp Gln Pro Gly Val
            340                 345                 350 gca tca cga att gtt tat cat ggc atc ggc aag cgt gcg tct cgg ttt             1104
Ala Ser Arg Ile Val Tyr His Gly Ile Gly Lys Arg Ala Ser Arg Phe
        355                 360                 365 act acc agc cat gcg ctg gcg cgg cag att cga tcg ctg ctg act aac             1152
Thr Thr Ser His Ala Leu Ala Arg Gln Ile Arg Ser Leu Leu Thr Asn
    370                 375                 380 acc gat tac ccg cag cgt atg aca aaa att cag gcc gca ttg cgt ctg             1200
Thr Asp Tyr Pro Gln Arg Met Thr Lys Ile Gln Ala Ala Leu Arg Leu
385                 390                 395                 400 gca ggc ggc aca cca gcc gcc gcc gat att gtt gaa cag gcg atg cgg             1248
Ala Gly Gly Thr Pro Ala Ala Ala Asp Ile Val Glu Gln Ala Met Arg
                405                 410                 415 acc tgt cag cca gta ctc agt ggg cag gat tat gca acc gca cta tga             1296
Thr Cys Gln Pro Val Leu Ser Gly Gln Asp Tyr Ala Thr Ala Leu
            420                 425                 430

<210> SEQ ID NO 4
<211> LENGTH: 431
<212> TYPE: PRT
```

<213> ORGANISM: Pantoea stewartii

<400> SEQUENCE: 4

Met Ser His Phe Ala Val Ile Ala Pro Pro Phe Phe Ser His Val Ar

-continued

```
Ala Gly Gly Thr Pro Ala Ala Ala Asp Ile Val Glu Gln Ala Met Arg
                405                 410                 415

Thr Cys Gln Pro Val Leu Ser Gly Gln Asp Tyr Ala Thr Ala Leu
            420                 425                 430

<210> SEQ ID NO 5
<211> LENGTH: 1149
<212> TYPE: DNA
<213> ORGANISM: Pantoea stewartii
<220> FEATURE:
<221> NAME/KEY: CDS
<222> LOCATION: (1)..(1149)

<400> SEQUENCE: 5 atg caa ccg cac tat gat ctc att ctg gtc ggt gcc ggt ctg gct aat      48
Met Gln Pro His Tyr Asp Leu Ile Leu Val Gly Ala Gly Leu Ala Asn
1               5                   10                  15 ggc ctt atc gcg ctc cgg ctt cag caa cag cat ccg gat atg cgg atc      96
Gly Leu Ile Ala Leu Arg Leu Gln Gln Gln His Pro Asp Met Arg Ile
            20                  25                  30 ttg ctt att gag gcg ggt cct gag gcg gga ggg aac cat acc tgg tcc     144
Leu Leu Ile Glu Ala Gly Pro Glu Ala Gly Gly Asn His Thr Trp Ser
        35                  40                  45 ttt cac gaa gag gat tta acg ctg aat cag cat cgc tgg ata gcg ccg     192
Phe His Glu Glu Asp Leu Thr Leu Asn Gln His Arg Trp Ile Ala Pro
    50                  55                  60 ctt gtg gtc cat cac tgg ccc gac tac cag gtt cgt ttc ccc caa cgc     240
Leu Val Val His His Trp Pro Asp Tyr Gln Val Arg Phe Pro Gln Arg
65                  70                  75                  80 cgt cgc cat gtg aac agt ggc tac tac tgc gtg acc tcc cgg cat ttc     288
Arg Arg His Val Asn Ser Gly Tyr Tyr Cys Val Thr Ser Arg His Phe
                85                  90                  95 gcc ggg ata ctc cgg caa cag ttt gga caa cat tta tgg ctg cat acc     336
Ala Gly Ile Leu Arg Gln Gln Phe Gly Gln His Leu Trp Leu His Thr
            100                 105                 110 gcg gtt tca gcc gtt cat gct gaa tcg gtc cag tta gcg gat ggc cgg     384
Ala Val Ser Ala Val His Ala Glu Ser Val Gln Leu Ala Asp Gly Arg
        115                 120                 125 att att cat gcc agt aca gtg atc gac gga cgg ggt tac acg cct gat     432
Ile Ile His Ala Ser Thr Val Ile Asp Gly Arg Gly Tyr Thr Pro Asp
    130                 135                 140 tct gca cta cgc gta gga ttc cag gca ttt atc ggt cag gag tgg caa     480
Ser Ala Leu Arg Val Gly Phe Gln Ala Phe Ile Gly Gln Glu Trp Gln
145                 150                 155                 160 ctg agc gcg ccg cat ggt tta tcg tca ccg att atc atg gat gcg acg     528
Leu Ser Ala Pro His Gly Leu Ser Ser Pro Ile Ile Met Asp Ala Thr
                165                 170                 175 gtc gat cag caa aat ggc tac cgc ttt gtt tat acc ctg ccg ctt tcc     576
Val Asp Gln Gln Asn Gly Tyr Arg Phe Val Tyr Thr Leu Pro Leu Ser
            180                 185                 190 gca acc gca ctg ctg atc gaa gac aca cac tac att gac aag gct aat     624
Ala Thr Ala Leu Leu Ile Glu Asp Thr His Tyr Ile Asp Lys Ala Asn
        195                 200                 205 ctt cag gcc gaa cgg gcg cgt cag aac att cgc gat tat gct gcg cga     672
Leu Gln Ala Glu Arg Ala Arg Gln Asn Ile Arg Asp Tyr Ala Ala Arg
    210                 215                 220 cag ggt tgg ccg tta cag acg ttg ctg cgg gaa gaa cag ggt gca ttg     720
Gln Gly Trp Pro Leu Gln Thr Leu Leu Arg Glu Glu Gln Gly Ala Leu
225                 230                 235                 240 ccc att acg tta acg ggc gat aat cgt cag ttt tgg caa cag caa ccg     768
Pro Ile Thr Leu Thr Gly Asp Asn Arg Gln Phe Trp Gln Gln Gln Pro
```

-continued

```
                  245                 250                 255
caa gcc tgt agc gga tta cgc gcc ggg ctg ttt cat ccg aca acc ggc    816
Gln Ala Cys Ser Gly Leu Arg Ala Gly Leu Phe His Pro Thr Thr Gly
            260                 265                 270 tac tcc cta ccg ctc gcg gtg gcg ctg gcc gat cgt ctc agc gcg ctg    864
Tyr Ser Leu Pro Leu Ala Val Ala Leu Ala Asp Arg Leu Ser Ala Leu
        275                 280                 285 gat gtg ttt acc tct tcc tct gtt cac cag acg att gct cac ttt gcc    912
Asp Val Phe Thr Ser Ser Ser Val His Gln Thr Ile Ala His Phe Ala
    290                 295                 300 cag caa cgt tgg cag caa cag ggg ttt ttc cgc atg ctg aat cgc atg    960
Gln Gln Arg Trp Gln Gln Gln Gly Phe Phe Arg Met Leu Asn Arg Met
305                 310                 315                 320 ttg ttt tta gcc gga ccg gcc gag tca cgc tgg cgt gtg atg cag cgt   1008
Leu Phe Leu Ala Gly Pro Ala Glu Ser Arg Trp Arg Val Met Gln Arg
                325                 330                 335 ttc tat ggc tta ccc gag gat ttg att gcc cgc ttt tat gcg gga aaa   1056
Phe Tyr Gly Leu Pro Glu Asp Leu Ile Ala Arg Phe Tyr Ala Gly Lys
            340                 345                 350 ctc acc gtg acc gat cgg cta cgc att ctg agc ggc aag ccg ccc gtt   1104
Leu Thr Val Thr Asp Arg Leu Arg Ile Leu Ser Gly Lys Pro Pro Val
        355                 360                 365 ccc gtt ttc gcg gca ttg cag gca att atg acg act cat cgt tga       1149
Pro Val Phe Ala Ala Leu Gln Ala Ile Met Thr Thr His Arg
    370                 375                 380

<210> SEQ ID NO 6
<211> LENGTH: 382
<212> TYPE: PRT
<213> ORGANISM: Pantoea stewartii

<400> SEQUENCE: 6

Met Gln Pro His Tyr Asp Leu Ile Leu Val Gly Ala Gly Leu Ala Asn
1               5                   10                  15

Gly Leu Ile Ala Leu Arg Leu Gln Gln Gln His Pro Asp Met Arg Ile
            20                  25                  30

Leu Leu Ile Glu Ala Gly Pro Glu Ala Gly Gly Asn His Thr Trp Ser
        35                  40                  45

Phe His Glu Glu Asp Leu Thr Leu Asn Gln His Arg Trp Ile Ala Pro
    50                  55                  60

Leu Val Val His His Trp Pro Asp Tyr Gln Val Arg Phe Pro Gln Arg
65                  70                  75                  80

Arg Arg His Val Asn Ser Gly Tyr Tyr Cys Val Thr Ser Arg His Phe
                85                  90                  95

Ala Gly Ile Leu Arg Gln Gln Phe Gly Gln His Leu Trp Leu His Thr
            100                 105                 110

Ala Val Ser Ala Val His Ala Glu Ser Val Gln Leu Ala Asp Gly Arg
        115                 120                 125

Ile Ile His Ala Ser Thr Val Ile Asp Gly Arg Gly Tyr Thr Pro Asp
    130                 135                 140

Ser Ala Leu Arg Val Gly Phe Gln Ala Phe Ile Gly Gln Glu Trp Gln
145                 150                 155                 160

Leu Ser Ala Pro His Gly Leu Ser Ser Pro Ile Ile Met Asp Ala Thr
                165                 170                 175

Val Asp Gln Gln Asn Gly Tyr Arg Phe Val Tyr Thr Leu Pro Leu Ser
            180                 185                 190

Ala Thr Ala Leu Leu Ile Glu Asp Thr His Tyr Ile Asp Lys Ala Asn
```

-continued

```
            195                 200                 205
Leu Gln Ala Glu Arg Ala Arg Gln Asn Ile Arg Asp Tyr Ala Ala Arg
    210                 215                 220

Gln Gly Trp Pro Leu Gln Thr Leu Leu Arg Glu Glu Gln Gly Ala Leu
225                 230                 235                 240

Pro Ile Thr Leu Thr Gly Asp Asn Arg Gln Phe Trp Gln Gln Gln Pro
                245                 250                 255

Gln Ala Cys Ser Gly Leu Arg Ala Gly Leu Phe His Pro Thr Thr Gly
            260                 265                 270

Tyr Ser Leu Pro Leu Ala Val Ala Leu Ala Asp Arg Leu Ser Ala Leu
        275                 280                 285

Asp Val Phe Thr Ser Ser Val His Gln Thr Ile Ala His Phe Ala
    290                 295                 300

Gln Gln Arg Trp Gln Gln Gly Phe Phe Arg Met Leu Asn Arg Met
305                 310                 315                 320

Leu Phe Leu Ala Gly Pro Ala Glu Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Val Thr Asp Arg Leu Arg Ile Leu Ser Gly Lys Pro Pro Val
        355                 360                 365

Pro Val Phe Ala Ala Leu Gln Ala Ile Met Thr Thr His Arg
    370                 375                 380

<210> SEQ ID NO 7
<211> LENGTH: 1479
<212> TYPE: DNA
<213> ORGANISM: Pantoea stewartii
<220> FEATURE:
<221> NAME/KEY: CDS
<222> LOCATION: (1)..(1479)

<400> SEQUENCE: 7 atg aaa cca act acg gta att ggt gcg ggc ttt ggt ggc ctg gca ctg    48
Met Lys Pro Thr Thr Val Ile Gly Ala Gly Phe Gly Gly Leu Ala Leu
1               5                   10                  15 gca att cgt tta cag gcc gca ggt att cct gtt ttg ctg ctt gag cag    96
Ala Ile Arg Leu Gln Ala Ala Gly Ile Pro Val Leu Leu Leu Glu Gln
                20                  25                  30 cgc gac aag ccg ggt ggc cgg gct tat gtt tat cag gag cag ggc ttt   144
Arg Asp Lys Pro Gly Gly Arg Ala Tyr Val Tyr Gln Glu Gln Gly Phe
            35                  40                  45 act ttt gat gca ggc cct acc gtt atc acc gat ccc agc gcg att gaa   192
Thr Phe Asp Ala Gly Pro Thr Val Ile Thr Asp Pro Ser Ala Ile Glu
        50                  55                  60 gaa ctg ttt gct ctg gcc ggt aaa cag ctt aag gat tac gtc gag ctg   240
Glu Leu Phe Ala Leu Ala Gly Lys Gln Leu Lys Asp Tyr Val Glu Leu
65                  70                  75                  80 ttg ccg gtc acg ccg ttt tat cgc ctg tgc tgg gag tcc ggc aag gtc   288
Leu Pro Val Thr Pro Phe Tyr Arg Leu Cys Trp Glu Ser Gly Lys Val
                85                  90                  95 ttc aat tac gat aac gac cag gcc cag tta gaa gcg cag ata cag cag   336
Phe Asn Tyr Asp Asn Asp Gln Ala Gln Leu Glu Ala Gln Ile Gln Gln
            100                 105                 110 ttt aat ccg cgc gat gtt gcg ggt tat cga gcg ttc ctt gac tat tcg   384
Phe Asn Pro Arg Asp Val Ala Gly Tyr Arg Ala Phe Leu Asp Tyr Ser
        115                 120                 125 cgt gcc gta ttc aat gag ggc tat ctg aag ctc ggc act gtg cct ttt   432
```

```
                Arg Ala Val Phe Asn Glu Gly Tyr Leu Lys Leu Gly Thr Val Pro Phe
                    130                 135                 140 tta tcg ttc aaa gac atg ctt cgg gcc gcg ccc cag ttg gca aag ctg        480
Leu Ser Phe Lys Asp Met Leu Arg Ala Ala Pro Gln Leu Ala Lys Leu
145                 150                 155                 160 cag gca tgg cgc agc gtt tac agt aaa gtt gcc ggc tac att gag gat        528
Gln Ala Trp Arg Ser Val Tyr Ser Lys Val Ala Gly Tyr Ile Glu Asp
                165                 170                 175 gag cat ctt cgg cag gcg ttt tct ttt cac tcg ctc tta gtg ggg ggg        576
Glu His Leu Arg Gln Ala Phe Ser Phe His Ser Leu Leu Val Gly Gly
            180                 185                 190 aat ccg ttt gca acc tcg tcc att tat acg ctg att cac gcg tta gaa        624
Asn Pro Phe Ala Thr Ser Ser Ile Tyr Thr Leu Ile His Ala Leu Glu
        195                 200                 205 cgg gaa tgg ggc gtc tgg ttt cca cgc ggt gga acc ggt gcg ctg gtc        672
Arg Glu Trp Gly Val Trp Phe Pro Arg Gly Gly Thr Gly Ala Leu Val
    210                 215                 220 aat ggc atg atc aag ctg ttt cag gat ctg ggc ggc gaa gtc gtg ctt        720
Asn Gly Met Ile Lys Leu Phe Gln Asp Leu Gly Gly Glu Val Val Leu
225                 230                 235                 240 aac gcc cgg gtc agt cat atg gaa acc gtt ggg gac aag att cag gcc        768
Asn Ala Arg Val Ser His Met Glu Thr Val Gly Asp Lys Ile Gln Ala
                245                 250                 255 gtg cag ttg gaa gac ggc aga cgg ttt gaa acc tgc gcg gtg gcg tcg        816
Val Gln Leu Glu Asp Gly Arg Arg Phe Glu Thr Cys Ala Val Ala Ser
            260                 265                 270 aac gct gat gtt gta cat acc tat cgc gat ctg ctg tct cag cat ccc        864
Asn Ala Asp Val Val His Thr Tyr Arg Asp Leu Leu Ser Gln His Pro
        275                 280                 285 gca gcc gct aag cag gcg aaa aaa ctg caa tcc aag cgt atg agt aac        912
Ala Ala Ala Lys Gln Ala Lys Lys Leu Gln Ser Lys Arg Met Ser Asn
    290                 295                 300 tca ctg ttt gta ctc tat ttt ggt ctc aac cat cat cac gat caa ctc        960
Ser Leu Phe Val Leu Tyr Phe Gly Leu Asn His His His Asp Gln Leu
305                 310                 315                 320 gcc cat cat acc gtc tgt ttt ggg cca cgc tac cgt gaa ctg att cac        1008
Ala His His Thr Val Cys Phe Gly Pro Arg Tyr Arg Glu Leu Ile His
                325                 330                 335 gaa att ttt aac cat gat ggt ctg gct gag gat ttt tcg ctt tat tta        1056
Glu Ile Phe Asn His Asp Gly Leu Ala Glu Asp Phe Ser Leu Tyr Leu
            340                 345                 350 cac gca cct tgt gtc acg gat ccg tca ctg gca ccg gaa ggg tgc ggc        1104
His Ala Pro Cys Val Thr Asp Pro Ser Leu Ala Pro Glu Gly Cys Gly
        355                 360                 365 agc tat tat gtg ctg gcg cct gtt cca cac tta ggc acg gcg aac ctc        1152
Ser Tyr Tyr Val Leu Ala Pro Val Pro His Leu Gly Thr Ala Asn Leu
    370                 375                 380 gac tgg gcg gta gaa gga ccc cga ctg cgc gat cgt att ttt gac tac        1200
Asp Trp Ala Val Glu Gly Pro Arg Leu Arg Asp Arg Ile Phe Asp Tyr
385                 390                 395                 400 ctt gag caa cat tac atg cct ggc ttg cga agc cag ttg gtg acg cac        1248
Leu Glu Gln His Tyr Met Pro Gly Leu Arg Ser Gln Leu Val Thr His
                405                 410                 415 cgt atg ttt acg ccg ttc gat ttc cgc gac gag ctc aat gcc tgg caa        1296
Arg Met Phe Thr Pro Phe Asp Phe Arg Asp Glu Leu Asn Ala Trp Gln
            420                 425                 430 ggt tcg gcc ttc tcg gtt gaa cct att ctg acc cag agc gcc tgg ttc        1344
Gly Ser Ala Phe Ser Val Glu Pro Ile Leu Thr Gln Ser Ala Trp Phe
        435                 440                 445
```

```
cga cca cat aac cgc gat aag cac att gat aat ctt tat ctg gtt ggc      1392
Arg Pro His Asn Arg Asp Lys His Ile Asp Asn Leu Tyr Leu Val Gly
    450                 455                 460 gca ggc acc cat cct ggc gcg ggc att ccc ggc gta atc ggc tcg gcg      1440
Ala Gly Thr His Pro Gly Ala Gly Ile Pro Gly Val Ile Gly Ser Ala
465                 470                 475                 480 aag gcg acg gca ggc tta atg ctg gag gac ctg att tga                  1479
Lys Ala Thr Ala Gly Leu Met Leu Glu Asp Leu Ile
                485                 490
```

<210> SEQ ID NO 8
<211> LENGTH: 492
<212> TYPE: PRT
<213> ORGANISM: Pantoea stewartii

<400> SEQUENCE: 8

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Glu Gln
            20                  25                  30

Arg Asp Lys Pro Gly Gly Arg Ala Tyr Val Tyr Gln Glu Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Asp Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Ala Gln Leu Glu Ala Gln Ile Gln Gln
            100                 105                 110

Phe Asn Pro Arg Asp Val Ala Gly Tyr Arg Ala Phe Leu Asp Tyr Ser
        115                 120                 125

Arg Ala Val Phe Asn Glu Gly Tyr Leu Lys Leu Gly Thr Val Pro Phe
    130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Asn Gly Met Ile Lys Leu Phe Gln Asp Leu Gly Gly Glu Val Val Leu
225                 230                 235                 240

Asn Ala Arg Val Ser His Met Glu Thr Val Gly Asp Lys Ile Gln Ala
                245                 250                 255

Val Gln Leu Glu Asp Gly Arg Arg Phe Glu Thr Cys Ala Val Ala Ser
            260                 265                 270

Asn Ala Asp Val Val His Thr Tyr Arg Asp Leu Leu Ser Gln His Pro
        275                 280                 285

Ala Ala Ala Lys Gln Ala Lys Lys Leu Gln Ser Lys Arg Met Ser Asn
    290                 295                 300

Ser Leu Phe Val Leu Tyr Phe Gly Leu Asn His His Asp Gln Leu
305                 310                 315                 320
```

-continued

```
Ala His His Thr Val Cys Phe Gly Pro Arg Tyr Arg Glu Leu Ile His
                325                 330                 335
Glu Ile Phe Asn His Asp Gly Leu Ala Glu Asp Phe Ser Leu Tyr Leu
            340                 345                 350
His Ala Pro Cys Val Thr Asp Pro Ser Leu Ala Pro Glu Gly Cys Gly
        355                 360                 365
Ser Tyr Tyr Val Leu Ala Pro Val Pro His Leu Gly Thr Ala Asn Leu
    370                 375                 380
Asp Trp Ala Val Glu Gly Pro Arg Leu Arg Asp Arg Ile Phe Asp Tyr
385                 390                 395                 400
Leu Glu Gln His Tyr Met Pro Gly Leu Arg Ser Gln Leu Val Thr His
                405                 410                 415
Arg Met Phe Thr Pro Phe Asp Phe Arg Asp Glu Leu Asn Ala Trp Gln
            420                 425                 430
Gly Ser Ala Phe Ser Val Glu Pro Ile Leu Thr Gln Ser Ala Trp Phe
        435                 440                 445
Arg Pro His Asn Arg Asp Lys His Ile Asp Asn Leu Tyr Leu Val Gly
    450                 455                 460
Ala Gly Thr His Pro Gly Ala Gly Ile Pro Gly Val Ile Gly Ser Ala
465                 470                 475                 480
Lys Ala Thr Ala Gly Leu Met Leu Glu Asp Leu Ile
                485                 490

<210> SEQ ID NO 9
<211> LENGTH: 891
<212> TYPE: DNA
<213> ORGANISM: Pantoea stewartii
<220> FEATURE:
<221> NAME/KEY: CDS
<222> LOCATION: (1)..(891)

<400> SEQUENCE: 9 atg gcg gtt ggc tcg aaa agc ttt gcg act gca tcg acg ctt ttc gac      48
Met Ala Val Gly Ser Lys Ser Phe Ala Thr Ala Ser Thr Leu Phe Asp
1               5                   10                  15 gcc aaa acc cgt cgc agc gtg ctg atg ctt tac gca tgg tgc cgc cac      96
Ala Lys Thr Arg Arg Ser Val Leu Met Leu Tyr Ala Trp Cys Arg His
            20                  25                  30 tgc gac gac gtc att gac gat caa aca ctg ggc ttt cat gcc gac cag     144
Cys Asp Asp Val Ile Asp Asp Gln Thr Leu Gly Phe His Ala Asp Gln
        35                  40                  45 ccc tct tcg cag atg cct gag cag cgc ctg cag cag ctt gaa atg aaa     192
Pro Ser Ser Gln Met Pro Glu Gln Arg Leu Gln Gln Leu Glu Met Lys
    50                  55                  60 acg cgt cag gcc tac gcc ggt tcg caa atg cac gag ccc gct ttt gcc     240
Thr Arg Gln Ala Tyr Ala Gly Ser Gln Met His Glu Pro Ala Phe Ala
65                  70                  75                  80 gcg ttt cag gag gtc gcg atg gcg cat gat atc gct ccc gcc tac gcg     288
Ala Phe Gln Glu Val Ala Met Ala His Asp Ile Ala Pro Ala Tyr Ala
                85                  90                  95 ttc gac cat ctg gaa ggt ttt gcc atg gat gtg cgc gaa acg cgc tac     336
Phe Asp His Leu Glu Gly Phe Ala Met Asp Val Arg Glu Thr Arg Tyr
            100                 105                 110 ctg aca ctg gac gat acg ctg cgt tat tgc tat cac gtc gcc ggt gtt     384
Leu Thr Leu Asp Asp Thr Leu Arg Tyr Cys Tyr His Val Ala Gly Val
        115                 120                 125 gtg ggc ctg atg atg gcg caa att atg ggc gtt cgc gat aac gcc acg     432
Val Gly Leu Met Met Ala Gln Ile Met Gly Val Arg Asp Asn Ala Thr
```

-continued

|  |  |  |  |  |  |  |  |  |  |  |  |  |  |  |  |  |
|---|---|---|---|---|---|---|---|---|---|---|---|---|---|---|---|---|
| | 130 | | | | 135 | | | | 140 | | | | | | | |
| ctc | gat | cgc | gcc | tgc | gat | ctc | ggg | ctg | gct | ttc | cag | ttg | acc | aac | att | 480 |
| Leu | Asp | Arg | Ala | Cys | Asp | Leu | Gly | Leu | Ala | Phe | Gln | Leu | Thr | Asn | Ile | |
| 145 | | | | 150 | | | | | 155 | | | | | 160 | | |
| gcg | cgt | gat | att | gtc | gac | gat | gct | cag | gtg | ggc | cgc | tgt | tat | ctg | cct | 528 |
| Ala | Arg | Asp | Ile | Val | Asp | Asp | Ala | Gln | Val | Gly | Arg | Cys | Tyr | Leu | Pro | |
| | | | | 165 | | | | | 170 | | | | | 175 | | |
| gaa | agc | tgg | ctg | gaa | gag | gaa | gga | ctg | acg | aaa | gcg | aat | tat | gct | gcg | 576 |
| Glu | Ser | Trp | Leu | Glu | Glu | Glu | Gly | Leu | Thr | Lys | Ala | Asn | Tyr | Ala | Ala | |
| | | | 180 | | | | | 185 | | | | | 190 | | | |
| cca | gaa | aac | cgg | cag | gcc | tta | agc | cgt | atc | gcc | ggg | cga | ctg | gta | cgg | 624 |
| Pro | Glu | Asn | Arg | Gln | Ala | Leu | Ser | Arg | Ile | Ala | Gly | Arg | Leu | Val | Arg | |
| | | 195 | | | | | 200 | | | | | 205 | | | | |
| gaa | gcg | gaa | ccc | tat | tac | gta | tca | tca | atg | gcc | ggt | ctg | gca | caa | tta | 672 |
| Glu | Ala | Glu | Pro | Tyr | Tyr | Val | Ser | Ser | Met | Ala | Gly | Leu | Ala | Gln | Leu | |
| | 210 | | | | | 215 | | | | | 220 | | | | | |
| ccc | tta | cgc | tcg | gcc | tgg | gcc | atc | gcg | aca | gcg | aag | cag | gtg | tac | cgt | 720 |
| Pro | Leu | Arg | Ser | Ala | Trp | Ala | Ile | Ala | Thr | Ala | Lys | Gln | Val | Tyr | Arg | |
| 225 | | | | 230 | | | | | 235 | | | | | 240 | | |
| aaa | att | ggc | gtg | aaa | gtt | gaa | cag | gcc | ggt | aag | cag | gcc | tgg | gat | cat | 768 |
| Lys | Ile | Gly | Val | Lys | Val | Glu | Gln | Ala | Gly | Lys | Gln | Ala | Trp | Asp | His | |
| | | | | 245 | | | | | 250 | | | | | 255 | | |
| cgc | cag | tcc | acg | tcc | acc | gcc | gaa | aaa | tta | acg | ctt | ttg | ctg | acg | gca | 816 |
| Arg | Gln | Ser | Thr | Ser | Thr | Ala | Glu | Lys | Leu | Thr | Leu | Leu | Leu | Thr | Ala | |
| | | | 260 | | | | | 265 | | | | | 270 | | | |
| tcc | ggt | cag | gca | gtt | act | tcc | cgg | atg | aag | acg | tat | cca | ccc | cgt | cct | 864 |
| Ser | Gly | Gln | Ala | Val | Thr | Ser | Arg | Met | Lys | Thr | Tyr | Pro | Pro | Arg | Pro | |
| | | 275 | | | | | 280 | | | | | 285 | | | | |
| gct | cat | ctc | tgg | cag | cgc | ccg | atc | tag | | | | | | | | 891 |
| Ala | His | Leu | Trp | Gln | Arg | Pro | Ile | | | | | | | | | |
| | 290 | | | | | 295 | | | | | | | | | | |

<210> SEQ ID NO 10
<211> LENGTH: 296
<212> TYPE: PRT
<213> ORGANISM: Pantoea stewartii

<400> SEQUENCE: 10

Met Ala Val Gly Ser Lys Ser Phe Ala Thr Ala Ser Thr Leu Phe Asp
1               5                   10                  15

Ala Lys Thr Arg Arg Ser Val Leu Met Leu Tyr Ala Trp Cys Arg His
            20                  25                  30

Cys Asp Val Ile Asp Asp Gln Thr Leu Gly Phe His Ala Asp Gln
        35                  40                  45

Pro Ser Ser Gln Met Pro Glu Gln Arg Leu Gln Gln Leu Glu Met Lys
    50                  55                  60

Thr Arg Gln Ala Tyr Ala Gly Ser Gln Met His Glu Pro Ala Phe Ala
65                  70                  75                  80

Ala Phe Gln Glu Val Ala Met Ala His Asp Ile Ala Pro Ala Tyr Ala
                85                  90                  95

Phe Asp His Leu Glu Gly Phe Ala Met Asp Val Arg Glu Thr Arg Tyr
            100                 105                 110

Leu Thr Leu Asp Asp Thr Leu Arg Tyr Cys Tyr His Val Ala Gly Val
        115                 120                 125

Val Gly Leu Met Met Ala Gln Ile Met Gly Val Arg Asp Asn Ala Thr
    130                 135                 140

Leu Asp Arg Ala Cys Asp Leu Gly Leu Ala Phe Gln Leu Thr Asn Ile
145                 150                 155                 160

```
Ala Arg Asp Ile Val Asp Ala Gln Val Gly Arg Cys Tyr Leu Pro
            165                 170                 175

Glu Ser Trp Leu Glu Glu Gly Leu Thr Lys Ala Asn Tyr Ala Ala
            180                 185                 190

Pro Glu Asn Arg Gln Ala Leu Ser Arg Ile Ala Gly Arg Leu Val Arg
            195                 200                 205

Glu Ala Glu Pro Tyr Tyr Val Ser Ser Met Ala Gly Leu Ala Gln Leu
    210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Lys Gln Ala Trp Asp His
                245                 250                 255

Arg Gln Ser Thr Ser Thr Ala Glu Lys Leu Thr Leu Leu Leu Thr Ala
            260                 265                 270

Ser Gly Gln Ala Val Thr Ser Arg Met Lys Thr Tyr Pro Pro Arg Pro
        275                 280                 285

Ala His Leu Trp Gln Arg Pro Ile
    290                 295

<210> SEQ ID NO 11
<211> LENGTH: 528
<212> TYPE: DNA
<213> ORGANISM: Pantoea stewartii
<220> FEATURE:
<221> NAME/KEY: CDS
<222> LOCATION: (1)..(528)

<400> SEQUENCE: 11 atg ttg tgg att tgg aat gcc ctg atc gtg ttt gtc acc gtg gtc ggc     48
Met Leu Trp Ile Trp Asn Ala Leu Ile Val Phe Val Thr Val Val Gly
1               5                   10                  15 atg gaa gtg gtt gct gca ctg gca cat aaa tac atc atg cac ggc tgg    96
Met Glu Val Val Ala Ala Leu Ala His Lys Tyr Ile Met His Gly Trp
                20                  25                  30 ggt tgg ggc tgg cat ctt tca cat cat gaa ccg cgt aaa ggc gca ttt   144
Gly Trp Gly Trp His Leu Ser His His Glu Pro Arg Lys Gly Ala Phe
            35                  40                  45 gaa gtt aac gat ctc tat gcc gtg gta ttc gcc att gtg tcg att gcc   192
Glu Val Asn Asp Leu Tyr Ala Val Val Phe Ala Ile Val Ser Ile Ala
        50                  55                  60 ctg att tac ttc ggc agt aca gga atc tgg ccg ctc cag tgg att ggt   240
Leu Ile Tyr Phe Gly Ser Thr Gly Ile Trp Pro Leu Gln Trp Ile Gly
65                  70                  75                  80 gca ggc atg acc gct tat ggt tta ctg tat ttt atg gtc cac gac gga   288
Ala Gly Met Thr Ala Tyr Gly Leu Leu Tyr Phe Met Val His Asp Gly
                85                  90                  95 ctg gta cac cag cgc tgg ccg ttc cgc tac ata ccg cgc aaa ggc tac   336
Leu Val His Gln Arg Trp Pro Phe Arg Tyr Ile Pro Arg Lys Gly Tyr
            100                 105                 110 ctg aaa cgg tta tac atg gcc cac cgt atg cat cat gct gta agg gga   384
Leu Lys Arg Leu Tyr Met Ala His Arg Met His His Ala Val Arg Gly
        115                 120                 125 aaa gag ggc tgc gtg tcc ttt ggt ttt ctg tac gcg cca ccg tta tct   432
Lys Glu Gly Cys Val Ser Phe Gly Phe Leu Tyr Ala Pro Pro Leu Ser
    130                 135                 140 aaa ctt cag gcg acg ctg aga gaa agg cat gcg gct aga tcg ggc gct   480
Lys Leu Gln Ala Thr Leu Arg Glu Arg His Ala Ala Arg Ser Gly Ala
145                 150                 155                 160
```

```
gcc aga gat gag cag gac ggg gtg gat acg tct tca tcc ggg aag taa    528
Ala Arg Asp Glu Gln Asp Gly Val Asp Thr Ser Ser Ser Gly Lys
            165                 170                 175

<210> SEQ ID NO 12
<211> LENGTH: 175
<212> TYPE: PRT
<213> ORGANISM: Pantoea stewartii

<400> SEQUENCE: 12

Met Leu Trp Ile Trp Asn Ala Leu Ile Val Phe Val Thr Val Val Gly
1               5                   10                  15

Met Glu Val Val Ala Ala Leu Ala His Lys Tyr Ile Met His Gly Trp
                20                  25                  30

Gly Trp Gly Trp His Leu Ser His His Glu Pro Arg Lys Gly Ala Phe
            35                  40                  45

Glu Val Asn Asp Leu Tyr Ala Val Phe Ala Ile Val Ser Ile Ala
        50                  55                  60

Leu Ile Tyr Phe Gly Ser Thr Gly Ile Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Lys Glu Gly Cys Val Ser Phe Gly Phe Leu Tyr Ala Pro Pro Leu Ser
    130                 135                 140

Lys Leu Gln Ala Thr Leu Arg Glu Arg His Ala Ala Arg Ser Gly Ala
145                 150                 155                 160

Ala Arg Asp Glu Gln Asp Gly Val Asp Thr Ser Ser Ser Gly Lys
                165                 170                 175

<210> SEQ ID NO 13
<211> LENGTH: 25
<212> TYPE: DNA
<213> ORGANISM: Artificial sequence
<220> FEATURE:
<223> OTHER INFORMATION: Primer

<400> SEQUENCE: 13
atgacggtct gcgcaaaaaa acacg                                         25

<210> SEQ ID NO 14
<211> LENGTH: 28
<212> TYPE: DNA
<213> ORGANISM: Artificial sequence
<220> FEATURE:
<223> OTHER INFORMATION: Primer

<400> SEQUENCE: 14
gagaaattat gttgtggatt tggaatgc                                      28

<210> SEQ ID NO 15
<211> LENGTH: 1554
<212> TYPE: DNA
<213> ORGANISM: Brevibacterium linens ATCC 9175

<400> SEQUENCE: 15
atgacacaga gacgccggcc cagagatcgc ttcgccgaga gaatccaggg cccgcaggga    60
```

```
cggccgcgac tgcttcgacc caaacgggtc accatcatcg gcgccggcat cgccggactg      120
gctgcagccg cgattttggc cgaacacggc gccgaggtca cggtcatcga agaagaccgac     180 tacctcggcg gccgagtggg cgcctggccg gtcgacgacg aacggaccat gagccgagga     240
ttccacgcct tcttccggca gtactacaac ctgcgcgacc tgctcagccg cgcagatccc     300
gaaggtgaat gcctgcggcc cgtcgacgac tacccgctca tccatcgccg aggctcgatg     360
gacacgttcg cctcaattcc ccgcaccccg ccgttcaatc tcctcggttt cgtctggcag     420
agccccacct tcccgatcag aggactccgc gacgtcgata tcgctgccgc agtcgaactc     480
atcgacgtcg agttccccgc aacgtacagc tactatgacg gcgaatctgc cgccgacttc     540
ctcgaccggt tgcgctttcc cgacgaagcc cgccatctgg cgctcgaagt cttcgcccgc     600
tccttcttcg ccgacccgac agagttctct gcgggtgagc tcgtggccat gttccacacc     660
tacttcaccg gttcagcgga agggctgctc ttcgacgtcc ccgtcgatga ctacgacaca     720
gctctatggg caccgttggg cggctacctc gagtcactgg gggtcacgat cgagacgggg     780
acgaccgtga cctcgatcga tcccaccgag tccggatgga cgaccacgac cggagaggcg     840
aacctggaaa gtgatgccgt cgtgctcgca gtcgatcctg ccgctgcccg cgatctgctc     900
agcgcaagcc atgactcgct cgtggacagc gcacccgcgg cccaacggtg gatggagacg     960
atcggctcac agaccaacgc tcccgcgttc gcagtgctgc gactgtggct cggcacgccc    1020
gtggccgacc accgaccggc cttcctgggg acaagcgggt acgacctcct tgacaacgtg    1080
tccgtacttg agcgcttcga ggccggagcc agagcgtggt ccgaatccca ccacggttcg    1140
gtcctcgaac tccacgctta tgcccttgaa ggcgattcat acgacaccga gcgtgggagg    1200
gcggacatcg ttgcgcggct tctgtcagat ctgcatcacg tctacccgga accgcagcc     1260 ctgaccatcg ttgaccagga gctgctcatc gaagcggact gcggtcttac tgacacccgc    1320
ccgtgggagg acaggcccga gccgtccacc ccgatccccg ggctggtggt cgccggagac    1380
tatgtgcgct gcaataccccc tgtggccttg atggaacgtg ccgccacgac tggttatctg    1440
gccgccaacc acctgctctc tacctggagg gtcgagggga cggacctgtg gtcgccaccg    1500
acccgaggcc tgcttcggcg tggagtgctc gggctcatca ggagacgtcg atga          1554
```

<210> SEQ ID NO 16
<211> LENGTH: 57
<212> TYPE: DNA
<213> ORGANISM: artificial sequence
<220> FEATURE:
<223> OTHER INFORMATION: Primer

<400> SEQUENCE: 16

```
atgacccagc gtcgccgccc gcgcgatcgc ttcgccgaga gaatccaggg cccgcag       57
```

<210> SEQ ID NO 17
<211> LENGTH: 64
<212> TYPE: DNA
<213> ORGANISM: artificial sequence
<220> FEATURE:
<223> OTHER INFORMATION: Primer

<400> SEQUENCE: 17

```
tcagcgacgg cggcggatca ggcccagcac gccacggcgc agcaggcctc gggtcggtgg    60
cgac                                                                 64
```

<210> SEQ ID NO 18
<211> LENGTH: 1554

```
<212> TYPE: DNA
<213> ORGANISM: Artificial sequence
<220> FEATURE:
<223> OTHER INFORMATION: Modified crtU for E. coli expression.
<220> FEATURE:
<221> NAME/KEY: CDS
<222> LOCATION: (1)..(1554)

<400> SEQUENCE: 18 atg acc cag cgt cgc cgc ccg cgc gat cgc ttc gcc gag aga atc cag      48
Met Thr Gln Arg Arg Arg Pro Arg Asp Arg Phe Ala Glu Arg Ile Gln
 1               5                  10                  15 ggc ccg cag gga cgg ccg cga ctg ctt cga ccc aaa cgg gtc acc atc      96
Gly Pro Gln Gly Arg Pro Arg Leu Leu Arg Pro Lys Arg Val Thr Ile
             20                  25                  30 atc ggc gcc ggc atc gcc gga ctg gct gca gcc gcg att ttg gcc gaa     144
Ile Gly Ala Gly Ile Ala Gly Leu Ala Ala Ala Ala Ile Leu Ala Glu
         35                  40                  45 cac ggc gcc gag gtc acg gtc atc gag aag acc gac tac ctc ggc ggc     192
His Gly Ala Glu Val Thr Val Ile Glu Lys Thr Asp Tyr Leu Gly Gly
     50                  55                  60 cga gtg ggc gcc tgg ccg gtc gac gac gaa cgg acc atg agc cga gga     240
Arg Val Gly Ala Trp Pro Val Asp Asp Glu Arg Thr Met Ser Arg Gly
 65                  70                  75                  80 ttc cac gcc ttc ttc cgg cag tac tac aac ctg cgc gac ctg ctc agc     288
Phe His Ala Phe Phe Arg Gln Tyr Tyr Asn Leu Arg Asp Leu Leu Ser
                 85                  90                  95 cgc gca gat ccc gaa ggt gaa tgc ctg cgg ccc gtc gac gac tac ccg     336
Arg Ala Asp Pro Glu Gly Glu Cys Leu Arg Pro Val Asp Asp Tyr Pro
            100                 105                 110 ctc atc cat cgc cga ggc tcg atg gac acg ttc gcc tca att ccc cgc     384
Leu Ile His Arg Arg Gly Ser Met Asp Thr Phe Ala Ser Ile Pro Arg
        115                 120                 125 acc ccg ccg ttc aat ctc ctc ggt ttc gtc tgg cag agc ccc acc ttc     432
Thr Pro Pro Phe Asn Leu Leu Gly Phe Val Trp Gln Ser Pro Thr Phe
    130                 135                 140 ccg atc aga gga ctc cgc gac gtc gat atc gct gcc gca gtc gaa ctc     480
Pro Ile Arg Gly Leu Arg Asp Val Asp Ile Ala Ala Ala Val Glu Leu
145                 150                 155                 160 atc gac gtc gag ttc ccc gca acg tac agc tac tat gac ggc gaa tct     528
Ile Asp Val Glu Phe Pro Ala Thr Tyr Ser Tyr Tyr Asp Gly Glu Ser
                165                 170                 175 gcc gcc gac ttc ctc gac cgg ttg cgc ttt ccc gac gaa gcc cgc cat     576
Ala Ala Asp Phe Leu Asp Arg Leu Arg Phe Pro Asp Glu Ala Arg His
            180                 185                 190 ctg gcg ctc gaa gtc ttc gcc cgc tcc ttc ttc gcc gac ccg aca gag     624
Leu Ala Leu Glu Val Phe Ala Arg Ser Phe Phe Ala Asp Pro Thr Glu
        195                 200                 205 ttc tct gcg ggt gag ctc gtg gcc atg ttc cac acc tac ttc acc ggt     672
Phe Ser Ala Gly Glu Leu Val Ala Met Phe His Thr Tyr Phe Thr Gly
    210                 215                 220 tca gcg gaa ggg ctg ctc ttc gac gtc ccc gtc gat gac tac gac aca     720
Ser Ala Glu Gly Leu Leu Phe Asp Val Pro Val Asp Asp Tyr Asp Thr
225                 230                 235                 240 gct cta tgg gca ccg ttg ggc ggc tac ctc gag tca ctg ggg gtc acg     768
Ala Leu Trp Ala Pro Leu Gly Gly Tyr Leu Glu Ser Leu Gly Val Thr
                245                 250                 255 atc gag acg ggg acg acc gtg acc tcg atc gat ccc acc gag tcc gga     816
Ile Glu Thr Gly Thr Thr Val Thr Ser Ile Asp Pro Thr Glu Ser Gly
            260                 265                 270 tgg acg acc acg acc gga gag gcg aac ctg gaa agt gat gcc gtc gtg     864
```

-continued

| | | | | | | | | | | | | | | | | |
|---|---|---|---|---|---|---|---|---|---|---|---|---|---|---|---|---|
| Trp | Thr | Thr | Thr | Thr | Gly | Glu | Ala | Asn | Leu | Glu | Ser | Asp | Ala | Val | Val | |
| | | 275 | | | | 280 | | | | | 285 | | | | | |

```
ctc gca gtc gat cct gcc gct gcc cgc gat ctg ctc agc gca agc cat       912
Leu Ala Val Asp Pro Ala Ala Ala Arg Asp Leu Leu Ser Ala Ser His
    290             295                 300 gac tcg ctc gtg gac agc gca ccc gcg gcc caa cgg tgg atg gag acg       960
Asp Ser Leu Val Asp Ser Ala Pro Ala Ala Gln Arg Trp Met Glu Thr
305             310                 315                 320 atc ggc tca cag acc aac gct ccc gcg ttc gca gtg ctg cga ctg tgg      1008
Ile Gly Ser Gln Thr Asn Ala Pro Ala Phe Ala Val Leu Arg Leu Trp
                325                 330                 335 ctc ggc acg ccc gtg gcc gac cac cga ccg gcc ttc ctg ggg aca agc      1056
Leu Gly Thr Pro Val Ala Asp His Arg Pro Ala Phe Leu Gly Thr Ser
            340                 345                 350 ggg tac gac ctc ctt gac aac gtg tcc gta ctt gag cgc ttc gag gcc      1104
Gly Tyr Asp Leu Leu Asp Asn Val Ser Val Leu Glu Arg Phe Glu Ala
        355                 360                 365 gga gcc aga gcg tgg tcc gaa tcc cac cac ggt tcg gtc ctc gaa ctc      1152
Gly Ala Arg Ala Trp Ser Glu Ser His His Gly Ser Val Leu Glu Leu
    370                 375                 380 cac gct tat gcc ctt gaa ggc gat tca tac gac acc gag cgt ggg agg      1200
His Ala Tyr Ala Leu Glu Gly Asp Ser Tyr Asp Thr Glu Arg Gly Arg
385                 390                 395                 400 gcg gac atc gtt gcg cgg ctt ctg tca gat ctg cat cac gtc tac ccc      1248
Ala Asp Ile Val Ala Arg Leu Leu Ser Asp Leu His His Val Tyr Pro
                405                 410                 415 gaa acc gca gcc ctg acc atc gtt gac cag gag ctg ctc atc gaa gcg      1296
Glu Thr Ala Ala Leu Thr Ile Val Asp Gln Glu Leu Leu Ile Glu Ala
            420                 425                 430 gac tgc ggt ctt act gac acc cgc ccg tgg gag gac agg ccc gag ccg      1344
Asp Cys Gly Leu Thr Asp Thr Arg Pro Trp Glu Asp Arg Pro Glu Pro
        435                 440                 445 tcc acc ccg atc ccc ggg ctg gtg gtc gcc gga gac tat gtg cgc tgc      1392
Ser Thr Pro Ile Pro Gly Leu Val Val Ala Gly Asp Tyr Val Arg Cys
    450                 455                 460 aat acc cct gtg gcc ttg atg gaa cgt gcc gcc acg act ggt tat ctg      1440
Asn Thr Pro Val Ala Leu Met Glu Arg Ala Ala Thr Thr Gly Tyr Leu
465                 470                 475                 480 gcc gcc aac cac ctg ctc tct acc tgg agg gtc gag ggg acg gac ctg      1488
Ala Ala Asn His Leu Leu Ser Thr Trp Arg Val Glu Gly Thr Asp Leu
                485                 490                 495 tgg tcg cca ccg acc cga ggc ctg ctc cgc cgt ggc gtg ctg ggc ctg      1536
Trp Ser Pro Pro Thr Arg Gly Leu Leu Arg Arg Gly Val Leu Gly Leu
            500                 505                 510 atc cgc cgc cgt cgc tga                                              1554
Ile Arg Arg Arg Arg
        515
```

<210> SEQ ID NO 19
<211> LENGTH: 517
<212> TYPE: PRT
<213> ORGANISM: Artificial sequence
<220> FEATURE:
<223> OTHER INFORMATION: Modified crtU for E. coli expression.

<400> SEQUENCE: 19

Met Thr Gln Arg Arg Pro Arg Asp Arg Phe Ala Glu Arg Ile Gln
1               5                   10                  15

Gly Pro Gln Gly Arg Pro Arg Leu Leu Arg Pro Lys Arg Val Thr Ile
            20                  25                  30

-continued

```
Ile Gly Ala Gly Ile Ala Gly Leu Ala Ala Ala Ile Leu Ala Glu
        35                  40                  45
His Gly Ala Glu Val Thr Val Ile Glu Lys Thr Asp Tyr Leu Gly
    50                  55                  60
Arg Val Gly Ala Trp Pro Val Asp Asp Glu Arg Thr Met Ser Arg Gly
65                  70                  75                  80
Phe His Ala Phe Phe Arg Gln Tyr Tyr Asn Leu Arg Asp Leu Leu Ser
                85                  90                  95
Arg Ala Asp Pro Glu Gly Glu Cys Leu Arg Pro Val Asp Asp Tyr Pro
            100                 105                 110
Leu Ile His Arg Arg Gly Ser Met Asp Thr Phe Ala Ser Ile Pro Arg
        115                 120                 125
Thr Pro Pro Phe Asn Leu Leu Gly Phe Val Trp Gln Ser Pro Thr Phe
    130                 135                 140
Pro Ile Arg Gly Leu Arg Asp Val Asp Ile Ala Ala Ala Val Glu Leu
145                 150                 155                 160
Ile Asp Val Glu Phe Pro Ala Thr Tyr Ser Tyr Tyr Asp Gly Glu Ser
                165                 170                 175
Ala Ala Asp Phe Leu Asp Arg Leu Arg Phe Pro Asp Glu Ala Arg His
            180                 185                 190
Leu Ala Leu Glu Val Phe Ala Arg Ser Phe Phe Ala Asp Pro Thr Glu
        195                 200                 205
Phe Ser Ala Gly Glu Leu Val Ala Met Phe His Thr Tyr Phe Thr Gly
    210                 215                 220
Ser Ala Glu Gly Leu Leu Phe Asp Val Pro Val Asp Asp Tyr Asp Thr
225                 230                 235                 240
Ala Leu Trp Ala Pro Leu Gly Gly Tyr Leu Glu Ser Leu Gly Val Thr
                245                 250                 255
Ile Glu Thr Gly Thr Thr Val Thr Ser Ile Asp Pro Thr Glu Ser Gly
            260                 265                 270
Trp Thr Thr Thr Thr Gly Glu Ala Asn Leu Glu Ser Asp Ala Val Val
        275                 280                 285
Leu Ala Val Asp Pro Ala Ala Ala Arg Asp Leu Leu Ser Ala Ser His
    290                 295                 300
Asp Ser Leu Val Asp Ser Ala Pro Ala Ala Gln Arg Trp Met Glu Thr
305                 310                 315                 320
Ile Gly Ser Gln Thr Asn Ala Pro Ala Phe Ala Val Leu Arg Leu Trp
                325                 330                 335
Leu Gly Thr Pro Val Ala Asp His Arg Pro Ala Phe Leu Gly Thr Ser
            340                 345                 350
Gly Tyr Asp Leu Leu Asp Asn Val Ser Val Leu Glu Arg Phe Glu Ala
        355                 360                 365
Gly Ala Arg Ala Trp Ser Glu Ser His His Gly Ser Val Leu Glu Leu
    370                 375                 380
His Ala Tyr Ala Leu Glu Gly Asp Ser Tyr Asp Thr Glu Arg Gly Arg
385                 390                 395                 400
Ala Asp Ile Val Ala Arg Leu Leu Ser Asp Leu His His Val Tyr Pro
                405                 410                 415
Glu Thr Ala Ala Leu Thr Ile Val Asp Gln Glu Leu Leu Ile Glu Ala
            420                 425                 430
Asp Cys Gly Leu Thr Asp Thr Arg Pro Trp Glu Asp Arg Pro Glu Pro
        435                 440                 445
Ser Thr Pro Ile Pro Gly Leu Val Val Ala Gly Asp Tyr Val Arg Cys
```

```
                450             455             460
Asn Thr Pro Val Ala Leu Met Glu Arg Ala Ala Thr Thr Gly Tyr Leu
465                 470                 475                 480

Ala Ala Asn His Leu Leu Ser Thr Trp Arg Val Glu Gly Thr Asp Leu
                485                 490                 495

Trp Ser Pro Pro Thr Arg Gly Leu Leu Arg Arg Gly Val Leu Gly Leu
            500                 505                 510

Ile Arg Arg Arg Arg
        515

<210> SEQ ID NO 20
<211> LENGTH: 61
<212> TYPE: DNA
<213> ORGANISM: Artificial sequence
<220> FEATURE:
<223> OTHER INFORMATION: Primer

<400> SEQUENCE: 20
tggaagcgct agcggactac atcatccagc gtaataaata acgtcttgag cgattgtgta    60
g                                                                    61

<210> SEQ ID NO 21
<211> LENGTH: 65
<212> TYPE: DNA
<213> ORGANISM: Artificial sequence
<220> FEATURE:
<223> OTHER INFORMATION: Primer

<400> SEQUENCE: 21
tctgatgcgc aagctgaaga aaaatgagca tggagaataa tatgacgtct tgagcgattg    60
tgtag                                                                65

<210> SEQ ID NO 22
<211> LENGTH: 65
<212> TYPE: DNA
<213> ORGANISM: Artificial sequence
<220> FEATURE:
<223> OTHER INFORMATION: Primer

<400> SEQUENCE: 22
gacgcgtcga agcgcgcaca gtctgcgggg caaaacaatc gataacgtct tgagcgattg    60
tgtag                                                                65

<210> SEQ ID NO 23
<211> LENGTH: 64
<212> TYPE: DNA
<213> ORGANISM: Artificial sequence
<220> FEATURE:
<223> OTHER INFORMATION: Primer

<400> SEQUENCE: 23
gaagacgaaa gggcctcgtg atacgcctat ttttataggt tatatgaata tcctccttag    60
ttcc                                                                 64

<210> SEQ ID NO 24
<211> LENGTH: 50
<212> TYPE: DNA
<213> ORGANISM: Artificial sequence
<220> FEATURE:
<223> OTHER INFORMATION: Primer

<400> SEQUENCE: 24
```
ctaaggagga tattcatata acctataaaa ataggcgtat cacgaggccc    50

<210> SEQ ID NO 25
<211> LENGTH: 70
<212> TYPE: DNA
<213> ORGANISM: Artificial sequence
<220> FEATURE:
<223> OTHER INFORMATION: Primer

<400> SEQUENCE: 25
ggagtcgacc agtgccaggg tcgggtattt ggcaatatca aaactcatag ttaatttctc    60
ctctttaatg    70

<210> SEQ ID NO 26
<211> LENGTH: 68
<212> TYPE: DNA
<213> ORGANISM: Artificial sequence
<220> FEATURE:
<223> OTHER INFORMATION: Primer

<400> SEQUENCE: 26
tgggaactcc ctgtgcattc aataaaatga cgtgttccgt ttgcatagtt aatttctcct    60
ctttaatg    68

<210> SEQ ID NO 27
<211> LENGTH: 68
<212> TYPE: DNA
<213> ORGANISM: Artificial sequence
<220> FEATURE:
<223> OTHER INFORMATION: Primer

<400> SEQUENCE: 27
cggccgccgg aaccacggcg caaacatcca aatgagtggt tgccatagtt aatttctcct    60
ctttaatg    68

<210> SEQ ID NO 28
<211> LENGTH: 25
<212> TYPE: DNA
<213> ORGANISM: Artificial sequence
<220> FEATURE:
<223> OTHER INFORMATION: Primer

<400> SEQUENCE: 28
accggatatc accacttatc tgctc    25

<210> SEQ ID NO 29
<211> LENGTH: 26
<212> TYPE: DNA
<213> ORGANISM: Artificial sequence
<220> FEATURE:
<223> OTHER INFORMATION: Primer

<400> SEQUENCE: 29
tggcaacagt cgtagctcct gggtgg    26

<210> SEQ ID NO 30
<211> LENGTH: 32
<212> TYPE: DNA
<213> ORGANISM: Artificial sequence
<220> FEATURE:
<223> OTHER INFORMATION: Primer

<400> SEQUENCE: 30
taacctataa aaataggcgt atcacgaggc cc    32

<210> SEQ ID NO 31
<211> LENGTH: 25
<212> TYPE: DNA
<213> ORGANISM: Artificial sequence
<220> FEATURE:
<223> OTHER INFORMATION: Primer

<400> SEQUENCE: 31
cagccaactg gagaacgcga gatgt    25

<210> SEQ ID NO 32
<211> LENGTH: 25
<212> TYPE: DNA
<213> ORGANISM: Artificial sequence
<220> FEATURE:
<223> OTHER INFORMATION: Primer

<400> SEQUENCE: 32
ccagcagcgc atgcaccgag tgttc    25

<210> SEQ ID NO 33
<211> LENGTH: 65
<212> TYPE: DNA
<213> ORGANISM: Artificial sequence
<220> FEATURE:
<223> OTHER INFORMATION: Primer

<400> SEQUENCE: 33
agccgtcgca ggaggaacaa ctcatatcat cattgcgatc tcgaccgtct tgagcgattg    60
tgtag    65

<210> SEQ ID NO 34
<211> LENGTH: 51
<212> TYPE: DNA
<213> ORGANISM: Artificial sequence
<220> FEATURE:
<223> OTHER INFORMATION: Primer

<400> SEQUENCE: 34
tgaacgtgtt tttttgcgca gaccgtcata gttaatttct cctctttaat g    51

<210> SEQ ID NO 35
<211> LENGTH: 55
<212> TYPE: DNA
<213> ORGANISM: Artificial sequence
<220> FEATURE:
<223> OTHER INFORMATION: Primer

<400> SEQUENCE: 35
acagaattca ttaaagagga gaaattaact atgacggtct gcgcaaaaaa acacg    55

<210> SEQ ID NO 36
<211> LENGTH: 65
<212> TYPE: DNA
<213> ORGANISM: Artificial sequence
<220> FEATURE:
<223> OTHER INFORMATION: Primer

<400> SEQUENCE: 36
agaatgacca gctggatgca ttatctttat ttggatcatt gagggttaac tgacggcagc    60
gagtt    65

```
<210> SEQ ID NO 37
<211> LENGTH: 26
<212> TYPE: DNA
<213> ORGANISM: Artificial sequence
<220> FEATURE:
<223> OTHER INFORMATION: Primer

<400> SEQUENCE: 37
ccatgaccct acattgtgat ctatag                                    26

<210> SEQ ID NO 38
<211> LENGTH: 25
<212> TYPE: DNA
<213> ORGANISM: Artificial sequence
<220> FEATURE:
<223> OTHER INFORMATION: Primer

<400> SEQUENCE: 38
ggaaccattg aactggaccc taacg                                     25

<210> SEQ ID NO 39
<211> LENGTH: 56
<212> TYPE: DNA
<213> ORGANISM: Artificial sequence
<220> FEATURE:
<223> OTHER INFORMATION: Primer

<400> SEQUENCE: 39
tcctccagca ttaagcctgc cgtcgccttt taactgacgg cagcgagttt tttgtc    56

<210> SEQ ID NO 40
<211> LENGTH: 54
<212> TYPE: DNA
<213> ORGANISM: Artificial sequence
<220> FEATURE:
<223> OTHER INFORMATION: Primer

<400> SEQUENCE: 40
tttgacaaaa aactcgctgc cgtcagttaa aaggcgacgg caggcttaat gctg      54

<210> SEQ ID NO 41
<211> LENGTH: 65
<212> TYPE: DNA
<213> ORGANISM: Artificial sequence
<220> FEATURE:
<223> OTHER INFORMATION: Primer

<400> SEQUENCE: 41
agaatgacca gctggatgca ttatctttat ttggatcatt gagggctaga tcgggcgctg 60
ccaga                                                           65

<210> SEQ ID NO 42
<211> LENGTH: 20
<212> TYPE: DNA
<213> ORGANISM: Artificial sequence
<220> FEATURE:
<223> OTHER INFORMATION: Primer

<400> SEQUENCE: 42
cagtcatagc cgaatagcct                                           20

<210> SEQ ID NO 43
<211> LENGTH: 20
<212> TYPE: DNA
<213> ORGANISM: Artificial sequence
<220> FEATURE:
```

<223> OTHER INFORMATION: Primer

<400> SEQUENCE: 43
cggtgccctg aatgaactgc                                                                 20

<210> SEQ ID NO 44
<211> LENGTH: 25
<212> TYPE: DNA
<213> ORGANISM: Artificial sequence
<220> FEATURE:
<223> OTHER INFORMATION: Primer

<400> SEQUENCE: 44
ctagatcggg cgctgccaga gatga                                                           25

<210> SEQ ID NO 45
<211> LENGTH: 25
<212> TYPE: DNA
<213> ORGANISM: Artificial sequence
<220> FEATURE:
<223> OTHER INFORMATION: Primer

<400> SEQUENCE: 45
acacgttcac cttactggca tttcg                                                           25

<210> SEQ ID NO 46
<211> LENGTH: 19
<212> TYPE: DNA
<213> ORGANISM: Artificial sequence
<220> FEATURE:
<223> OTHER INFORMATION: Primer

<400> SEQUENCE: 46
gagtttgatc ctggctcag                                                                  19

<210> SEQ ID NO 47
<211> LENGTH: 16
<212> TYPE: DNA
<213> ORGANISM: Artificial sequence
<220> FEATURE:
<223> OTHER INFORMATION: Primer

<400> SEQUENCE: 47
taccttgtta cgactt                                                                     16

<210> SEQ ID NO 48
<211> LENGTH: 17
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (11)..(11)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 48
gtgccagcag ymgcggt                                                                    17

<210> SEQ ID NO 49
<211> LENGTH: 1131
<212> TYPE: DNA
<213> ORGANISM: Rhodococcus erythropolis AN12

<220> FEATURE:
<221> NAME/KEY: CDS
<222> LOCATION: (1)..(1131)

<400> SEQUENCE: 49

| | | | | | | | | | | | | | | | | |
|---|---|---|---|---|---|---|---|---|---|---|---|---|---|---|---|---|
| atg | agc | aca | ctc | gac | tcc | tcc | gcc | gac | gtg | gtg | atc | gtg | ggc | gga | ggg | 48 |
| Met | Ser | Thr | Leu | Asp | Ser | Ser | Ala | Asp | Val | Val | Ile | Val | Gly | Gly | Gly | |
| 1 | | | | 5 | | | | | 10 | | | | | 15 | | |
| ccg | gcg | ggg | cgg | gca | ctc | gcg | acg | cgc | tgt | atc | gcc | cgg | caa | ctc | act | 96 |
| Pro | Ala | Gly | Arg | Ala | Leu | Ala | Thr | Arg | Cys | Ile | Ala | Arg | Gln | Leu | Thr | |
| | | 20 | | | | | 25 | | | | | 30 | | | | |
| gtt | gtc | gtt | gtc | gat | ccg | cat | cct | cat | cgg | gtg | tgg | acg | ccg | acg | tac | 144 |
| Val | Val | Val | Val | Asp | Pro | His | Pro | His | Arg | Val | Trp | Thr | Pro | Thr | Tyr | |
| | | | 35 | | | | | 40 | | | | | 45 | | | |
| tcg | gtg | tgg | gca | gac | gag | ctg | ccg | tcg | tgg | ctg | ccg | gac | gag | gtg | atc | 192 |
| Ser | Val | Trp | Ala | Asp | Glu | Leu | Pro | Ser | Trp | Leu | Pro | Asp | Glu | Val | Ile | |
| | 50 | | | | | 55 | | | | | 60 | | | | | |
| gcg | agc | cga | atc | gaa | cgc | ccg | agc | gtg | tgg | acc | agc | ggg | cag | aaa | acg | 240 |
| Ala | Ser | Arg | Ile | Glu | Arg | Pro | Ser | Val | Trp | Thr | Ser | Gly | Gln | Lys | Thr | |
| 65 | | | | 70 | | | | | 75 | | | | | 80 | | |
| ctt | gat | cgc | atc | tat | tgc | gta | ttg | aat | aca | tct | tta | ctg | caa | tca | ttt | 288 |
| Leu | Asp | Arg | Ile | Tyr | Cys | Val | Leu | Asn | Thr | Ser | Leu | Leu | Gln | Ser | Phe | |
| | | | | 85 | | | | | 90 | | | | | 95 | | |
| ctc | tcc | cac | aca | tcc | ata | aag | gtc | aga | ggc | tta | cgc | gct | caa | aca | ctg | 336 |
| Leu | Ser | His | Thr | Ser | Ile | Lys | Val | Arg | Gly | Leu | Arg | Ala | Gln | Thr | Leu | |
| | | | 100 | | | | | 105 | | | | | 110 | | | |
| tcc | acc | acc | acc | gtc | gtg | tgc | gtg | gac | gga | tcg | cag | ctg | acg | gga | tcc | 384 |
| Ser | Thr | Thr | Thr | Val | Val | Cys | Val | Asp | Gly | Ser | Gln | Leu | Thr | Gly | Ser | |
| | | | 115 | | | | | 120 | | | | | 125 | | | |
| gtc | gtc | gtc | gac | gcc | cga | ggc | acc | gat | ctg | gca | gtg | aca | acc | gcg | cag | 432 |
| Val | Val | Val | Asp | Ala | Arg | Gly | Thr | Asp | Leu | Ala | Val | Thr | Thr | Ala | Gln | |
| | | 130 | | | | | 135 | | | | | 140 | | | | |
| cag | acg | gcc | ttc | gga | atg | atc | gtg | gac | cga | gct | ctg | gcc | gat | ccg | att | 480 |
| Gln | Thr | Ala | Phe | Gly | Met | Ile | Val | Asp | Arg | Ala | Leu | Ala | Asp | Pro | Ile | |
| 145 | | | | 150 | | | | | 155 | | | | | 160 | | |
| ctg | ggc | ggc | agc | gag | gcc | tgg | ttc | atg | gac | tgg | cga | aca | gac | aac | ggc | 528 |
| Leu | Gly | Gly | Ser | Glu | Ala | Trp | Phe | Met | Asp | Trp | Arg | Thr | Asp | Asn | Gly | |
| | | | | 165 | | | | | 170 | | | | | 175 | | |
| acc | tcc | gac | gcc | gac | act | ccg | tcg | ttt | ctc | tac | gcg | gtc | ccg | ctc | gac | 576 |
| Thr | Ser | Asp | Ala | Asp | Thr | Pro | Ser | Phe | Leu | Tyr | Ala | Val | Pro | Leu | Asp | |
| | | | 180 | | | | | 185 | | | | | 190 | | | |
| gac | gag | cga | gtc | ctc | ctc | gag | gag | acc | tgc | ctc | gtc | ggc | cgg | ccg | gcg | 624 |
| Asp | Glu | Arg | Val | Leu | Leu | Glu | Glu | Thr | Cys | Leu | Val | Gly | Arg | Pro | Ala | |
| | | 195 | | | | | 200 | | | | | 205 | | | | |
| ttg | ggg | ttg | cgt | gaa | ctc | gaa | aca | cgt | ctg | cgc | acc | cga | ctt | cac | aat | 672 |
| Leu | Gly | Leu | Arg | Glu | Leu | Glu | Thr | Arg | Leu | Arg | Thr | Arg | Leu | His | Asn | |
| | 210 | | | | | 215 | | | | | 220 | | | | | |
| cgg | ggc | tgc | gaa | gtc | ccc | gac | gac | gcg | ccg | gtc | gag | cga | gtc | cgt | ttt | 720 |
| Arg | Gly | Cys | Glu | Val | Pro | Asp | Asp | Ala | Pro | Val | Glu | Arg | Val | Arg | Phe | |
| 225 | | | | 230 | | | | | 235 | | | | | 240 | | |
| gcg | gtc | gaa | ggc | ccg | agg | gac | tcg | tcc | ccg | gac | ggt | gtc | ctc | cgg | ttc | 768 |
| Ala | Val | Glu | Gly | Pro | Arg | Asp | Ser | Ser | Pro | Asp | Gly | Val | Leu | Arg | Phe | |
| | | | | 245 | | | | | 250 | | | | | 255 | | |
| ggc | ggg | cga | ggc | ggt | ctg | atg | cat | ccg | gga | acc | gga | tac | agc | gtt | gcc | 816 |
| Gly | Gly | Arg | Gly | Gly | Leu | Met | His | Pro | Gly | Thr | Gly | Tyr | Ser | Val | Ala | |
| | | | | 260 | | | | | 265 | | | | | 270 | | |
| tcc | tca | ctc | gcc | gag | gcc | gac | act | gtc | gcg | aaa | gca | atc | gcc | gac | ggt | 864 |
| Ser | Ser | Leu | Ala | Glu | Ala | Asp | Thr | Val | Ala | Lys | Ala | Ile | Ala | Asp | Gly | |
| | | 275 | | | | | 280 | | | | | 285 | | | | |
| gag | gat | ccg | aac | gcg | gca | ctc | tgg | cct | cgc | tcg | gcc | aag | gcg | gta | tcc | 912 |

```
Glu Asp Pro Asn Ala Ala Leu Trp Pro Arg Ser Ala Lys Ala Val Ser
    290                 295                 300 gct ctc cgc cgc gtt ggt ctg aac gca ctt ctc acc ctc gac tcg ggc        960
Ala Leu Arg Arg Val Gly Leu Asn Ala Leu Leu Thr Leu Asp Ser Gly
305                 310                 315                 320 gaa gtc acc aca ttc ttc gac aag ttc ttc gat cta ccg gtc gag gct       1008
Glu Val Thr Thr Phe Phe Asp Lys Phe Phe Asp Leu Pro Val Glu Ala
                325                 330                 335 cag cgg tca tac ctt tcc gat cgg cgg gac gcg gcc gcg acg gcg aag       1056
Gln Arg Ser Tyr Leu Ser Asp Arg Arg Asp Ala Ala Ala Thr Ala Lys
                340                 345                 350 gtg atg gca aca ctg ttc cga tcg tca ccg tgg cac gtc aga aag acg       1104
Val Met Ala Thr Leu Phe Arg Ser Ser Pro Trp His Val Arg Lys Thr
            355                 360                 365 ttg atg cgc gcg ccg ttt ttc cgg tga                                    1131
Leu Met Arg Ala Pro Phe Phe Arg
    370                 375
```

<210> SEQ ID NO 50
<211> LENGTH: 376
<212> TYPE: PRT
<213> ORGANISM: Rhodococcus erythropolis AN12

<400> SEQUENCE: 50

```
Met Ser Thr Leu Asp Ser Ser Ala Asp Val Val Ile Val Gly Gly Gly
1               5                   10                  15

Pro Ala Gly Arg Ala Leu Ala Thr Arg Cys Ile Ala Arg Gln Leu Thr
                20                  25                  30

Val Val Val Asp Pro His Pro His Arg Val Trp Thr Pro Thr Tyr
            35                  40                  45

Ser Val Trp Ala Asp Glu Leu Pro Ser Trp Leu Pro Asp Glu Val Ile
    50                  55                  60

Ala Ser Arg Ile Glu Arg Pro Ser Val Trp Thr Ser Gly Gln Lys Thr
65                  70                  75                  80

Leu Asp Arg Ile Tyr Cys Val Leu Asn Thr Ser Leu Leu Gln Ser Phe
                85                  90                  95

Leu Ser His Thr Ser Ile Lys Val Arg Gly Leu Arg Ala Gln Thr Leu
                100                 105                 110

Ser Thr Thr Thr Val Val Cys Val Asp Gly Ser Gln Leu Thr Gly Ser
            115                 120                 125

Val Val Asp Ala Arg Gly Thr Asp Leu Ala Val Thr Thr Ala Gln
    130                 135                 140

Gln Thr Ala Phe Gly Met Ile Val Asp Arg Ala Leu Ala Asp Pro Ile
145                 150                 155                 160

Leu Gly Gly Ser Glu Ala Trp Phe Met Asp Trp Arg Thr Asp Asn Gly
                165                 170                 175

Thr Ser Asp Ala Asp Thr Pro Ser Phe Leu Tyr Ala Val Pro Leu Asp
            180                 185                 190

Asp Glu Arg Val Leu Leu Glu Glu Thr Cys Leu Val Gly Arg Pro Ala
        195                 200                 205

Leu Gly Leu Arg Glu Leu Glu Thr Arg Leu Arg Thr Arg Leu His Asn
    210                 215                 220

Arg Gly Cys Glu Val Pro Asp Asp Ala Pro Val Glu Arg Val Arg Phe
225                 230                 235                 240

Ala Val Glu Gly Pro Arg Asp Ser Ser Pro Asp Gly Val Leu Arg Phe
                245                 250                 255
```

```
Gly Gly Arg Gly Gly Leu Met His Pro Gly Thr Gly Tyr Ser Val Ala
             260                 265                 270

Ser Ser Leu Ala Glu Ala Asp Thr Val Ala Lys Ala Ile Ala Asp Gly
         275                 280                 285

Glu Asp Pro Asn Ala Ala Leu Trp Pro Arg Ser Ala Lys Ala Val Ser
    290                 295                 300

Ala Leu Arg Arg Val Gly Leu Asn Ala Leu Leu Thr Leu Asp Ser Gly
305                 310                 315                 320

Glu Val Thr Thr Phe Phe Asp Lys Phe Phe Asp Leu Pro Val Glu Ala
                325                 330                 335

Gln Arg Ser Tyr Leu Ser Asp Arg Arg Asp Ala Ala Thr Ala Lys
             340                 345                 350

Val Met Ala Thr Leu Phe Arg Ser Ser Pro Trp His Val Arg Lys Thr
        355                 360                 365

Leu Met Arg Ala Pro Phe Phe Arg
    370                 375
```

<210> SEQ ID NO 51
<211> LENGTH: 41
<212> TYPE: DNA
<213> ORGANISM: Artificial sequence
<220> FEATURE:
<223> OTHER INFORMATION: Primer

<400> SEQUENCE: 51
gaattcagga ggaataaacc atgagcacac tcgactcctc c            41

<210> SEQ ID NO 52
<211> LENGTH: 24
<212> TYPE: DNA
<213> ORGANISM: Artificial sequence
<220> FEATURE:
<223> OTHER INFORMATION: Primer

<400> SEQUENCE: 52
caattgtcac cggaaaaacg gcgc                               24

<210> SEQ ID NO 53
<211> LENGTH: 1554
<212> TYPE: DNA
<213> ORGANISM: Artificial sequence
<220> FEATURE:
<223> OTHER INFORMATION: Modified crtU for expression in E. coli having
      a silent mutation.
<220> FEATURE:
<221> NAME/KEY: misc_feature
<222> LOCATION: (825)..(825)
<223> OTHER INFORMATION: Silent mutation. Expected cytosine residue was
      substituted with thymine residue.

<400> SEQUENCE: 53
atgacccagc gtcgccgccc gcgcgatcgc ttcgccgaga gaatccaggg cccgcaggga    60
cggccgcgac tgcttcgacc caaacgggtc accatcatcg gcgccggcat cgccggactg   120
gctgcagccg cgattttggc cgaacacggc gccgaggtca cggtcatcga agaccgac    180 tacctcggcg gccgagtggg cgcctggccg gtcgacgacg aacggaccat gagccgagga   240
ttccacgcct tcttccggca gtactacaac ctgcgcgacc tgctcagccg cgcagatccc   300
gaaggtgaat gcctgcggcc cgtcgacgac tacccgctca tccatcgccg aggctcgatg   360
gacacgttcg cctcaattcc ccgcaccccg ccgttcaatc tcctcggttt cgtctggcag   420
agccccacct tcccgatcag aggactccgc gacgtcgata tcgctgccgc agtcgaactc   480

-continued

| | |
|---|---|
| atcgacgtcg agttccccgc aacgtacagc tactatgacg gcgaatctgc cgccgacttc | 540 |
| ctcgaccggt tgcgctttcc cgacgaagcc cgccatctgg cgctcgaagt cttcgcccgc | 600 |
| tccttcttcg ccgacccgac agagttctct gcgggtgagc tcgtggccat gttccacacc | 660 |
| tacttcaccg gttcagcgga agggctgctc ttcgacgtcc ccgtcgatga ctacgacaca | 720 |
| gctctatggg caccgttggg cggctaccts gagtcactgg gggtcacgat cgagacgggg | 780 |
| acgaccgtga cctcgatcga tcccaccgag tccggatgga cgactacgac cggagaggcg | 840 |
| aacctggaaa gtgatgccgt cgtgctcgca gtcgatcctg ccgctgcccg cgatctgctc | 900 |
| agcgcaagcc atgactcgct cgtggacagc gcacccgcgg cccaacggtg gatggagacg | 960 |
| atcggctcac agaccaacgc tcccgcgttc gcagtgctgc gactgtggct cggcacgccc | 1020 |
| gtggccgacc accgaccggc cttcctgggg acaagcgggt acgacctcct tgacaacgtg | 1080 |
| tccgtacttg agcgcttcga ggccggagcc agagcgtggt ccgaatccca ccacggttcg | 1140 |
| gtcctcgaac tccacgctta tgcccttgaa ggcgattcat acgacaccga gcgtgggagg | 1200 |
| gcggacatcg ttgcgcggct tctgtcagat ctgcatcacg tctaccccga aaccgcagcc | 1260 |
| ctgaccatcg ttgaccagga gctgctcatc gaagcggact gcggtcttac tgacacccgc | 1320 |
| ccgtgggagg acaggcccga gccgtccacc ccgatccccg ggctggtggt cgccggagac | 1380 |
| tatgtgcgct gcaatacccc tgtggccttg atggaacgtg ccgccacgac tggttatctg | 1440 |
| gccgccaacc acctgctctc tacctggagg gtcgagggga cggacctgtg gtcgccaccg | 1500 |
| acccgaggcc tgctgcgccg tggcgtgctg ggcctgatcc gccgccgtcg ctga | 1554 |

<210> SEQ ID NO 54
<211> LENGTH: 8609
<212> TYPE: DNA
<213> ORGANISM: Artificial sequence
<220> FEATURE:
<223> OTHER INFORMATION: Plasmid pPCB15

<400> SEQUENCE: 54

| | |
|---|---|
| cgtatggcaa tgaaagacgg tgagctggtg atatgggata gtgttcaccc ttgttacacc | 60 |
| gttttccatg agcaaactga aacgttttca tcgctctgga gtgaatacca cgacgatttc | 120 |
| cggcagtttc tacacatata ttcgcaagat gtggcgtgtt acggtgaaaa cctggcctat | 180 |
| ttccctaaag ggtttattga gaatatgttt ttcgtctcag ccaatccctg ggtgagtttc | 240 |
| accagttttg atttaaacgt ggccaatatg gacaacttct tcgcccccgt tttcaccatg | 300 |
| ggcaaatatt atacgcaagg cgacaaggtg ctgatgccgc tggcgattca ggttcatcat | 360 |
| gccgtctgtg atggcttcca tgtcggcaga atgcttaatg aattacaaca gtactgcgat | 420 |
| gagtggcagg gcggggcgta atttttttaa ggcagttatt ggtgcctaga aatatttat | 480 |
| ctgattaata agatgatctt cttgagatcg ttttggtctg cgcgtaatct cttgctctga | 540 |
| aaacgaaaaa accgccttgc agggcggttt ttcgaaggtt ctctgagcta ccaactcttt | 600 |
| gaaccgaggt aactggcttg gaggagcgca gtcaccaaaa cttgtccttt cagtttagcc | 660 |
| ttaaccggcg catgacttca agactaactc ctctaaatca attaccagtg gctgctgcca | 720 |
| gtggtgcttt tgcatgtctt tccgggttgg actcaagacg atagttaccg gataaggcgc | 780 |
| agcggtcgga ctgaacgggg ggttcgtgca tacagtccag cttggagcga actgcctacc | 840 |
| cggaactgag tgtcaggcgt ggaatgagac aaacgcggcc ataacagcgg aatgacaccg | 900 |
| gtaaaccgaa aggcaggaac aggagagcgc acgagggagc cgccagggga aacgcctggt | 960 |

-continued

```
atctttatag tcctgtcggg tttcgccacc actgatttga gcgtcagatt tcgtgatgct    1020
tgtcaggggg gcggagccta tggaaaaacg gctttgccgc ggccctctca cttccctgtt    1080
aagtatcttc ctggcatctt ccaggaaatc tccgccccgt tcgtaagcca tttccgctcg    1140
ccgcagtcga acgaccgagc gtagcgagtc agtgagcgag gaagcggaat atatcctgta    1200
tcacatattc tgctgacgca ccggtgcagc ctttttctc ctgccacatg aagcacttca    1260
ctgacaccct catcagtgcc aacatagtaa gccagtatat acactccgct agcgcccaat    1320
acgcaaaccg cctctccccg cgcgttggcc gattcattaa tgcagctggc acgacaggtt    1380
tcccgactgg aaagcgggca gtgagcgcaa cgcaattaat gtgagttagc tcactcatta    1440
ggcaccccag gctttacact ttatgcttcc ggctcgtatg ttgtgtggaa ttgtgagcgg    1500
ataacaattt cacacaggaa acagctatga ccatgattac gaattcgagc tcggtaccca    1560
aacgaattcg ccctttttgac ggtctgcgca aaaaaacacg ttcaccttac tggcatttcg    1620
gctgagcagt tgctggctga tatcgatagc cgccttgatc agttactgcc ggttcagggt    1680
gagcgggatt gtgtgggtgc cgcgatgcgt gaaggcacgc tggcaccggg caaacgtatt    1740
cgtccgatgc tgctgttatt aacagcgcgc gatcttggct gtgcgatcag tcacggggga    1800
ttactggatt tagcctgcgc ggttgaaatg gtgcatgctg cctcgctgat tctggatgat    1860
atgccctgca tggacgatgc gcagatgcgt cggggggcgtc ccaccattca cacgcagtac    1920
ggtgaacatg tggcgattct ggcggcggtc gctttactca gcaaagcgtt tggggtgatt    1980
gccgaggctg aaggtctgac gccgatagcc aaaactcgcg cggtgtcgga gctgtccact    2040
gcgattggca tgcagggtct ggttcagggc cagtttaagg acctctcgga aggcgataaa    2100
ccccgcagcg ccgatgccat actgctaacc aatcagttta aaaccagcac gctgttttgc    2160
gcgtcaacgc aaatggcgtc cattgcggcc aacgcgtcct gcgaagcgcg tgagaacctg    2220
catcgtttct cgctcgatct cggccaggcc tttcagttgc ttgacgatct taccgatggc    2280
atgaccgata ccggcaaaga catcaatcag gatgcaggta aatcaacgct ggtcaattta    2340
ttaggctcag gcgcggtcga agaacgcctg cgacagcatt tgcgcctggc cagtgaacac    2400
cttttccgcgg catgccaaaa cggccattcc accacccaac tttttattca ggcctggttt    2460
gacaaaaaac tcgctgccgt cagttaagga tgctgcatga gccattttgc ggtgatcgca    2520
ccgccctttt tcagccatgt tcgcgctctg caaaaccttg ctcaggaatt agtggcccgc    2580
ggtcatcgtg ttacgttttt tcagcaacat gactgcaaag cgctggtaac gggcagcgat    2640
atcggattcc agaccgtcgg actgcaaacg catcctcccg gttccttatc gcacctgctg    2700
cacctggccg cgcacccact cggaccctcg atgttacgac tgatcaatga aatggcacgt    2760
accagcgata tgctttgccg ggaactgccc gccgcttttc atgcgttgca gatagagggc    2820
gtgatcgttg atcaaatgga gccggcaggt gcagtagtcg cagaagcgtc aggtctgccg    2880
tttgtttcgg tggcctgcgc gctgccgctc aaccgcgaac cgggtttgcc tctggcggtg    2940
atgcctttcg agtacggcac cagcgatgcg gctcgggaac gctataccac cagcgaaaaa    3000
atttatgact ggctgatgcg acgtcacgat cgtgtgatcg cgcatcatgc atgcagaatg    3060
ggtttagccc cgcgtgaaaa actgcatcat tgttttctc cactggcaca aatcagccag    3120
ttgatccccg aactggattt tccccgcaaa gcgctgccag actgctttca tgcggttgga    3180
ccgttacggc aaccccaggg gacgccgggg tcatcaactt cttatttcc gtccccggac    3240
aaacccgta ttttttgcctc gctgggcacc ctgcagggac atcgttatgg cctgttcagg    3300
accatcgcca aagcctgcga agaggtggat gcgcagttac tgttggcaca ctgtggcggc    3360
```

```
ctctcagcca cgcaggcagg tgaactggcc cggggcgggg acattcaggt tgtggatttt    3420
gccgatcaat ccgcagcact ttcacaggca cagttgacaa tcacacatgg tgggatgaat    3480
acggtactgg acgctattgc ttcccgcaca ccgctactgg cgctgccgct ggcatttgat    3540
caacctggcg tggcatcacg aattgtttat catggcatcg gcaagcgtgc gtctcggttt    3600
actaccagcc atgcgctggc gcggcagatt cgatcgctgc tgactaacac cgattacccg    3660
cagcgtatga caaaaattca ggccgcattg cgtctggcag gcggcacacc agccgccgcc    3720
gatattgttg aacaggcgat gcggacctgt cagccagtac tcagtgggca ggattatgca    3780
accgcactat gatctcattc tggtcggtgc cggtctggct aatggcctta tcgcgctccg    3840
gcttcagcaa cagcatccgg atatgcggat cttgcttatt gaggcgggtc ctgaggcggg    3900
agggaaccat acctggtcct ttcacgaaga ggatttaacg ctgaatcagc atcgctggat    3960
agcgccgctt gtggtccatc actgcccga ctaccaggtt cgtttccccc aacgccgtcg    4020
ccatgtgaac agtggctact actgcgtgac ctcccggcat ttcgccggga tactccggca    4080
acagtttgga caacatttat ggctgcatac cgcggtttca gccgttcatg ctgaatcggt    4140
ccagttagcg gatggccgga ttattcatgc cagtacagtg atcgacggac ggggttacac    4200
gcctgattct gcactacgcg taggattcca ggcatttatc ggtcaggagt ggcaactgag    4260
cgcgccgcat ggtttatcgt caccgattat catggatgcg acggtcgatc agcaaaatgg    4320
ctaccgcttt gtttataccc tgccgctttc cgcaaccgca ctgctgatcg aagacacaca    4380
ctacattgac aaggctaatc ttcaggccga acgggcgcgt cagaacattc gcgattatgc    4440
tgcgcgacag ggttggccgt tacagacgtt gctgcgggaa gaacagggtg cattgcccat    4500
tacgttaacg ggcgataatc gtcagttttg gcaacagcaa ccgcaagcct gtagcggatt    4560
acgcgccggg ctgtttcatc cgacaaccgg ctactcccta ccgctcgcgg tggcgctggc    4620
cgatcgtctc agcgcgctgg atgtgtttac ctcttcctct gttcaccaga cgattgctca    4680
ctttgcccag caacgttggc agcaacaggg gttttccgc atgctgaatc gcatgttgtt    4740
tttagccgga ccgccgagt cacgctggcg tgtgatgcag cgtttctatg cttacccga    4800
ggatttgatt gcccgctttt atgcgggaaa actcaccgtg accgatcggc tacgcattct    4860
gagcggcaag ccgcccgttc ccgttttcgc ggcattgcag gcaattatga cgactcatcg    4920
ttgaagagcg actacatgaa accaactacg gtaattggtg cgggctttgg tggcctggca    4980
ctggcaattc gttacaggc gcaggtatt cctgttttgc tgcttgagca gcgcgacaag    5040
ccgggtggcc gggcttatgt ttatcaggag cagggctta cttttgatgc aggccctacc    5100
gttatcaccg atcccagcgc gattgaagaa ctgtttgctc tggccggtaa acagcttaag    5160
gattacgtcg agctgttgcc ggtcacgccg ttttatcgcc tgtgctggga gtccggcaag    5220
gtcttcaatt acgataacga ccaggcccag ttagaagcgc agatacagca gtttaatccg    5280
cgcgatgttg cgggttatcg agcgttcctt gactattcgc gtgccgtatt caatgagggc    5340
tatctgaagc tcggcactgt gcctttttta tcgttcaaag acatgcttcg ggccgcgccc    5400
cagttggcaa agctgcaggc atggcgcagc gtttacagta aagttgccgg ctacattgag    5460
gatgagcatc ttcggcaggc gttttctttt cactcgctct tagtgggggg gaatccgttt    5520
gcaacctcgt ccatttatac gctgattcac gcgttagaac gggaatgggg cgtctggttt    5580
ccacgcggtg gaaccggtgc gctggtcaat ggcatgatca agctgtttca ggatctgggc    5640
ggcgaagtcg tgcttaacgc ccgggtcagt catatggaaa ccgttgggga caagattcag    5700
```

```
gccgtgcagt tggaagacgg cagacggttt gaaacctgcg cggtggcgtc gaacgctgat    5760
gttgtacata cctatcgcga tctgctgtct cagcatcccg cagccgctaa gcaggcgaaa    5820
aaactgcaat ccaagcgtat gagtaactca ctgtttgtac tctattttgg tctcaaccat    5880
catcacgatc aactcgccca tcataccgtc tgttttgggc cacgctaccg tgaactgatt    5940
cacgaaattt ttaaccatga tggtctggct gaggattttt cgctttattt acacgcacct    6000
tgtgtcacgg atccgtcact ggcaccggaa gggtgcggca gctattatgt gctggcgcct    6060
gttccacact taggcacggc gaacctcgac tgggcggtag aaggaccccg actgcgcgat    6120 cgtattttg actaccttga gcaacattac atgcctggct gcgaagcca gttggtgacg    6180 caccgtatgt ttacgccgtt cgatttccgc gacgagctca atgcctggca aggttcggcc    6240
ttctcggttg aacctattct gacccagagc gcctggttcc gaccacataa ccgcgataag    6300
cacattgata atctttatct ggttggcgca ggcacccatc ctggcgcggg cattcccggc    6360
gtaatcggct cggcgaaggc gacggcaggc ttaatgctgg aggacctgat ttgacgaata    6420
cgtcattact gaatcatgcc gtcgaaacca tggcggttgg ctcgaaaagc tttgcgactg    6480
catcgacgct tttcgacgcc aaaacccgtc gcagcgtgct gatgctttac gcatggtgcc    6540
gccactgcga cgacgtcatt gacgatcaaa cactgggctt tcatgccgac cagccctctt    6600
cgcagatgcc tgagcagcgc ctgcagcagc ttgaaatgaa aacgcgtcag gcctacgccg    6660
gttcgcaaat gcacgagccc gcttttgccg cgtttcagga ggtcgcgatg gcgcatgata    6720
tcgctcccgc ctacgcgttc gaccatctgg aaggttttgc catggatgtg cgcgaaacgc    6780
gctacctgac actggacgat acgctgcgtt attgctatca cgtcgccggt gttgtgggcc    6840
tgatgatggc gcaaattatg ggcgttcgcg ataacgccac gctcgatcgc gcctgcgatc    6900
tcgggctggc tttccagttg accaacattg cgcgtgatat tgtcgacgat gctcaggtgg    6960
gccgctgtta tctgcctgaa agctggctgg aagaggaagg actgacgaaa gcgaattatg    7020
ctgcgccaga aaaccggcag gccttaagcc gtatcgccgg gcgactggta cgggaagcgg    7080
aaccctatta cgtatcatca atggccggtc tggcacaatt acccttacgc tcggcctggg    7140
ccatcgcgac agcgaagcag gtgtaccgta aaattggcgt gaaagttgaa caggccggta    7200
agcaggcctg ggatcatcgc cagtccacgt ccaccgccga aaattaacg cttttgctga    7260 cggcatccgg tcaggcagtt acttcccgga tgaagacgta tccaccccgt cctgctcatc    7320
tctggcagcg cccgatctag ccgcatgcct ttctctcagc gtcgcctgaa gtttagataa    7380
cggtggcgcg tacagaaaac caaaggacac gcagccctct tttcccctta cagcatgatg    7440
catacggtgg gccatgtata accgtttcag gtagcctttg cgcggtatgt agcggaacgg    7500
ccagcgctgg tgtaccagtc cgtcgtggac cataaaatac agtaaaccat aagcggtcat    7560
gcctgcacca atccactgga gcggccagat tcctgtactg ccgaagtaaa tcagggcaat    7620
cgacacaatg gcgaatacca cggcatagag atcgttaact tcaaatgcgc ctttacgcgg    7680
ttcatgatgt gaaagatgcc agccccaacc ccagccgtgc atgatgtatt tatgtgccag    7740
tgcagcaacc acttccatgc cgaccacggt gacaaacacg atcagggcat tccaaatcca    7800
caacataatt tctcaagggc gaattcgcgg ggatcctcta gagtcgacct gcaggcatgc    7860
aagcttggca ctgccgtcg ttttacaacg tcgtgactgg gaaaaccctg gcgttaccca    7920
acttaatcgc cttgcagcac atccccctt cgccagctgg cgtaatagcg aagaggcccg    7980
caccgatcgc ccttcccaac agttgcgcag cctgaatggc gaatggcgct gatgtccggc    8040
ggtgcttttg ccgttacgca ccacccegtc agtagctgaa caggagggac agctgataga    8100
```

-continued

| | |
|---|---|
| aacagaagcc actggagcac ctcaaaaaca ccatcataca ctaaatcagt aagttggcag | 8160 |
| catcacccga cgcactttgc gccgaataaa tacctgtgac ggaagatcac ttcgcagaat | 8220 |
| aaataaatcc tggtgtccct gttgataccg ggaagccctg ggccaacttt tggcgaaaat | 8280 |
| gagacgttga tcggcacgta agaggttcca actttcacca taatgaaata agatcactac | 8340 |
| cgggcgtatt ttttgagtta tcgagatttt caggagctaa ggaagctaaa atggagaaaa | 8400 |
| aaatcactgg atataccacc gttgatatat cccaatggca tcgtaaagaa cattttgagg | 8460 |
| catttcagtc agttgctcaa tgtacctata accagaccgt tcagctggat attacggcct | 8520 |
| ttttaaagac cgtaaagaaa aataagcaca agttttatcc ggcctttatt cacattcttg | 8580 |
| cccgcctgat gaatgctcat ccggaattt | 8609 |

<210> SEQ ID NO 55
<211> LENGTH: 6329
<212> TYPE: DNA
<213> ORGANISM: Artificial sequence
<220> FEATURE:
<223> OTHER INFORMATION: Plasmid pKD46

<400> SEQUENCE: 55

| | |
|---|---|
| catcgattta ttatgacaac ttgacggcta catcattcac ttttcttca caaccggcac | 60 |
| ggaactcgct cgggctggcc ccggtgcatt ttttaaatac ccgcgagaaa tagagttgat | 120 |
| cgtcaaaacc aacattgcga ccgacggtgg cgataggcat ccgggtggtg ctcaaaagca | 180 |
| gcttcgcctg gctgatacgt tggtcctcgc gccagcttaa gacgctaatc cctaactgct | 240 |
| ggcggaaaag atgtgacaga cgcgacggcg acaagcaaac atgctgtgcg acgctggcga | 300 |
| tatcaaaatt gctgtctgcc aggtgatcgc tgatgtactg acaagcctcg cgtacccgat | 360 |
| tatccatcgg tggatggagc gactcgttaa tcgcttccat cgccgcagt aacaattgct | 420 |
| caagcagatt tatcgccagc agctccgaat agcgcccttc ccttgcccg gcgttaatga | 480 |
| tttgcccaaa caggtcgctg aaatgcggct ggtgcgcttc atccgggcga agaaccccg | 540 |
| tattggcaaa tattgacggc cagttaagcc attcatgcca gtaggcgcgc ggacgaaagt | 600 |
| aaacccactg gtgataccat tcgcgagcct ccggatgacg accgtagtga tgaatctctc | 660 |
| ctggcgggaa cagcaaaata tcacccggtc ggcaaacaaa ttctcgtccc tgatttttca | 720 |
| ccacccctg accgcgaatg gtgagattga gaatataacc tttcattccc agcggtcggt | 780 |
| cgataaaaaa atcgagataa ccgttggcct caatcggcgt taaacccgcc accagatggg | 840 |
| cattaaacga gtatcccggc agcaggggat catttttgcgc ttcagccata cttttcatac | 900 |
| tcccgccatt cagagaagaa accaattgtc catattgcat cagacattgc cgtcactgcg | 960 |
| tcttttactg gctcttctcg ctaaccaaac cggtaacccc gcttattaaa agcattctgt | 1020 |
| aacaaagcgg gaccaaagcc atgacaaaaa cgcgtaacaa aagtgtctat aatcacggca | 1080 |
| gaaaagtcca cattgattat ttgcacggcg tcacactttg ctatgccata gcatttttat | 1140 |
| ccataagatt agcggatcct acctgacgct tttatcgca actctctact gtttctccat | 1200 |
| acccgttttt ttgggaattc gagctctaag gaggttataa aaaatggata ttaatactga | 1260 |
| aactgagatc aagcaaaagc attcactaac ccccttcct gttttcctaa tcagcccggc | 1320 |
| atttcgcggg cgatatttc acagctattt caggagttca gccatgaacg cttattacat | 1380 |
| tcaggatcgt cttgaggctc agagctgggc gcgtcactac cagcagctcg cccgtgaaga | 1440 |
| gaaagaggca gaactggcag acgacatgga aaaaggcctg ccccagcacc tgtttgaatc | 1500 |

```
gctatgcatc gatcatttgc aacgccacgg ggccagcaaa aaatccatta cccgtgcgtt   1560
tgatgacgat gttgagtttc aggagcgcat ggcagaacac atccggtaca tggttgaaac   1620
cattgctcac caccaggttg atattgattc agaggtataa aacgaatgag tactgcactc   1680
gcaacgctgg ctgggaagct ggctgaacgt gtcggcatgg attctgtcga cccacaggaa   1740
ctgatcacca ctcttcgcca gacggcattt aaaggtgatg ccagcgatgc gcagttcatc   1800
gcattactga tcgttgccaa ccagtacggc cttaatccgt ggacgaaaga aatttacgcc   1860
tttcctgata agcagaatgg catcgttccg gtggtgggcg ttgatggctg gtcccgcatc   1920
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacgggcc gtggcagtcg   2100 catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
gctcttggat tcctgaaaca gaaagccgca gagcagaagg tggcagcatg acaccggaca   2460
ttatcctgca gcgtaccggg atcgatgtga gagctgtcga acaggggat gatgcgtggc   2520 acaaattacg gctcggcgtc atcaccgctt cagaagttca aacgtgata gcaaaacccc   2580 gctccggaaa gaagtggcct gacatgaaaa tgtcctactt ccacaccctg cttgctgagg   2640
tttgcaccgg tgtggctccg gaagttaacg ctaaagcact ggcctgggga aaacagtacg   2700
agaacgacgc cagaaccctg tttgaattca cttccggcgt gaatgttact gaatccccga   2760
tcatctatcg cgacgaaagt atgcgtaccg cctgctctcc cgatggttta tgcagtgacg   2820
gcaacggcct tgaactgaaa tgcccgtta cctcccggga tttcatgaag ttccggctcg   2880
gtggtttcga ggccataaag tcagcttaca tggcccaggt gcagtacagc atgtgggtga   2940
cgcgaaaaaa tgcctggtac tttgccaact atgacccgcg tatgaagcgt gaaggcctgc   3000
attatgtcgt gattgagcgg gatgaaaagt acatggcgag ttttgacgag atcgtgccgg   3060
agttcatcga aaaatggac gaggcactgg ctgaaattgg ttttgtattt ggggagcaat   3120
ggcgatgacg catcctcacg ataatatccg ggtaggcgca atcactttcg tctactccgt   3180
tacaaagcga ggctgggtat ttcccggcct ttctgttatc cgaaatccac tgaaagcaca   3240
gcggctggct gaggagataa ataataaacg aggggctgta tgcacaaagc atcttctgtt   3300
gagttaagaa cgagtatcga gatggcacat agccttgctc aaattggaat caggtttgtg   3360
ccaataccag tagaaacaga cgaagaatcc atgggtatgg acagttttcc ctttgatatg   3420
taacggtgaa cagttgttct actttttgttt gttagtcttg atgcttcact gatagataca   3480
agagccataa gaacctcaga tccttccgta tttagccagt atgttctcta gtgtggttcg   3540 ttgttttttgc gtgagccatg agaacgaacc attgagatca tacttacttt gcatgtcact   3600
caaaattttt gcctcaaaac tggtgagctg aattttttgca gttaaagcat cgtgtagtgt   3660
ttttcttagt ccgttacgta ggtaggaatc tgatgtaatg gttgttggta ttttgtcacc   3720
attcattttt atctggttgt tctcaagttc ggttacgaga tccatttgtc tatctagttc   3780
aacttggaaa atcaacgtat cagtcgggcg gcctcgctta tcaaccacca atttcatatt   3840
gctgtaagtg tttaaatctt tacttattgg tttcaaaacc cattggttaa gccttttaaa   3900
```

```
ctcatggtag ttattttcaa gcattaacat gaacttaaat tcatcaaggc taatctctat    3960
atttgccttg tgagttttct tttgtgttag ttcttttaat aaccactcat aaatcctcat    4020
agagtatttg ttttcaaaag acttaacatg ttccagatta tattttatga attttttaa    4080 ctggaaaaga taaggcaata tctcttcact aaaaactaat tctaattttt cgcttgagaa    4140
cttggcatag tttgtccact ggaaaatctc aaagccttta accaaggat tcctgatttc     4200 cacagttctc gtcatcagct ctctggttgc tttagctaat acaccataag cattttccct    4260
actgatgttc atcatctgag cgtattggtt ataagtgaac gataccgtcc gttctttcct    4320
tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc tttccttg agttgtgggt atctgtaaat tctgctagac       4560
ctttgctgga aaacttgtaa attctgctag accctctgta aattccgcta gacctttgtg    4620 tgttttttt gtttatattc aagtggttat aatttataga ataaagaaag aataaaaaaa     4680
gataaaaaga atagatccca gccctgtgta taactcacta ctttagtcag ttccgcagta    4740
ttacaaaagg atgtcgcaaa cgctgtttgc tcctctacaa aacagacctt aaaaccctaa    4800
aggcttaagt agcaccctcg caagctcggt tgcggccgca atcgggcaaa tcgctgaata    4860
ttccttttgt ctccgaccat caggcacctg agtcgctgtc ttttcgtga cattcagttc      4920 gctgcgctca cggctctggc agtgaatggg ggtaaatggc actacaggcg ccttttatgg    4980
attcatgcaa ggaaactacc cataatacaa gaaaagcccg tcacgggctt ctcagggcgt    5040
tttatggcgg gtctgctatg tggtgctatc tgactttttg ctgttcagca gttcctgccc    5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280 ttaaaatga agttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggag ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
tgttgccatt gctacaggca tcgtggtgtc acgctcgtcg tttggtatgg cttcattcag    5700
ctccggttcc caacgatcaa ggcgagttac atgatccccc atgttgtgca aaaaagcggt    5760
tagctccttc ggtcctccga tcgttgtcag aagtaagttg gccgcagtgt tatcactcat    5820
ggttatggca gcactgcata attctcttac tgtcatgcca tccgtaagat gcttttctgt    5880
gactggtgag tactcaacca agtcattctg agaatagtgt atgcggcgac cgagttgctc    5940
ttgcccggcg tcaatacggg ataataccgc gccacatagc agaactttaa aagtgctcat    6000
cattggaaaa cgttcttcgg ggcgaaaact ctcaaggatc ttaccgctgt tgagatccag    6060
ttcgatgtaa cccactcgtg cacccaactg atcttcagca tcttttactt tcaccagcgt    6120
ttctgggtga gcaaaaacag gaaggcaaaa tgccgcaaaa aagggaataa gggcgacacg    6180
gaaatgttga atactcatac tcttcctttt tcaatattat tgaagcattt atcagggtta    6240
```

-continued

| | |
|---|---|
| ttgtctcatg agcggataca tatttgaatg tatttagaaa aataaacaaa tagggggttcc | 6300 |
| gcgcacattt ccccgaaaag tgccacctg | 6329 |

<210> SEQ ID NO 56
<211> LENGTH: 3423
<212> TYPE: DNA
<213> ORGANISM: Artificial sequence
<220> FEATURE:
<223> OTHER INFORMATION: Plasmid pSUH5

<400> SEQUENCE: 56

| | |
|---|---|
| agattgcagc attacacgtc ttgagcgatt gtgtaggctg agctgcttc gaagttccta | 60 |
| tactttctag agaataggaa cttcggaata ggaacttcaa gatcccctca cgctgccgca | 120 |
| agcactcagg gcgcaaggc tgctaaagga agcggaacac gtagaaagcc agtccgcaga | 180 |
| aacggtgctg accccggatg aatgtcagct actgggctat ctggacaagg gaaaacgcaa | 240 |
| gcgcaaagag aaagcaggta gcttgcagtg ggcttacatg gcgatagcta gactgggcgg | 300 |
| ttttatggac agcaagcgaa ccggaattgc cagctggggc gccctctggt aaggttggga | 360 |
| agccctgcaa agtaaactgg atggctttct tgccgccaag gatctgatgg cgcaggggat | 420 |
| caagatctga tcaagagaca ggatgaggat cgtttcgcat gattgaacaa gatggattgc | 480 |
| acgcaggttc tccggccgct tgggtggaga ggctattcgg ctatgactgg gcacaacaga | 540 |
| caatcggctg ctctgatgcc gccgtgttcc ggctgtcagc gcagggcgc ccggttcttt | 600 |
| ttgtcaagac cgacctgtcc ggtgccctga atgaactgca ggacgaggca gcgcggctat | 660 |
| cgtggctggc cacgacgggc gttccttgcg cagctgtgct cgacgttgtc actgaagcgg | 720 |
| gaagggactg gctgctattg ggcgaagtgc cggggcagga tctcctgtca tctcaccttg | 780 |
| ctcctgccga gaaagtatcc atcatggctg atgcaatgcg gcggctgcat acgcttgatc | 840 |
| cggctacctg cccattcgac caccaagcga aacatcgcat cgagcgagca cgtactcgga | 900 |
| tggaagccgg tcttgtcgat caggatgatc tggacgaaga gcatcagggg ctcgcgccag | 960 |
| ccgaactgtt cgccaggctc aaggcgcgca tgcccgacgg cgaggatctc gtcgtgaccc | 1020 |
| atggcgatgc ctgcttgccg aatatcatgg tggaaaatgg ccgcttttct ggattcatcg | 1080 |
| actgtggccg gctgggtgtg gcggaccgct atcaggacat agcgttggct acccgtgata | 1140 |
| ttgctgaaga gcttggcggc gaatgggctg accgcttcct cgtgctttac ggtatcgccg | 1200 |
| ctcccgattc gcagcgcatc gccttctatc gccttcttga cgagttcttc tgagcgggac | 1260 |
| tctggggttc gaaatgaccg accaagcgac gcccaacctg ccatcacgag atttcgattc | 1320 |
| caccgccgcc ttctatgaaa ggttgggctt cggaatcgtt ttccgggacg ccggctggat | 1380 |
| gatcctccag cgcggggatc tcatgctgga gttcttcgcc cacccagct tcaaaagcgc | 1440 |
| tctgaagttc ctatactttc tagagaatag gaacttcgga ataggaacta aggaggatat | 1500 |
| tcactataaa aataggcgta tcacgaggcc ctttcgtctt cacctcgaga aatcataaaa | 1560 |
| aatttatttg ctttgtgagc ggataacaat tataatagat tcaattgtga gcggataaca | 1620 |
| atttcacaca gaattcatta aagaggagaa attaactcat atggaccatg ctaattccc | 1680 |
| atgtcagccg ttaagtgttc ctgtgtcact gaaaattgct ttgagaggct ctaagggctt | 1740 |
| ctcagtgcgt tacatccctg gcttgttgtc cacaaccgtt aaaccttaaa agctttaaaa | 1800 |
| gccttatata ttcttttttt tcttataaaa cttaaaacct tagaggctat ttaagttgct | 1860 |
| gatttatatt aattttattg ttcaaacatg agagcttagt acgtgaaaca tgagagctta | 1920 |
| gtacgttagc catgagagct tagtacgtta gccatgaggg tttagttcgt taaacatgag | 1980 |

```
agcttagtac gttaaacatg agagcttagt acgtgaaaca tgagagctta gtacgtacta      2040
tcaacaggtt gaactgcgga tcttgcggcc gcaaaaatta aaaatgaagt tttaaatcaa      2100
tctaaagtat atatgagtaa acttggtctg acagttacca atgcttaatc agtgaggcac      2160
ctatctcagc gatctgtcta tttcgttcat ccatagttgc ctgactcccc gtcgtgtaga      2220
taactacgat acgggagggc ttaccatctg gccccagtgc tgcaatgata ccgcgagacc      2280
cacgctcacc ggctccagat ttatcagcaa taaaccagcc agccgaaagg gccgagcgca      2340
gaagtggtcc tgcaacttta tccgcctcca tccagtctat taattgttgc cgggaagcta      2400
gagtaagtag ttcgccagtt aatagtttgc gcaacgttgt tgccattgct acaggcatcg      2460
tggtgtcacg ctcgtcgttt ggtatggctt cattcagctc cggttcccaa cgatcaaggc      2520
gagttacatg atcccccatg ttgtgcaaaa aagcggttag ctccttcggt cctccgatcg      2580
ttgtcagaag taagttggcc gcagtgttat cactcatggt tatggcagca ctgcataatt      2640
ctcttactgt catgccatcc gtaagatgct tttctgtgac tggtgagtac tcaaccaagt      2700
cattctgaga atagtgtatg cggcgaccga gttgctcttg cccggcgtca atacgggata      2760
ataccgcgcc acatagcaga actttaaaag tgctcatcat tggaaaacgt tcttcggggc      2820
gaaaactctc aaggatctta ccgctgttga tccagttc gatgtaaccc actcgtgcac       2880
ccaactgatc ttcagcatct tttactttca ccagcgtttc tgggtgagca aaaacaggaa      2940
ggcaaaatgc cgcaaaaaag gaataagggc gacacggaa atgttgaata ctcatactct      3000
tcctttttca atattattga agcatttatc agggttattg tctcatgagc ggatacatat      3060
ttgaatgtat ttagaaaaat aaacaaatag gggttccgcg cacatttccc cgaaaagtgc      3120
cacctgcatc gatggccccc cgatggtagt gtggggtctc cccatgcgag agtagggaac      3180
tgccaggcat caaataaaac gaaaggctca gtcgaaagac tgggcctttc gttttatctg      3240
ttgtttgtcg gtgaacgctc tcctgagtag acaaatccg ccgggagcgg atttgaacgt      3300
tgcgaagcaa cggcccggag ggtggcgggc aggacgcccg ccataaactg ccaggcatca      3360
aattaagcag aaggccatcc tgacggatgg cctttttgcg tggccagtgc caagcttgca      3420
tgc                                                                   3423

<210> SEQ ID NO 57
<211> LENGTH: 156
<212> TYPE: DNA
<213> ORGANISM: Artificial sequence
<220> FEATURE:
<223> OTHER INFORMATION: Phage T5 promoter

<400> SEQUENCE: 57
ctataaaaat aggcgtatca cgaggccctt tcgtcttcac ctcgagaaat cataaaaaat        60
ttatttgctt tgtgagcgga taacaattat aatagattca attgtgagcg gataacaatt       120
tcacacagaa ttcattaaag aggagaaatt aactca                                 156
```